United States Patent
Doyle

(10) Patent No.: US 9,737,374 B2
(45) Date of Patent: Aug. 22, 2017

(54) ADAPTIVE ARM SUPPORT SYSTEMS AND METHODS FOR USE

(71) Applicant: LEVITATE TECHNOLOGIES, INC., San Diego, CA (US)

(72) Inventor: Mark C. Doyle, Del Mar, CA (US)

(73) Assignee: LEVITATE TECHNOLOGIES, INC., San Diego, CA (US)

(*) Notice: Subject to any disclaimer, the term of this patent is extended or adjusted under 35 U.S.C. 154(b) by 653 days.

(21) Appl. No.: 14/102,466

(22) Filed: Dec. 10, 2013

(65) Prior Publication Data

US 2014/0158839 A1 Jun. 12, 2014

Related U.S. Application Data

(60) Provisional application No. 61/735,894, filed on Dec. 11, 2012, provisional application No. 61/879,088, filed on Sep. 17, 2013.

(51) Int. Cl.
*A61B 90/60* (2016.01)
*A61F 5/01* (2006.01)
*B25J 9/00* (2006.01)

(52) U.S. Cl.
CPC .............. *A61B 90/60* (2016.02); *A61F 5/013* (2013.01); *B25J 9/0006* (2013.01);
(Continued)

(58) Field of Classification Search
CPC ........ A61F 2/54; A61F 2002/546; A61F 5/37; A61F 5/3738; A61F 5/05858;
(Continued)

(56) References Cited

U.S. PATENT DOCUMENTS

| 4,180,870 A * | 1/1980 | Radulovic ............ B25J 9/0006 |
| | | 601/33 |
| 4,298,149 A * | 11/1981 | Gottschalk ............ A45F 3/10 |
| | | 224/201 |

(Continued)

FOREIGN PATENT DOCUMENTS

| GB | 2472036 B | 12/2013 |
| JP | 10071161 A | 3/1998 |

(Continued)

OTHER PUBLICATIONS

European Patent Office, Supplemental European Search Report for corresponding European Application No. EP 13 86 2698, Aug. 10, 2016, 6 pages.

(Continued)

*Primary Examiner* — Thomas J Sweet
*Assistant Examiner* — Christie Bahena
(74) *Attorney, Agent, or Firm* — William A English; Vista IP Law Group LLP

(57) ABSTRACT

Systems and methods are provided for supporting an arm of a user using a harness configured to be worn on a body of a user; and an arm support coupled to the harness configured to support an arm of the user, the arm support configured to accommodate movement of the arm while following the movement without substantially interfering with the movement of the user's arm. One or more compensation elements may be coupled to the arm support to apply an offset force to at least partially offset a gravitational force acting on the arm as the user moves and the arm support follows the movement of the user's arm, the one or more compensation elements providing a force profile that varies the offset force based on an orientation of the arm support.

11 Claims, 48 Drawing Sheets

(52) U.S. Cl.
CPC ............... *A61F 2005/0134* (2013.01); *A61F 2005/0155* (2013.01); *A61F 2005/0179* (2013.01)

(58) Field of Classification Search
CPC .... A61F 5/3761; A61F 5/3769; A61F 5/3792; A61H 1/00; A61H 1/005; A61H 1/006; A61H 1/008; A61H 1/0229; A61H 1/0274; A61H 1/0281; B25J 9/0006; B25J 11/00; A45F 2005/00; A45F 2005/002; A45F 2005/0118; A45F 2005/0134; A45F 2005/0155; A45F 2005/0197; A41D 13/08
See application file for complete search history.

(56) References Cited

U.S. PATENT DOCUMENTS

| | | | | |
|---|---|---|---|---|
| 4,949,711 | A * | 8/1990 | Gyovai | A61F 5/0118 601/40 |
| 5,111,983 | A | 5/1992 | Simmons et al. | |
| 5,170,777 | A * | 12/1992 | Reddy | A61H 1/0274 482/44 |
| 5,624,398 | A * | 4/1997 | Smith | B25J 3/04 604/95.01 |
| 5,961,512 | A * | 10/1999 | Purnell | A61F 5/3761 606/1 |
| 7,673,776 | B2 * | 3/2010 | May | G10D 13/00 224/265 |
| 2008/0009771 | A1 * | 1/2008 | Perry | B25J 9/0006 600/587 |
| 2011/0127390 | A1 * | 6/2011 | Brown | A47C 1/03 248/118 |
| 2012/0172769 | A1 * | 7/2012 | Garrec | A61F 5/013 601/33 |

FOREIGN PATENT DOCUMENTS

| | | |
|---|---|---|
| JP | 2002153115 A | 5/2002 |
| JP | 2009273711 A | 5/2008 |
| JP | 2008295696 A | 12/2008 |
| WO | WO 2009029693 A1 | 3/2009 |
| WO | WO 2012099995 A3 | 7/2012 |
| WO | WO 2013106532 A1 | 7/2013 |
| WO | WO 2013155065 A1 | 10/2013 |

OTHER PUBLICATIONS

Written Opinion of the International Searching Authority dated Aug. 31, 2012 in International Application No. PCT/US2012/02177 filed Jan. 18, 2012, Form ISA 237, (4 pages).
PCT International Search Report dated Nov. 11, 2013 in International Application No. PCT/US2013/052782 filed Jul. 30, 2013, Form ISA 210, (3 pages).

* cited by examiner

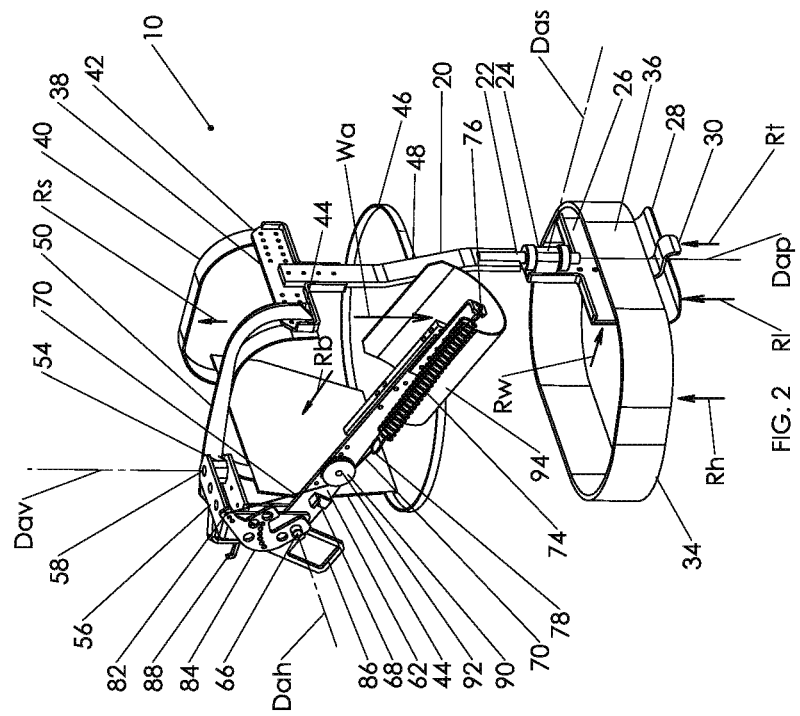
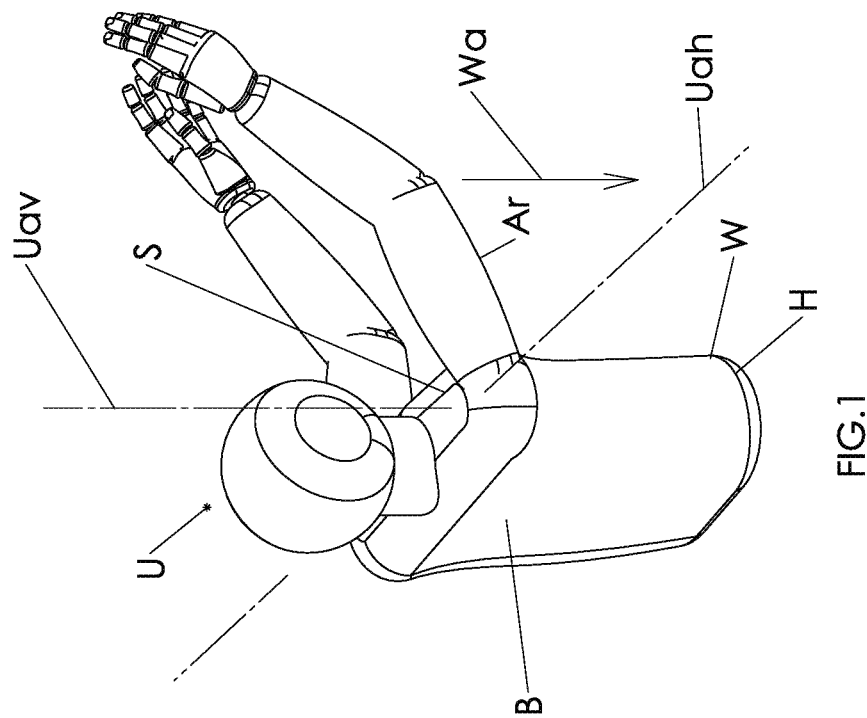
FIG. 2
FIG. 1

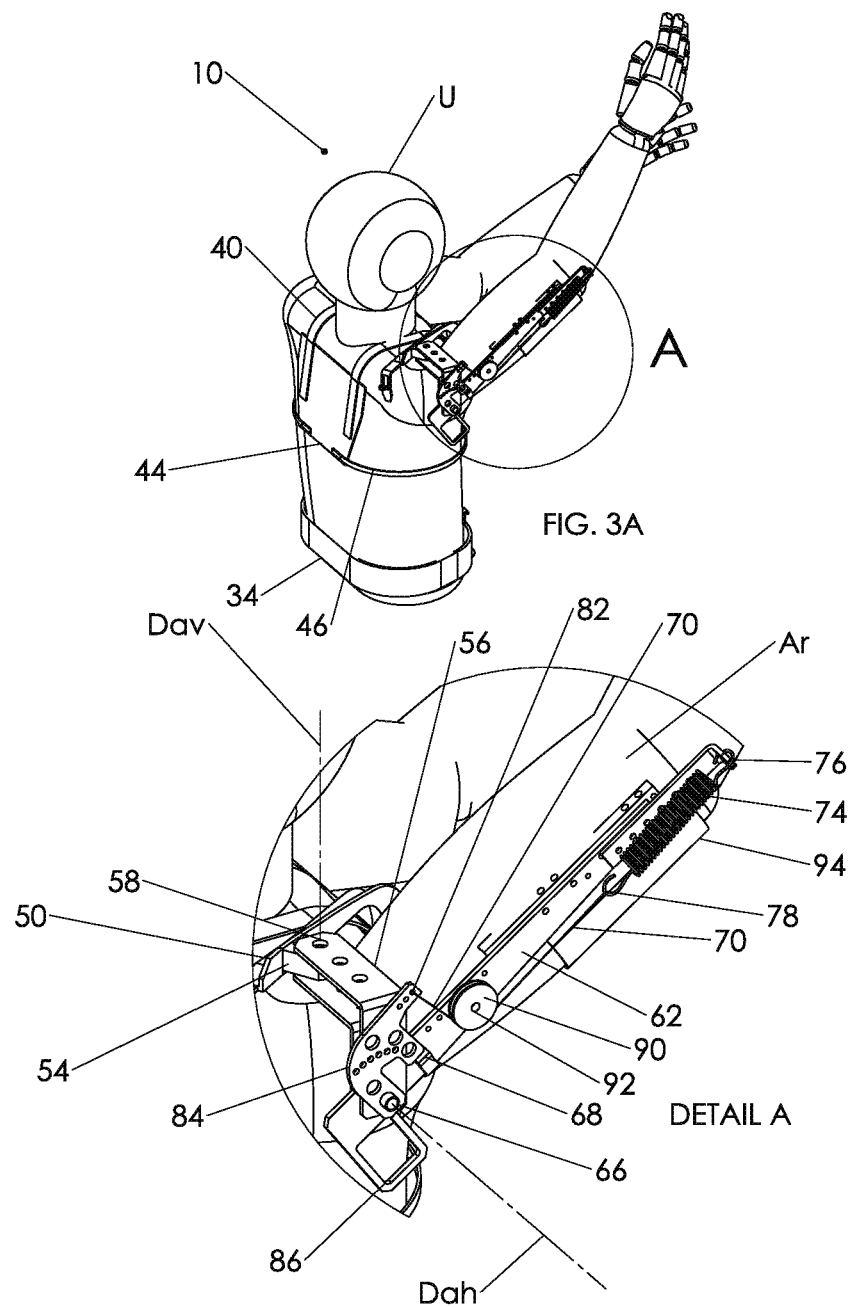

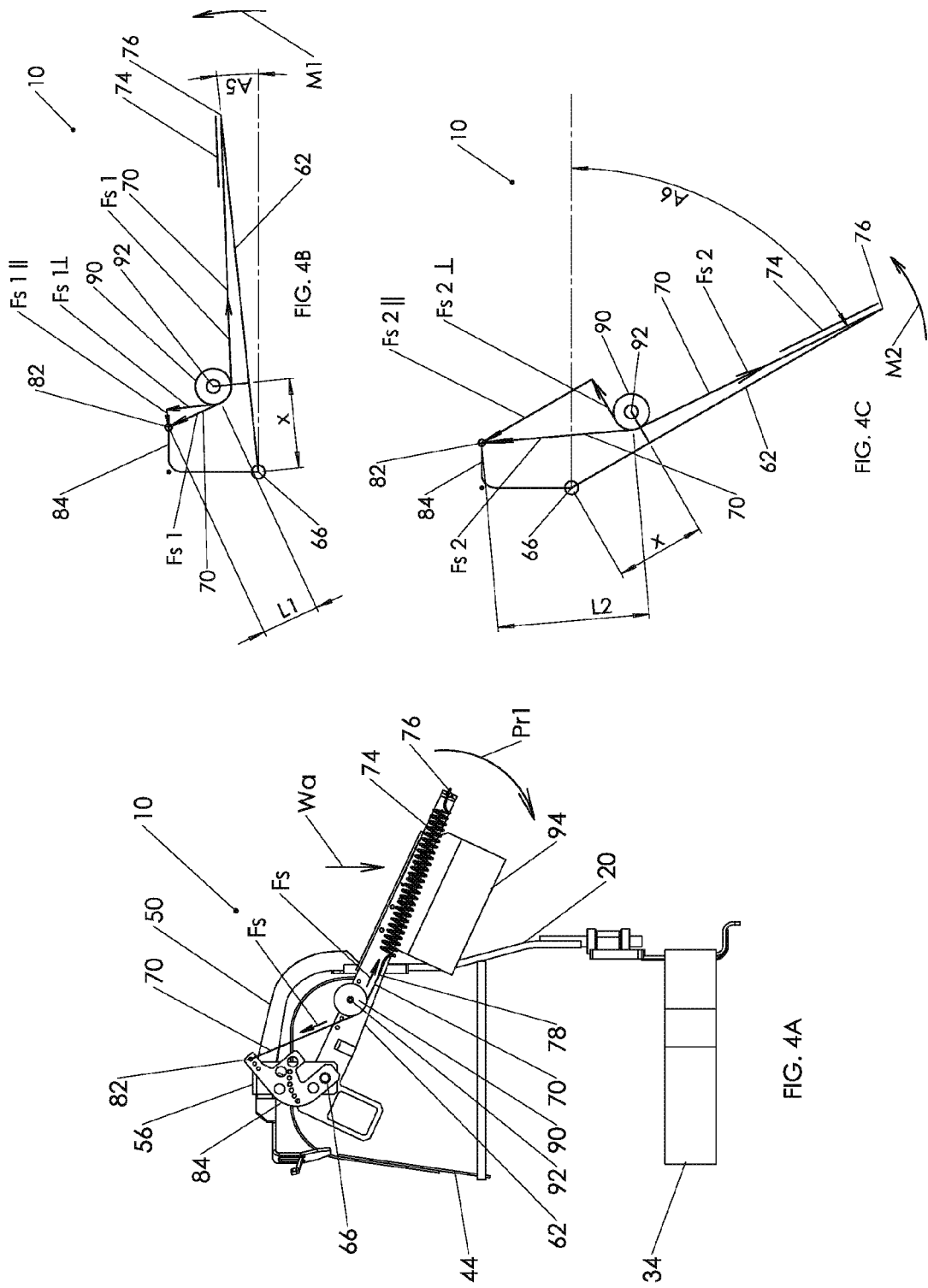

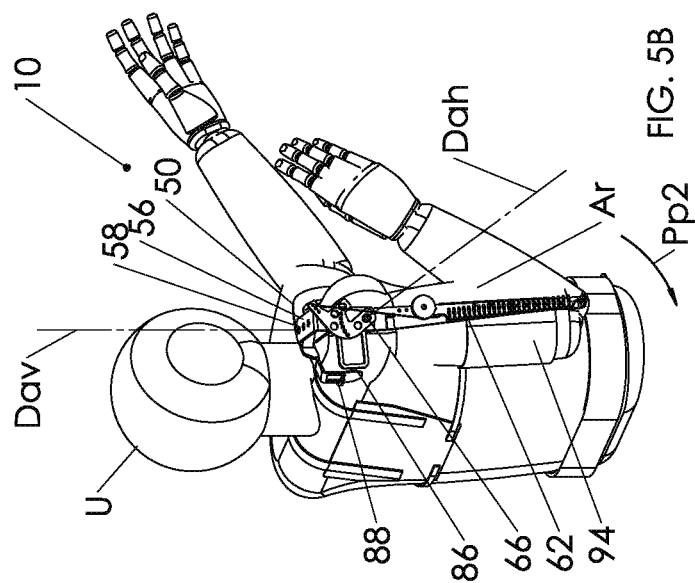
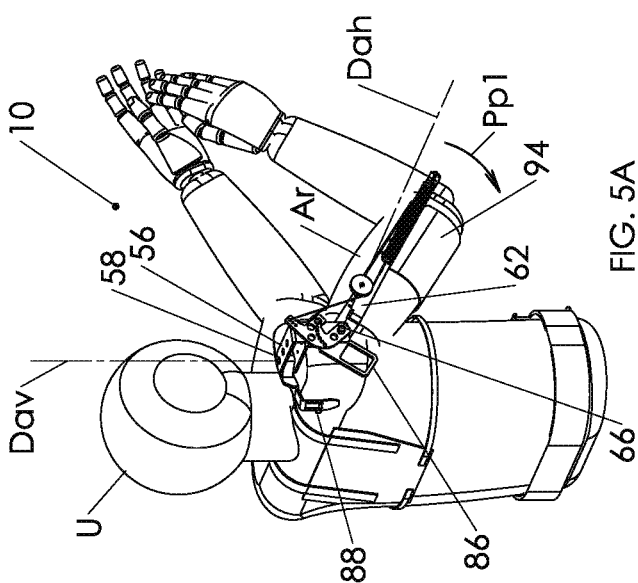

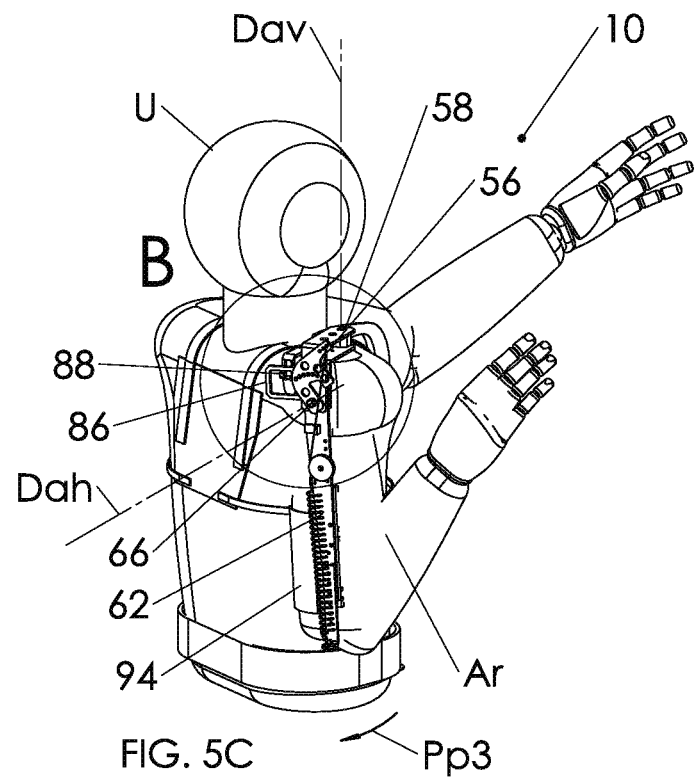
FIG. 5C
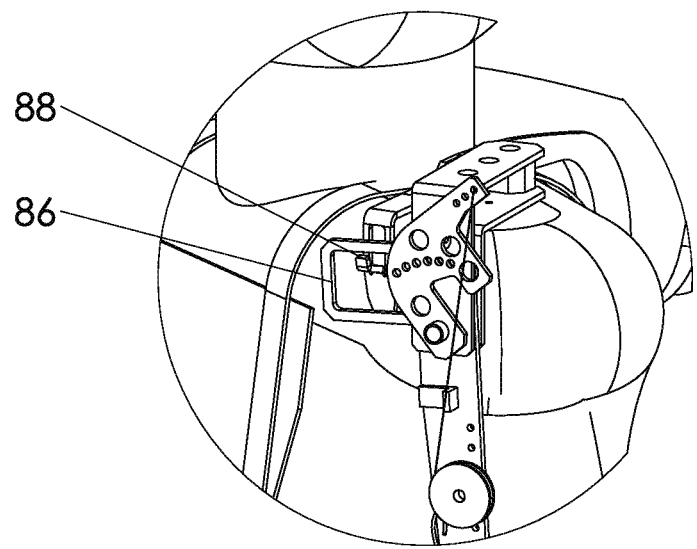
DETAIL B

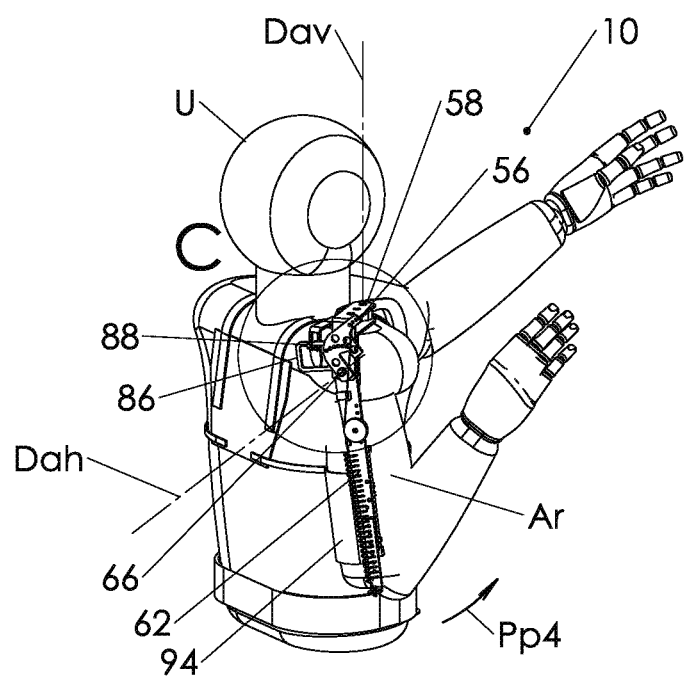
FIG. 5D
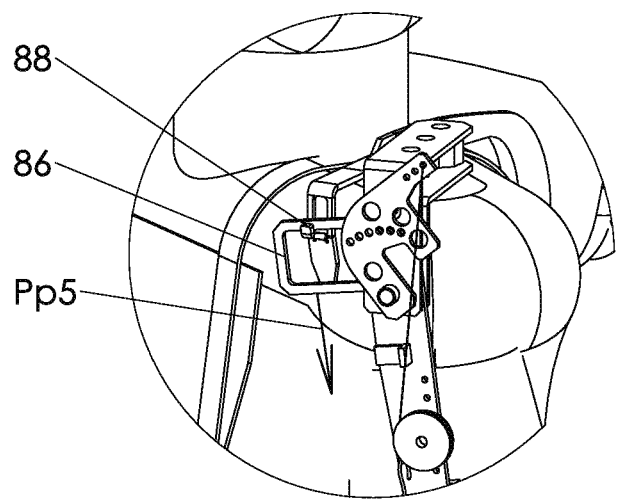
DETAIL C

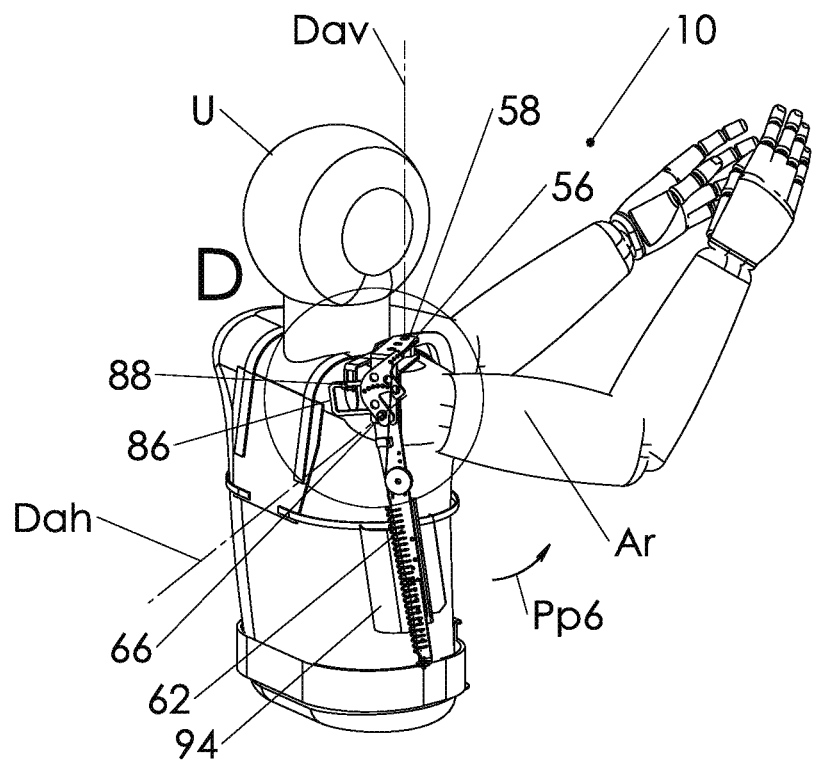
FIG. 5E
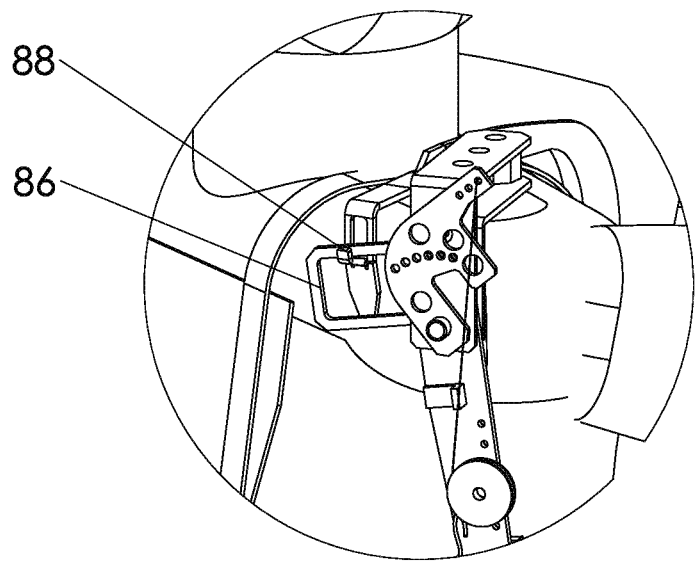
DETAIL D

DETAIL E

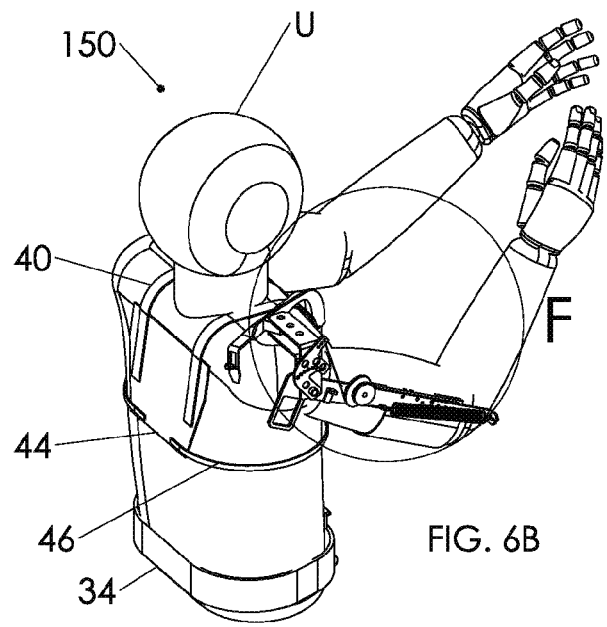
FIG. 6B
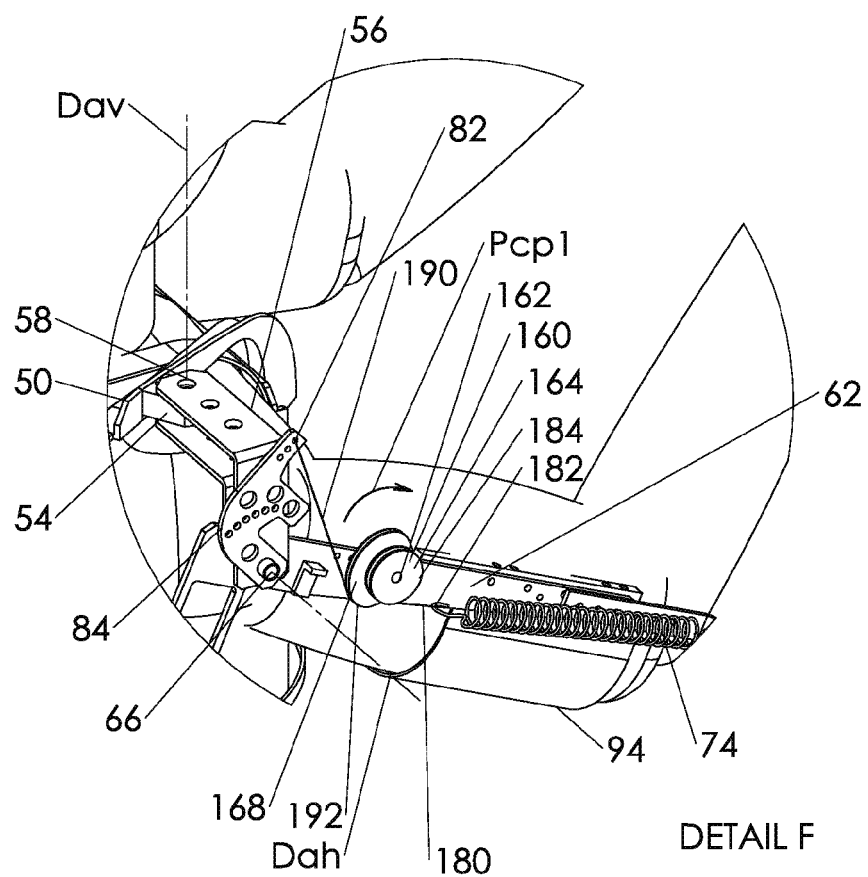
DETAIL F

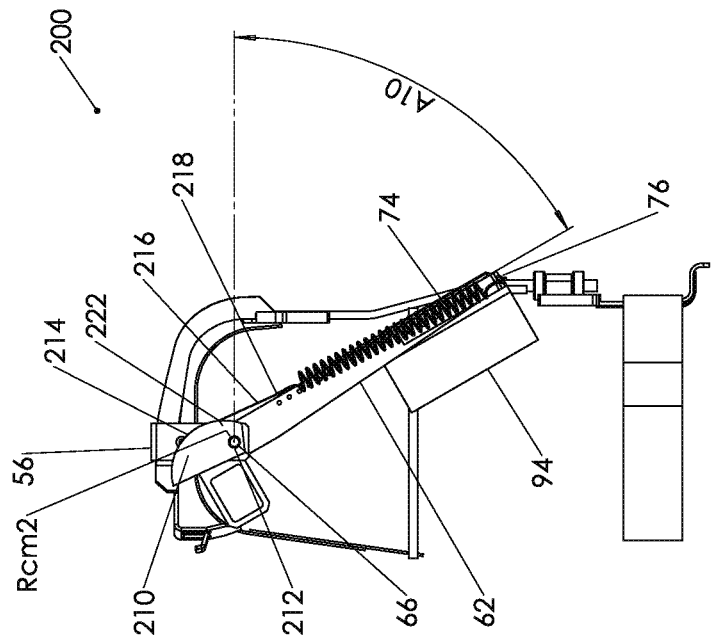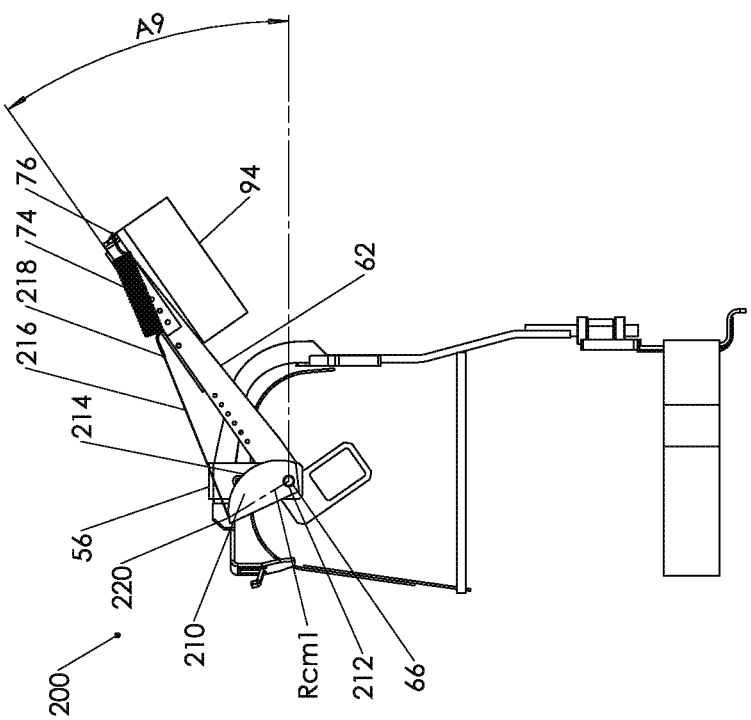

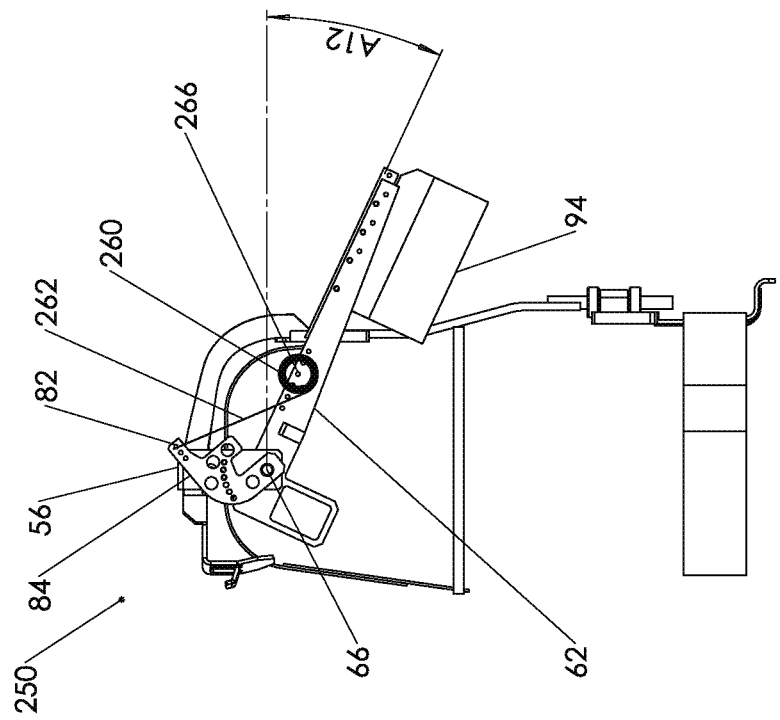
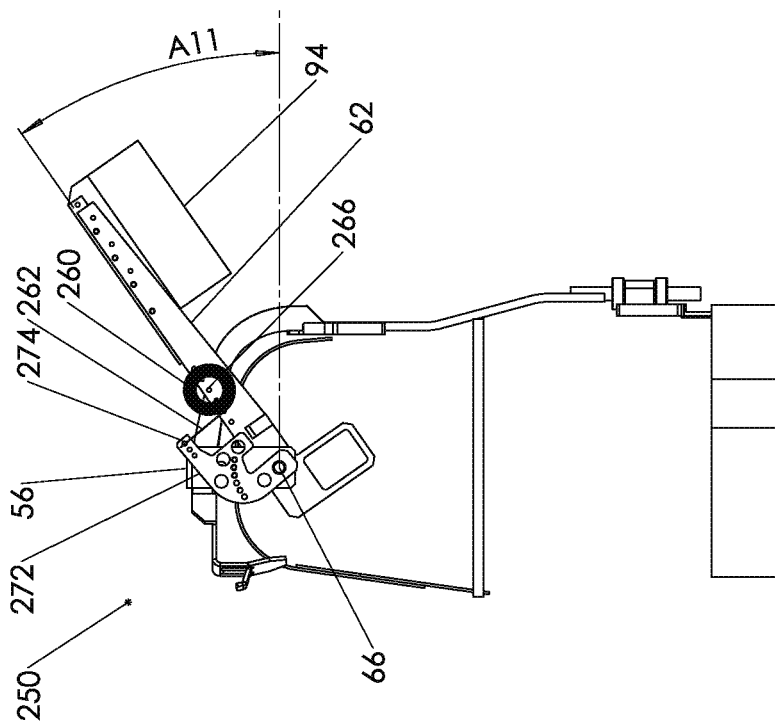

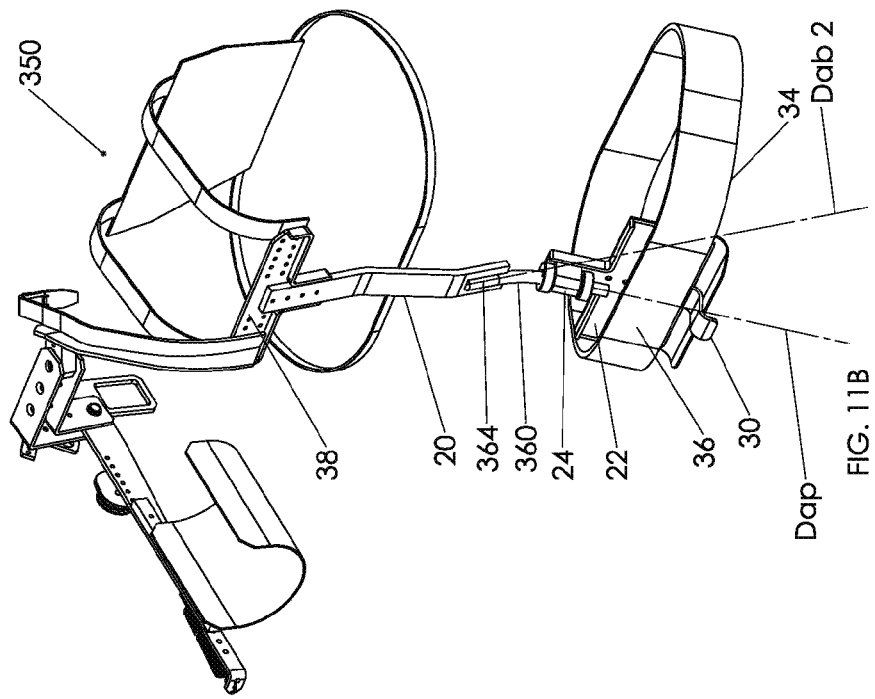
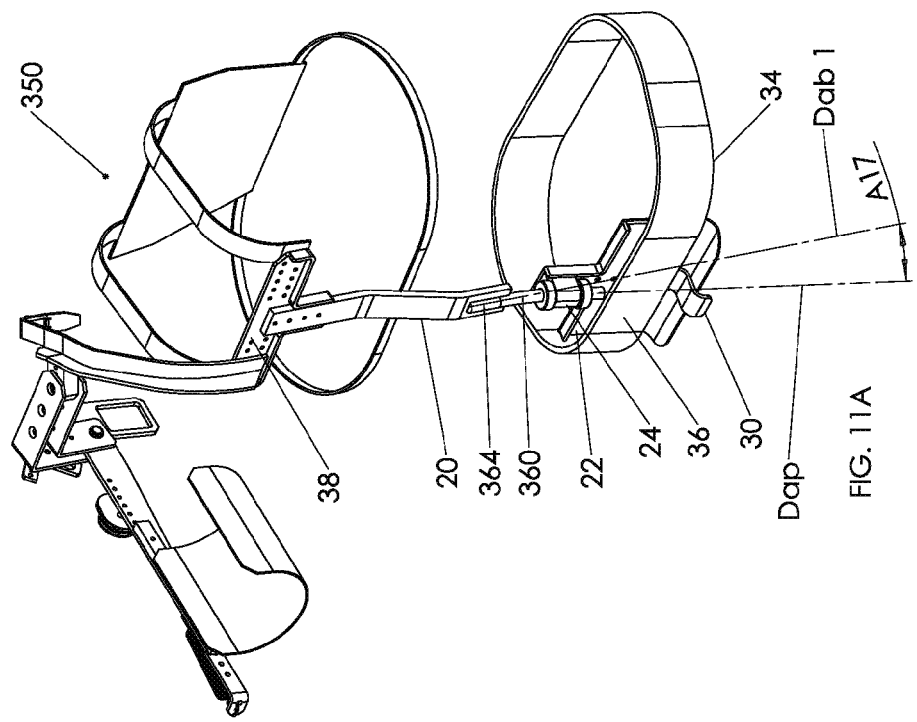

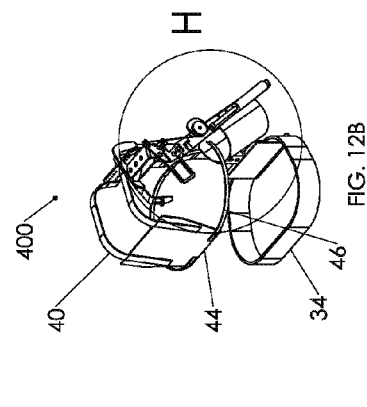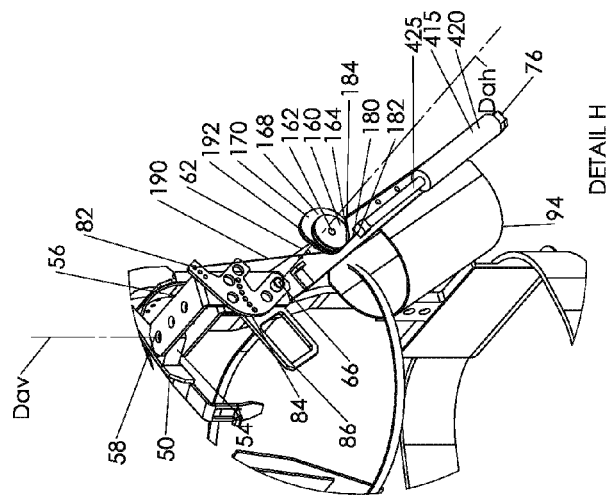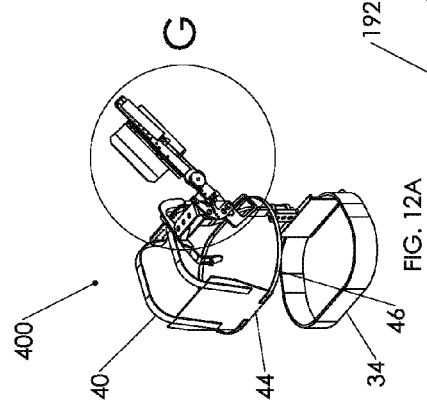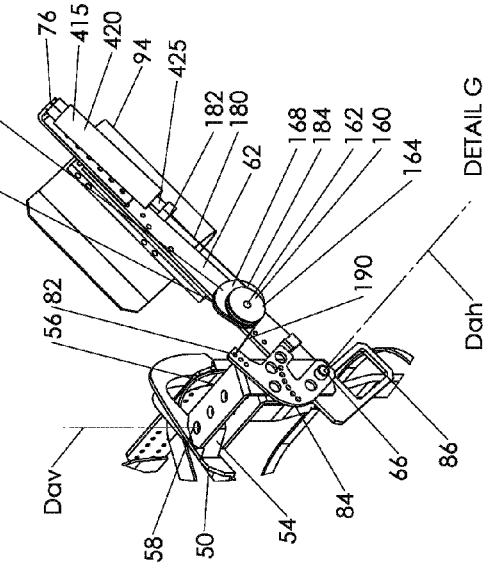

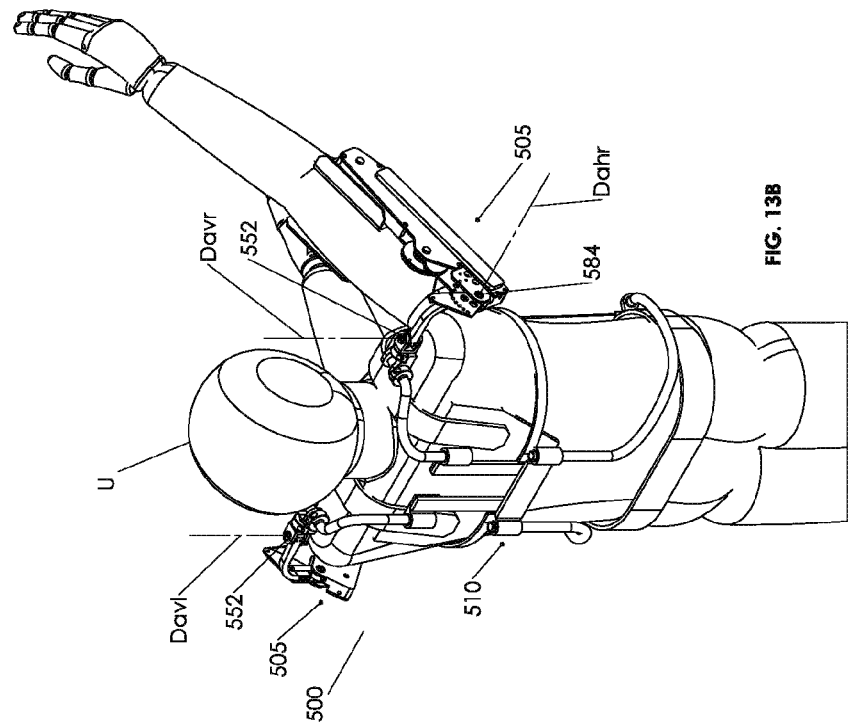
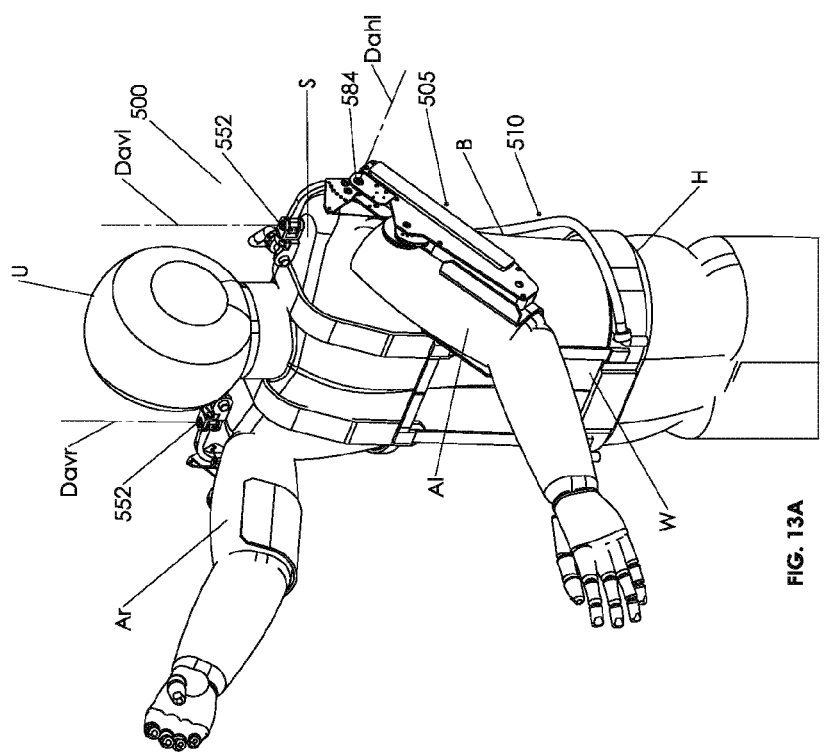

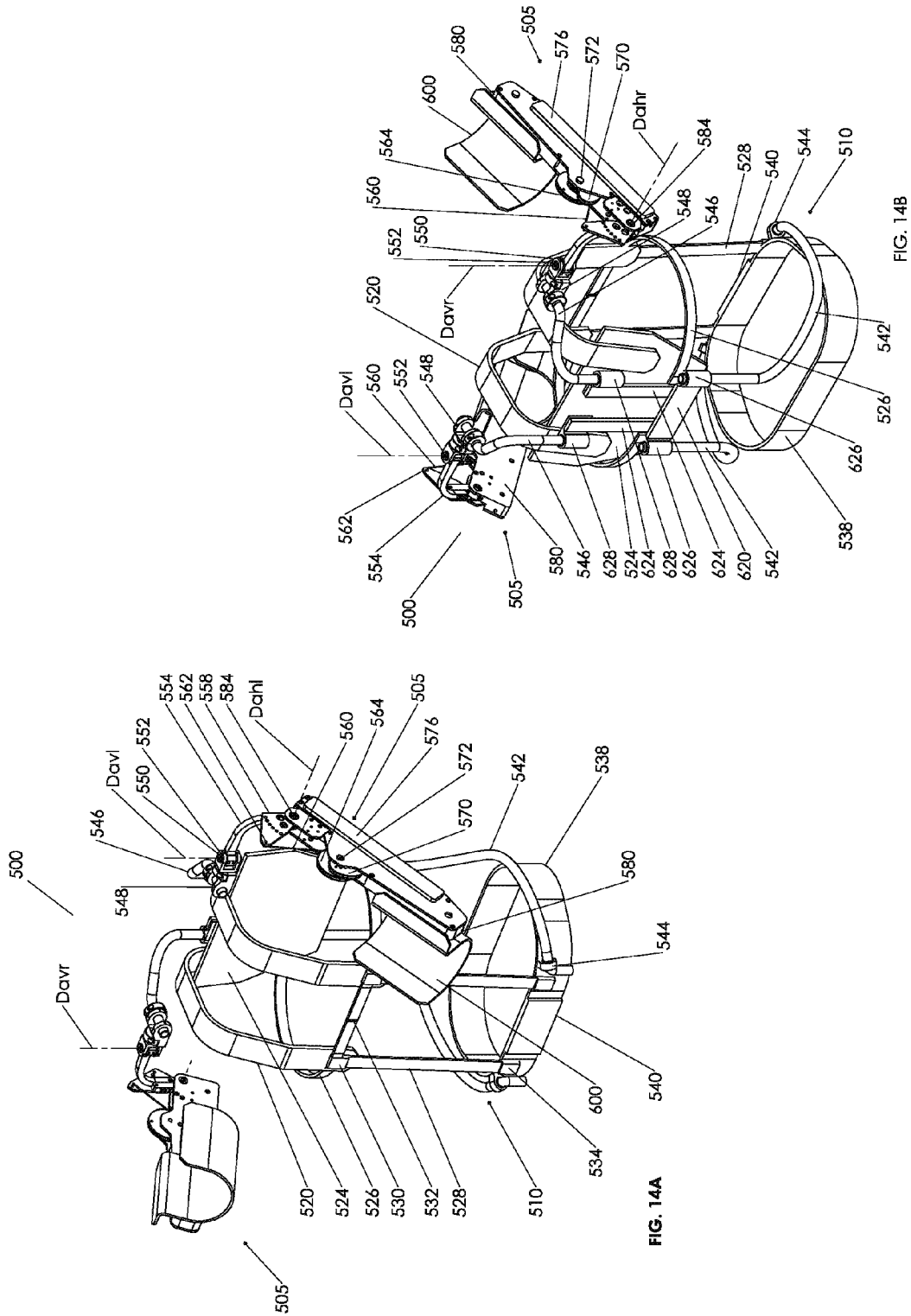

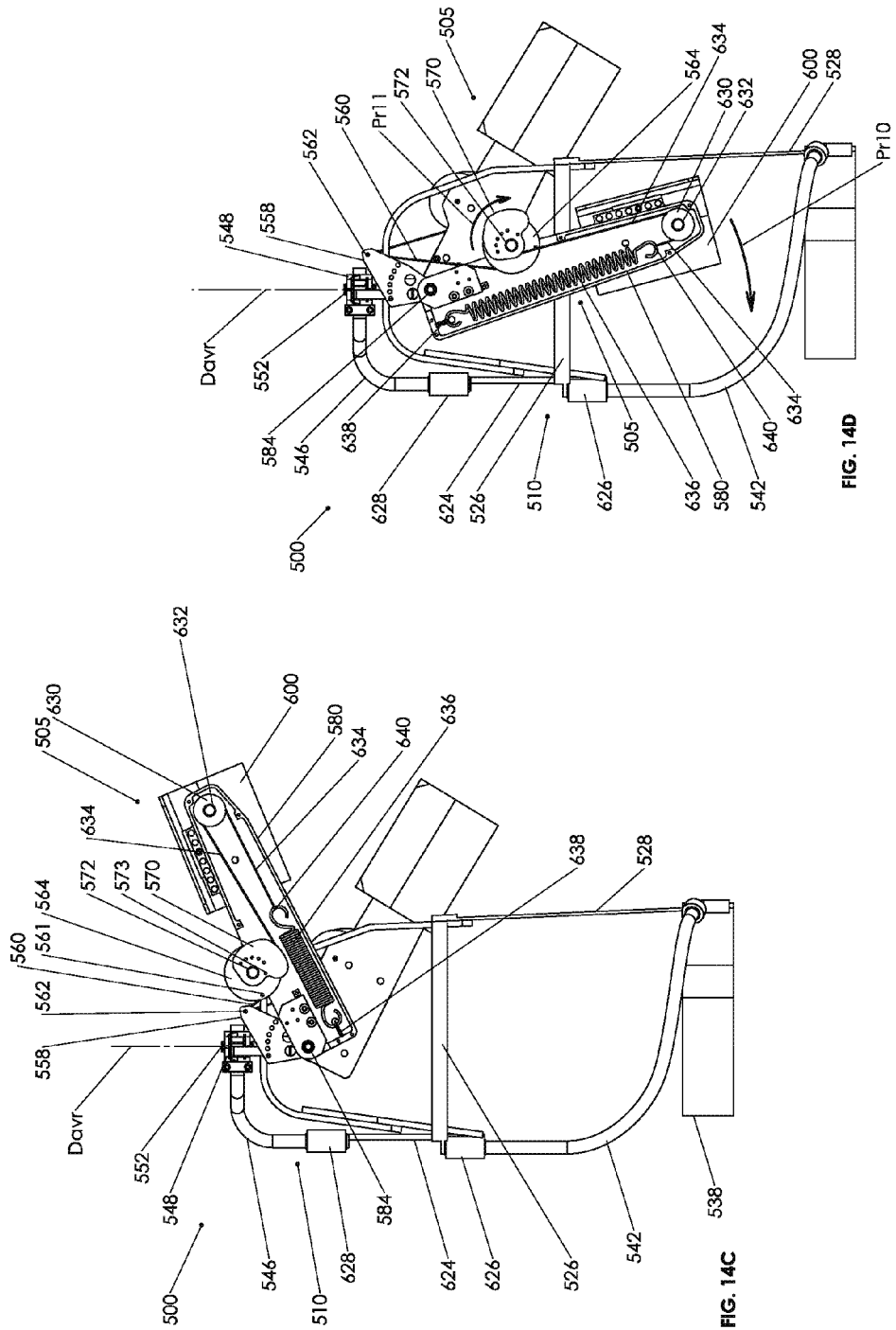

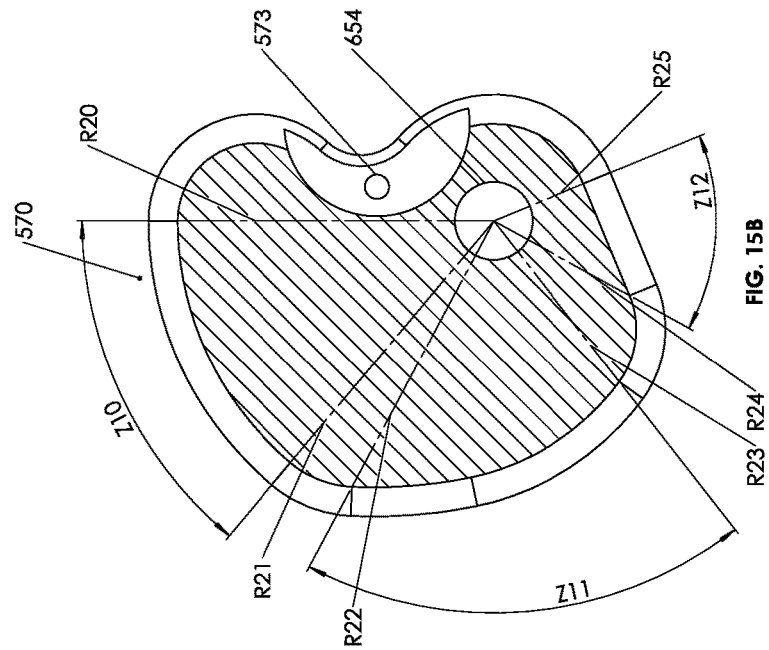
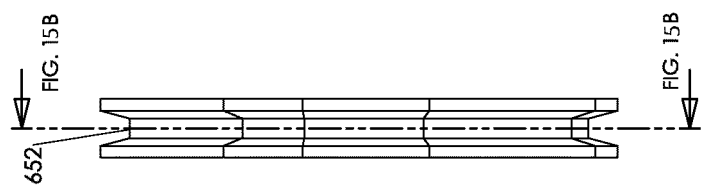
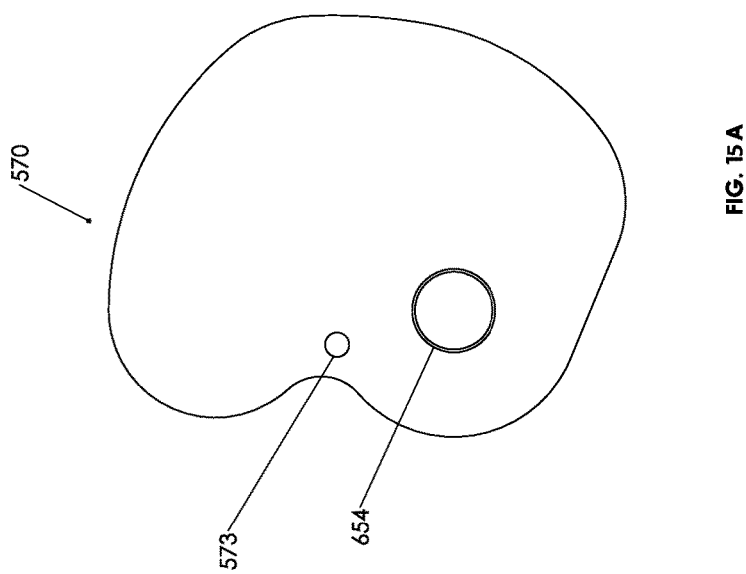
FIG. 15B
FIG. 15A

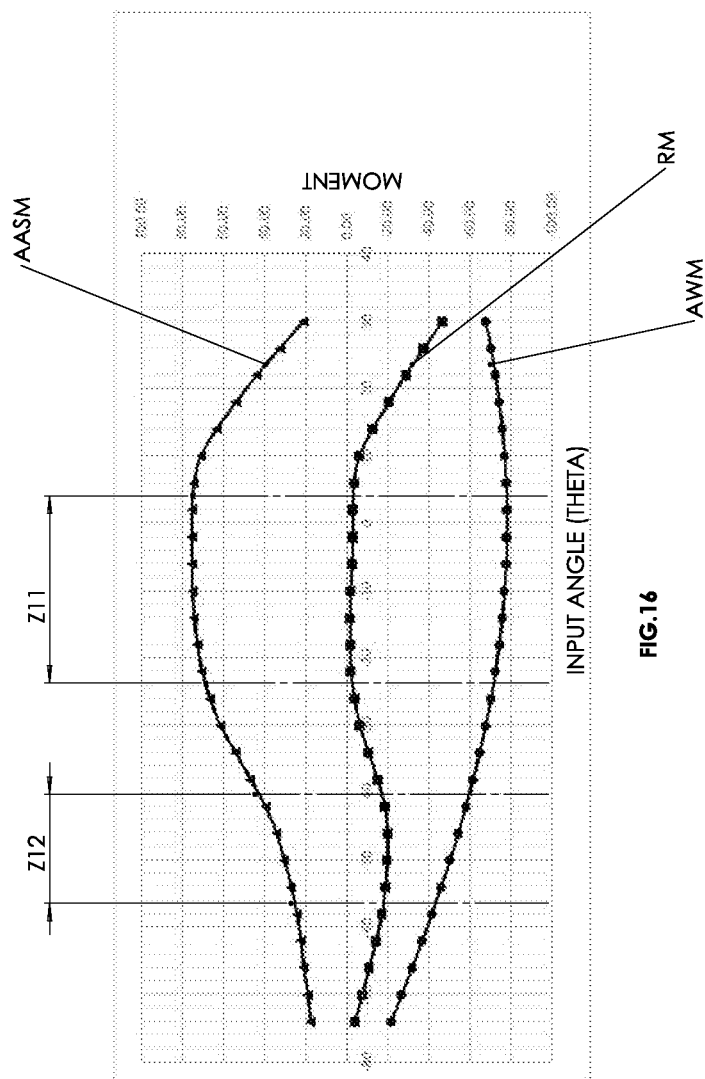

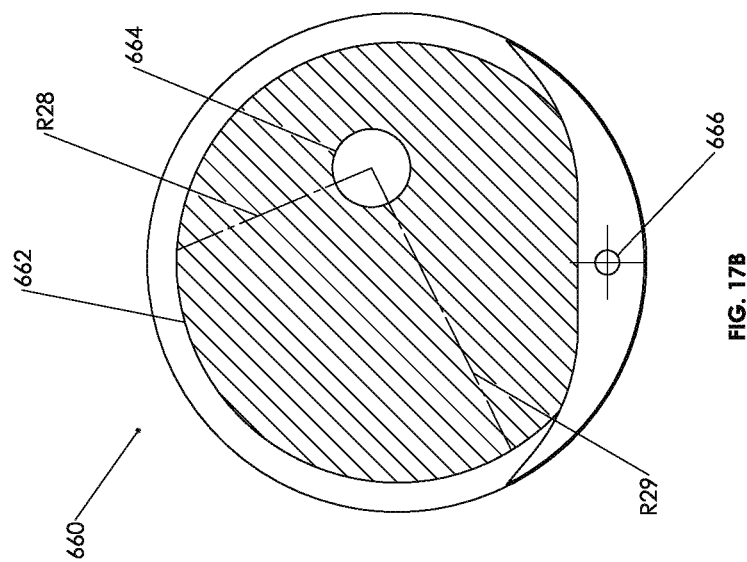
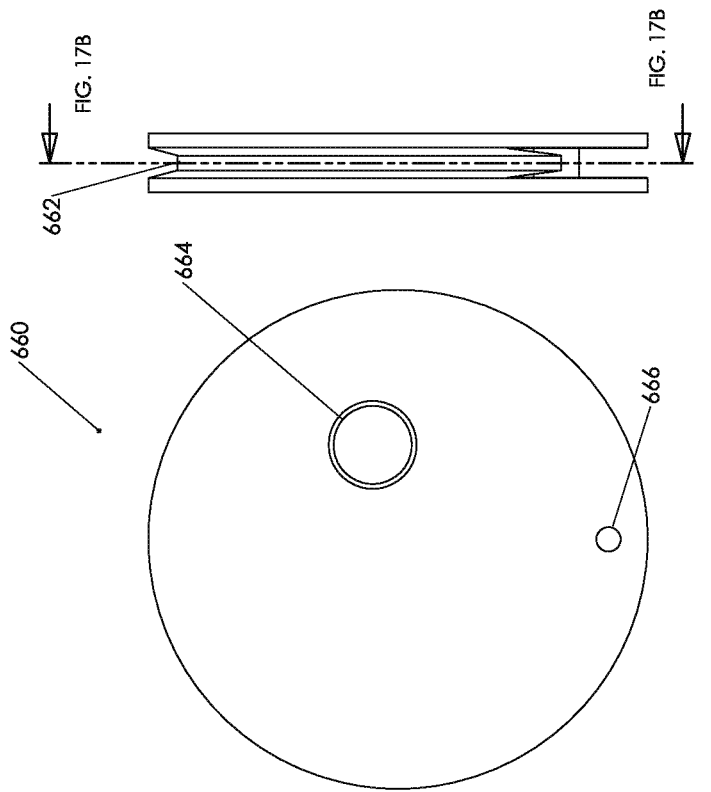
FIG. 17B
FIG. 17A

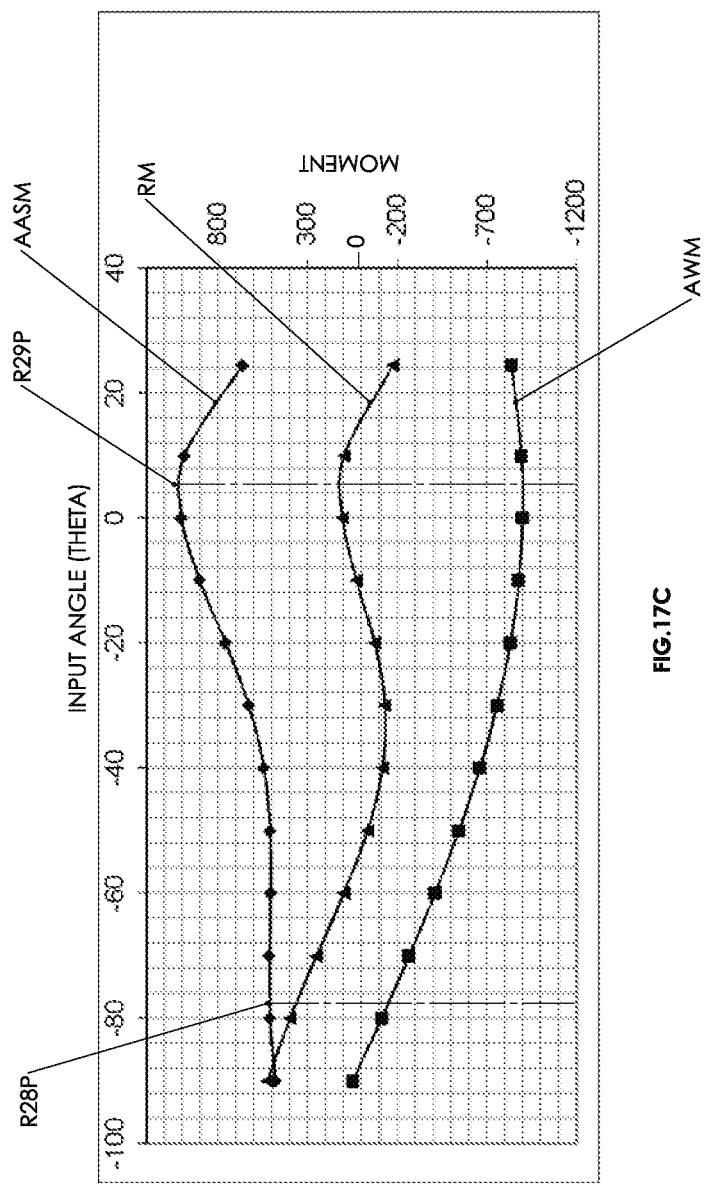

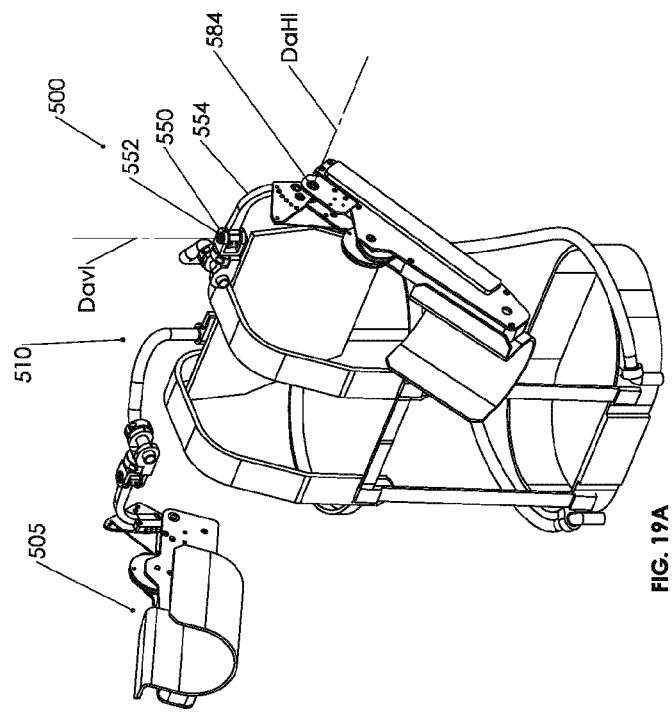
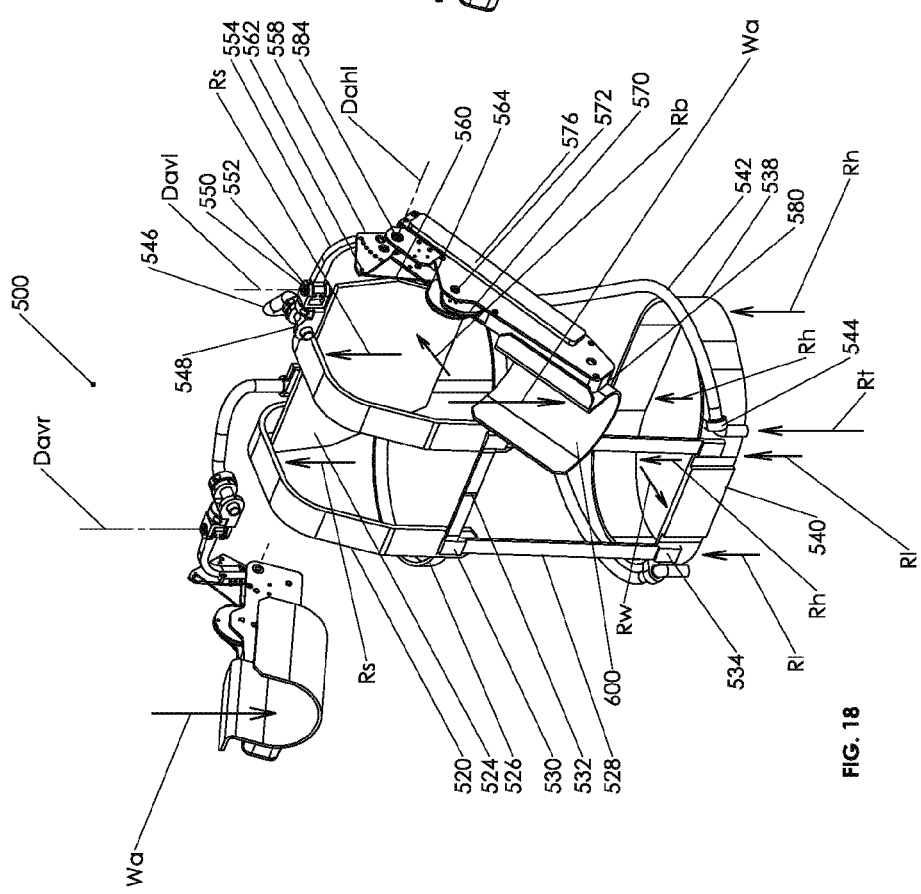

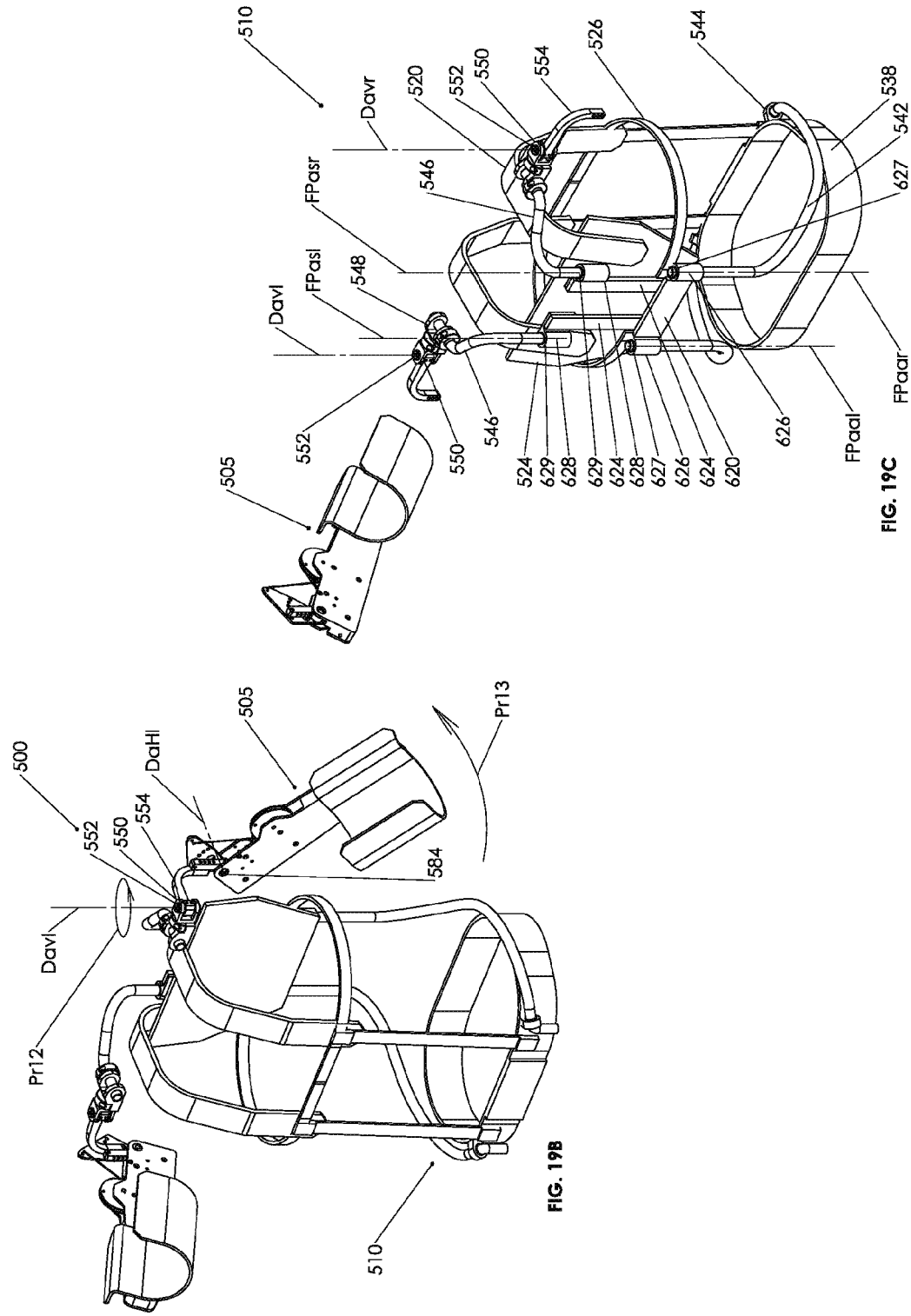

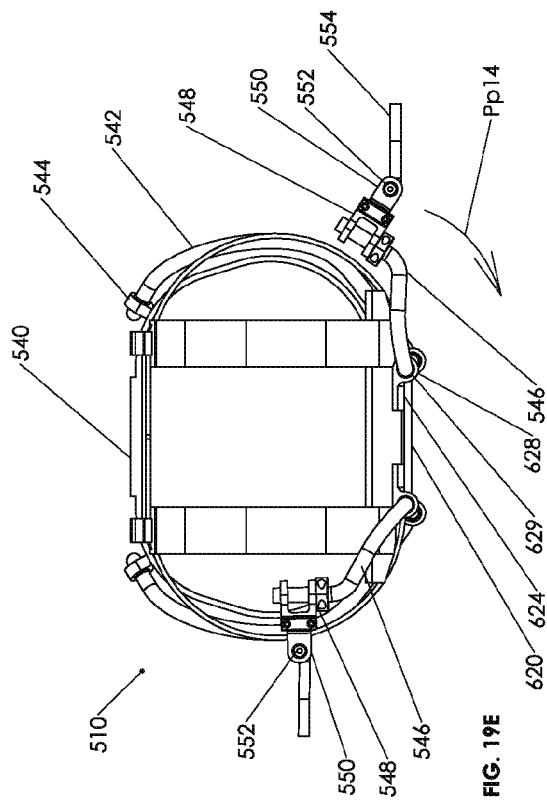
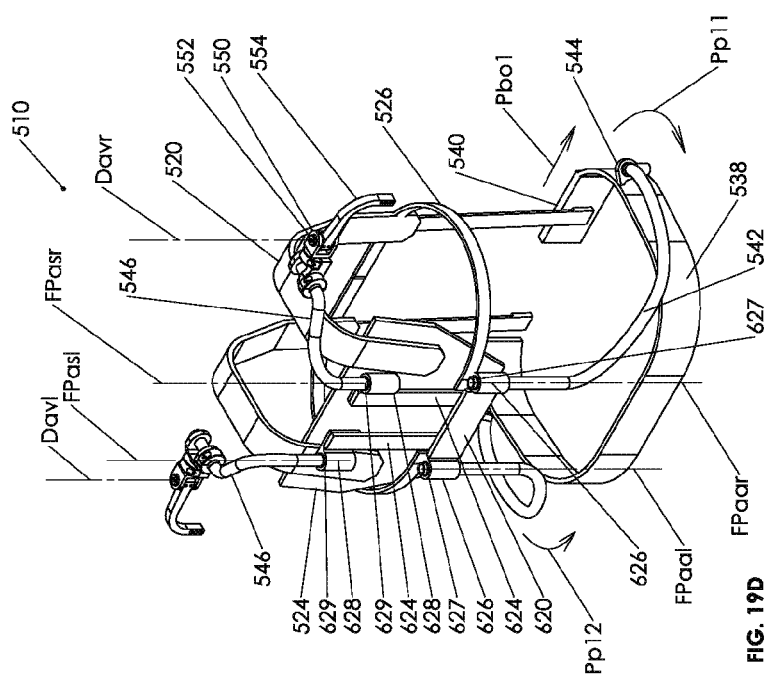
FIG. 19E
FIG. 19D

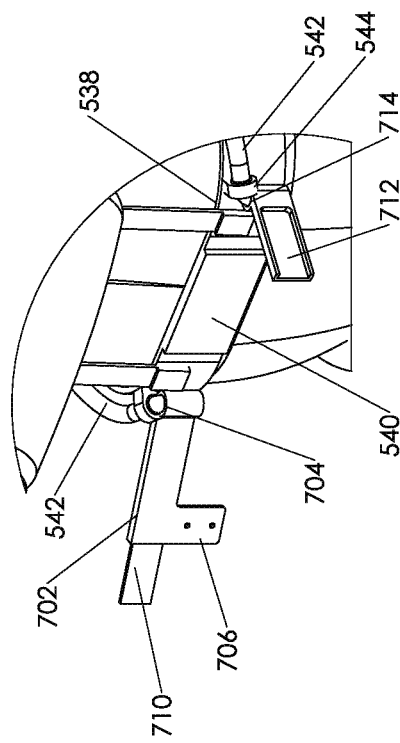
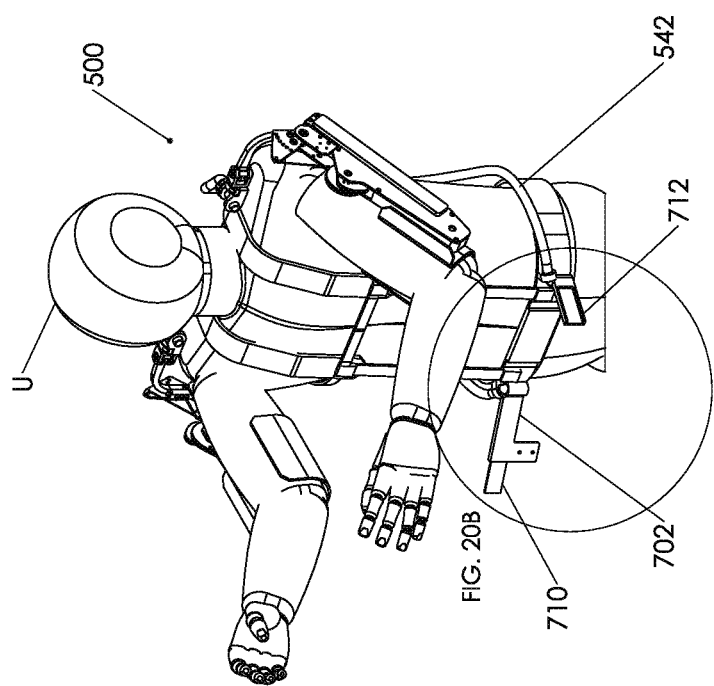
FIG. 20B
FIG. 20A

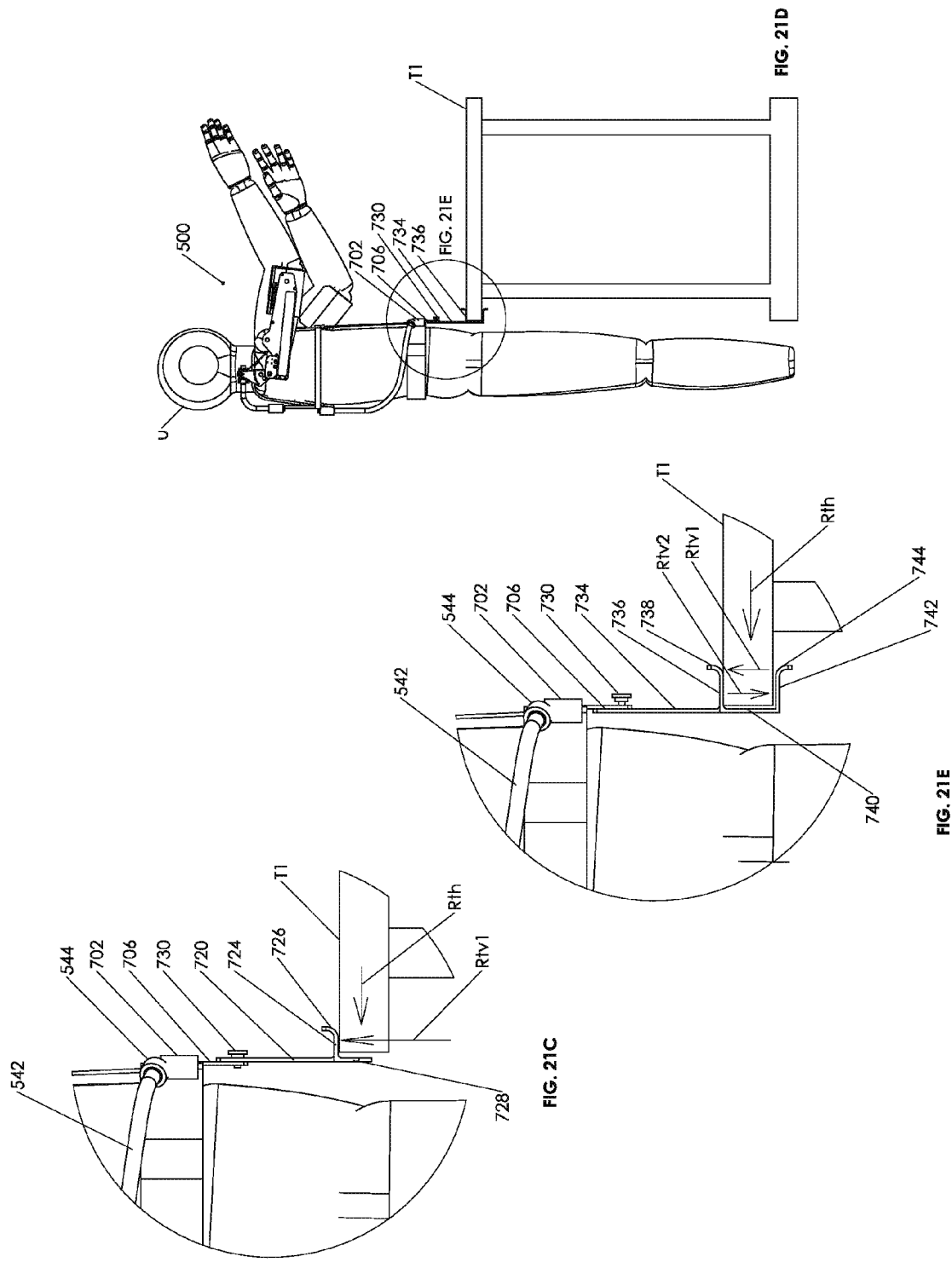

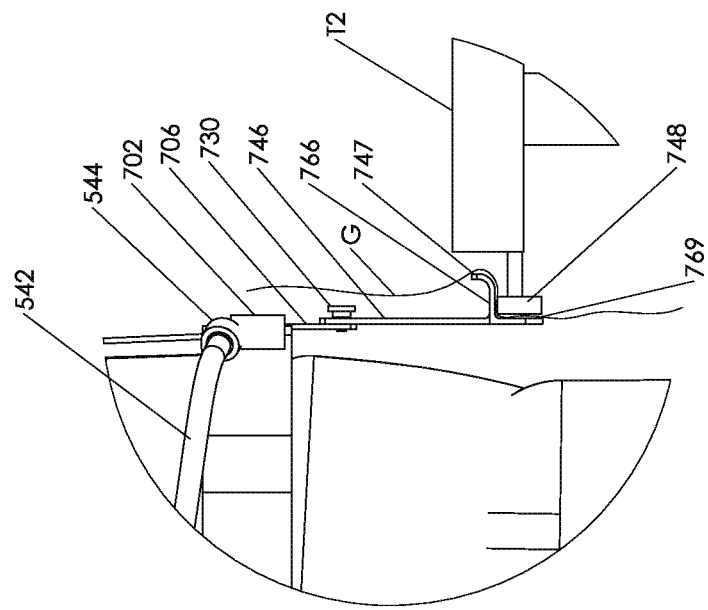
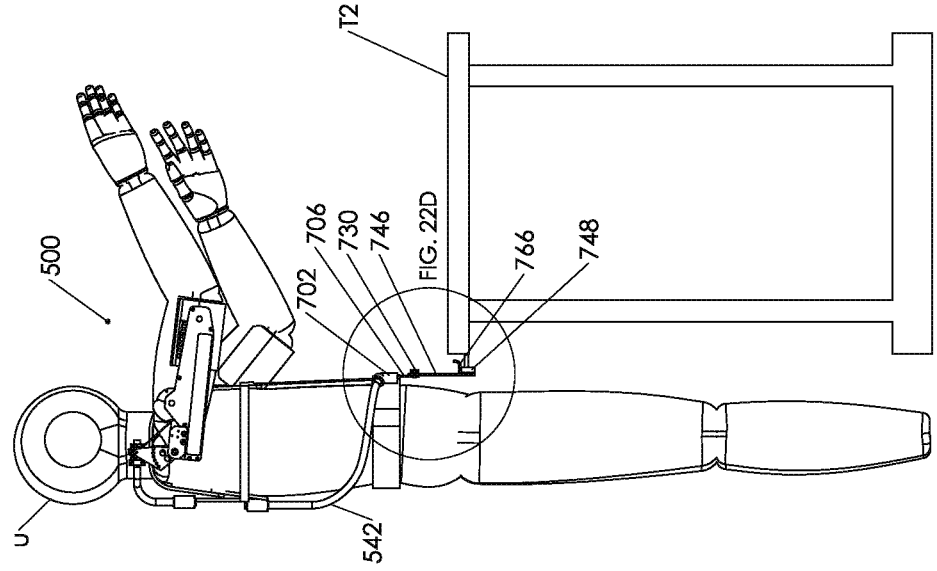
FIG. 22D
FIG. 22C

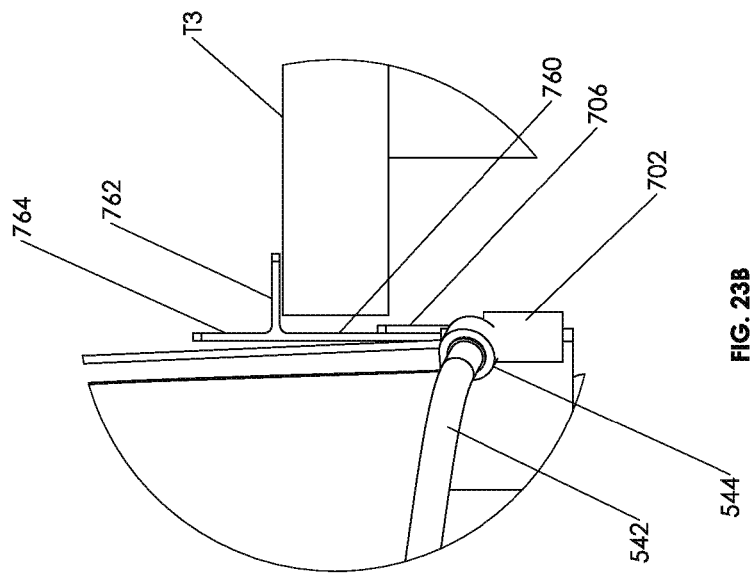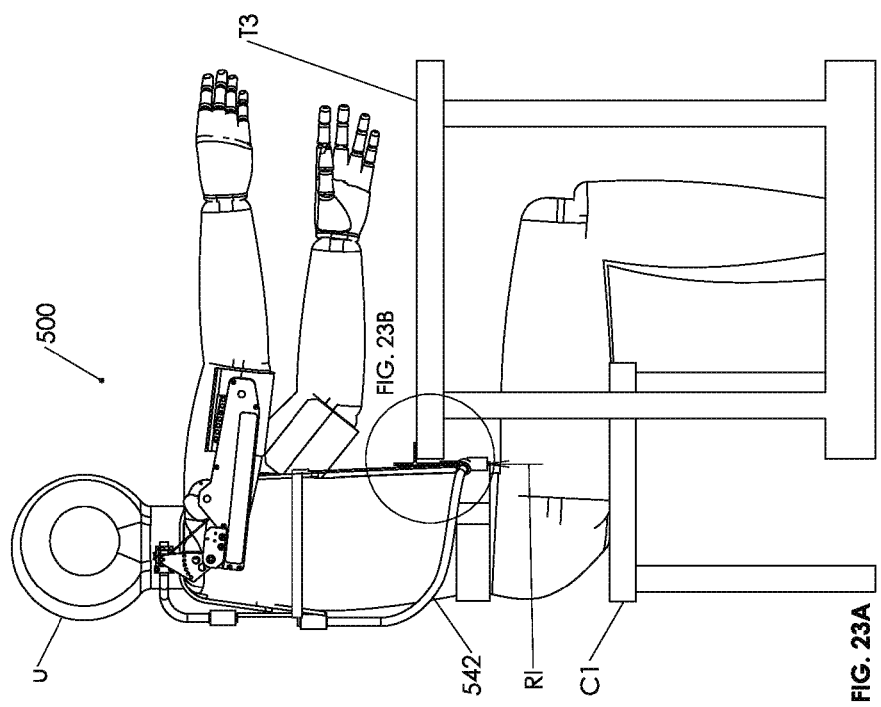

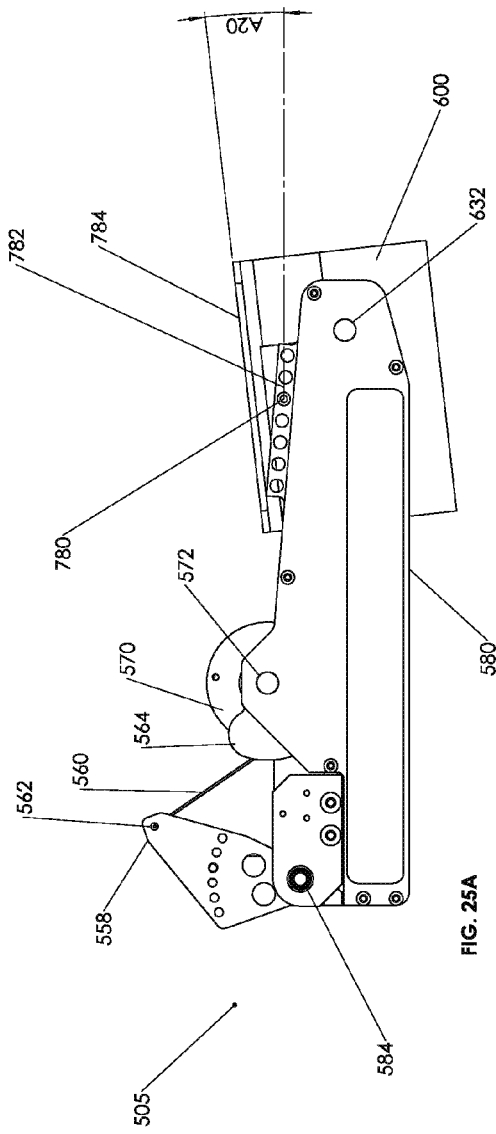
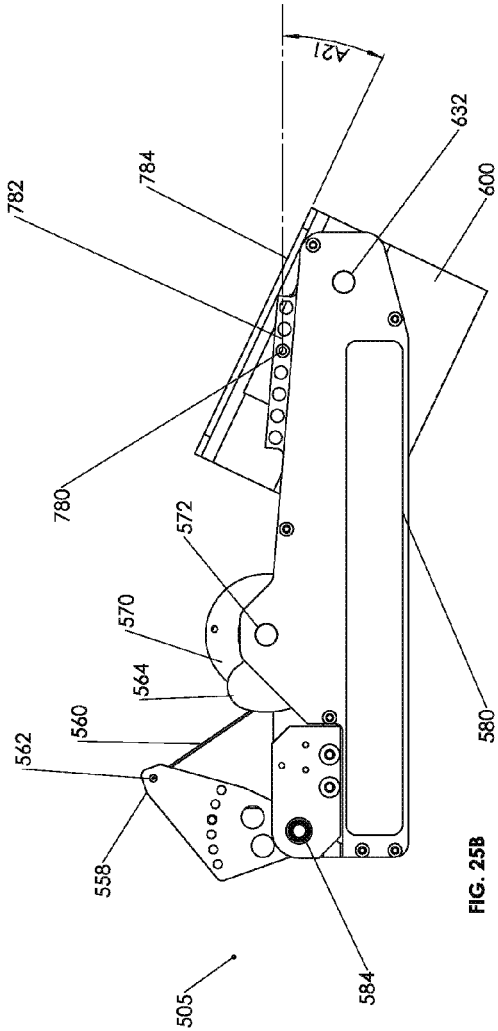
FIG. 25A
FIG. 25B

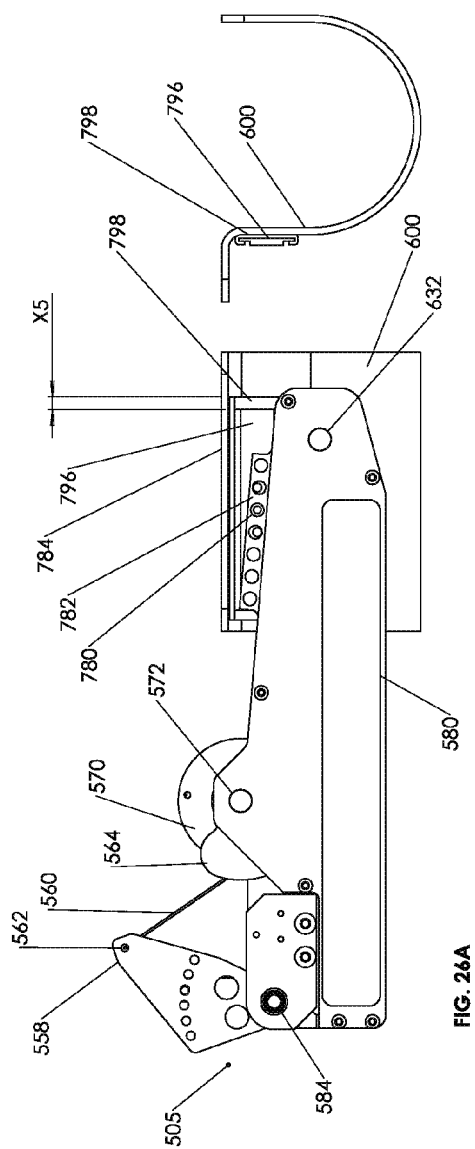
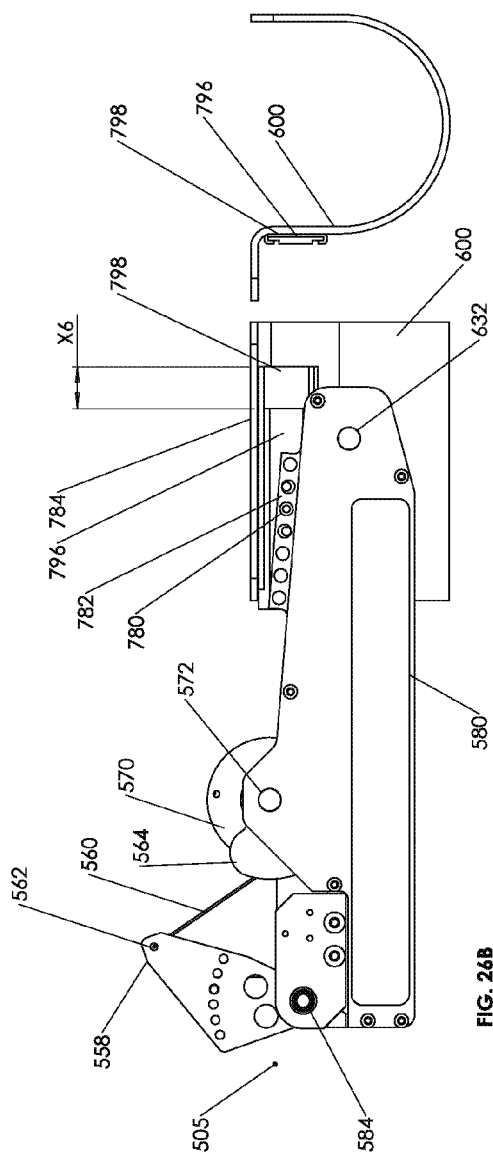
FIG. 26A
FIG. 26B

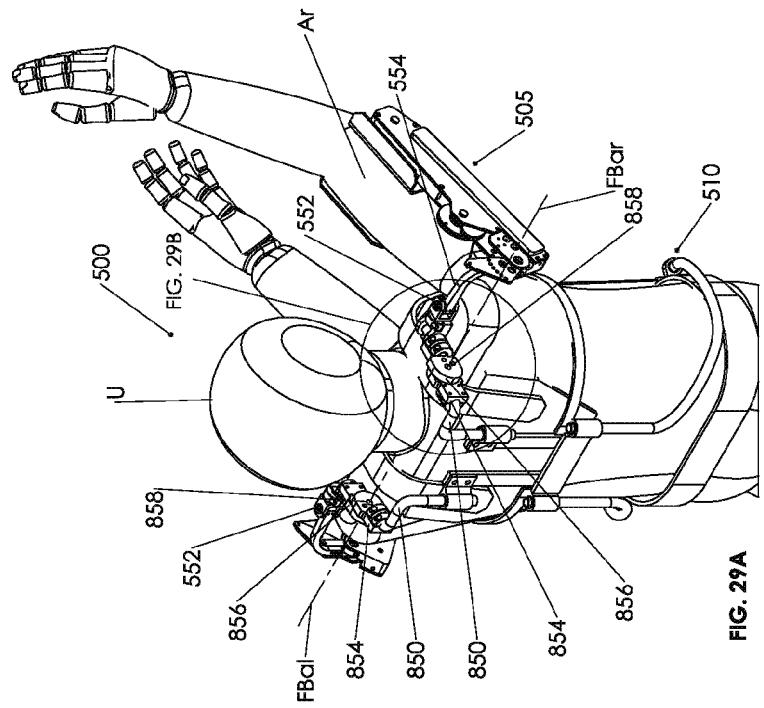
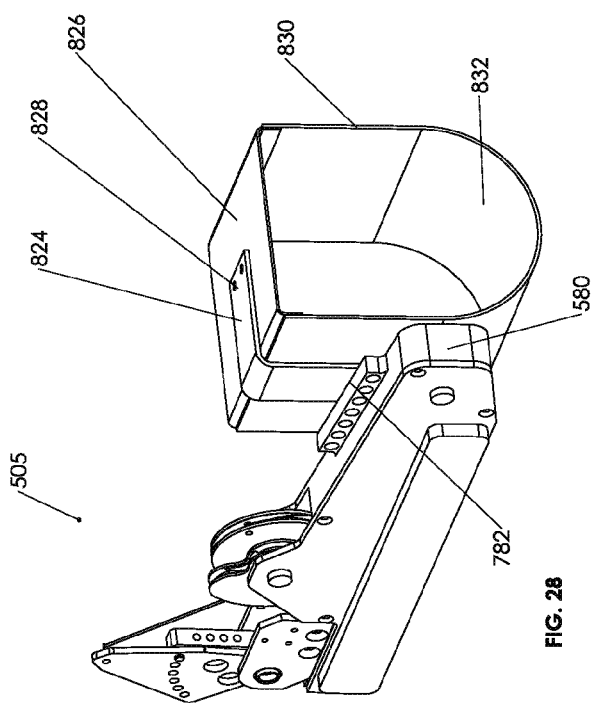
FIG. 29A
FIG. 28

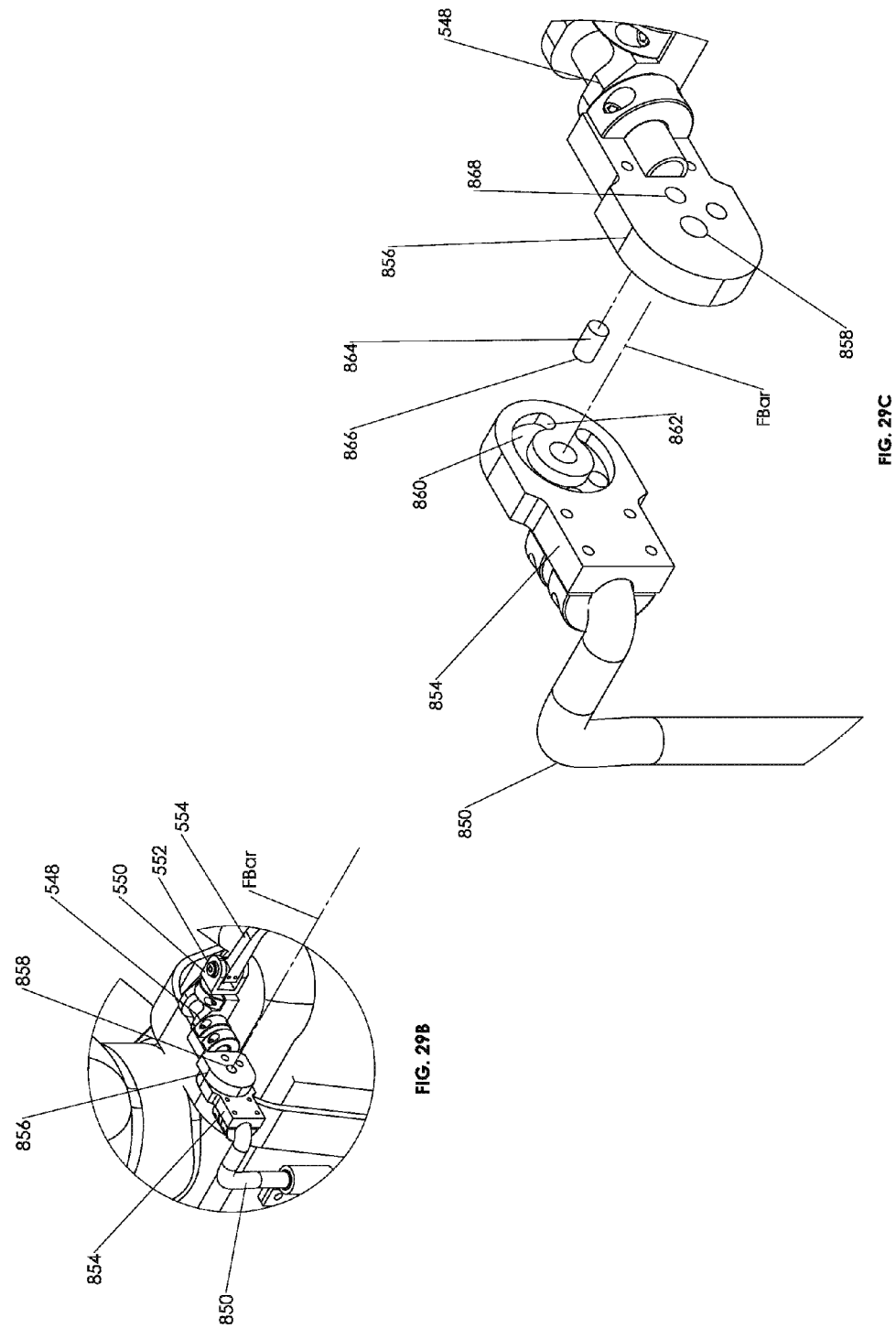

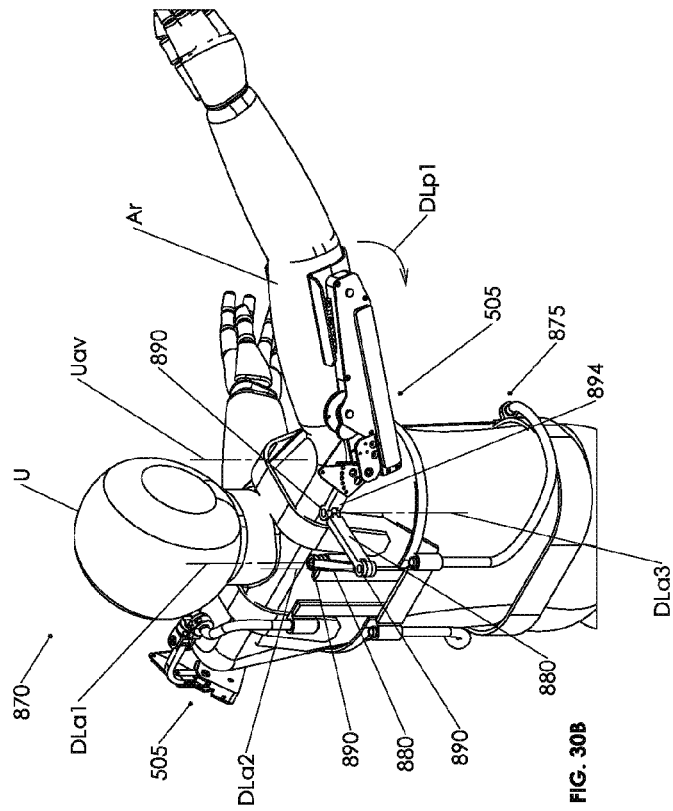
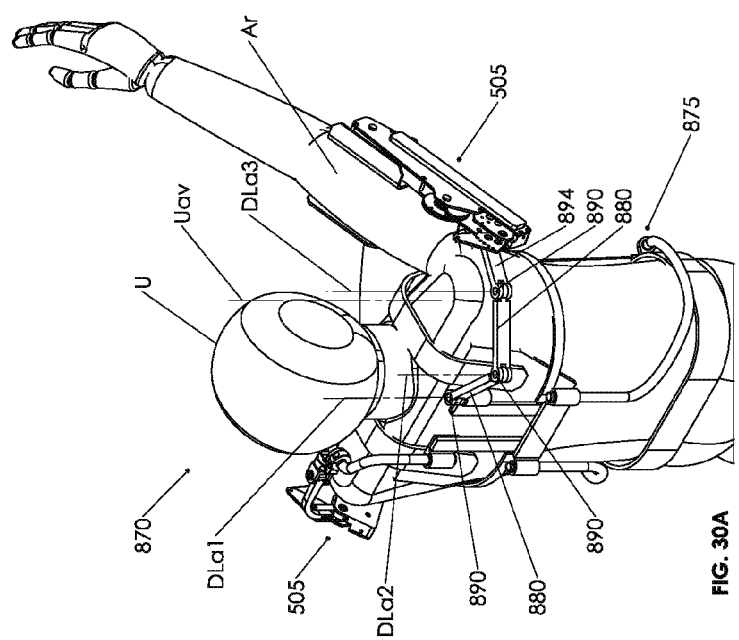
FIG. 30A
FIG. 30B

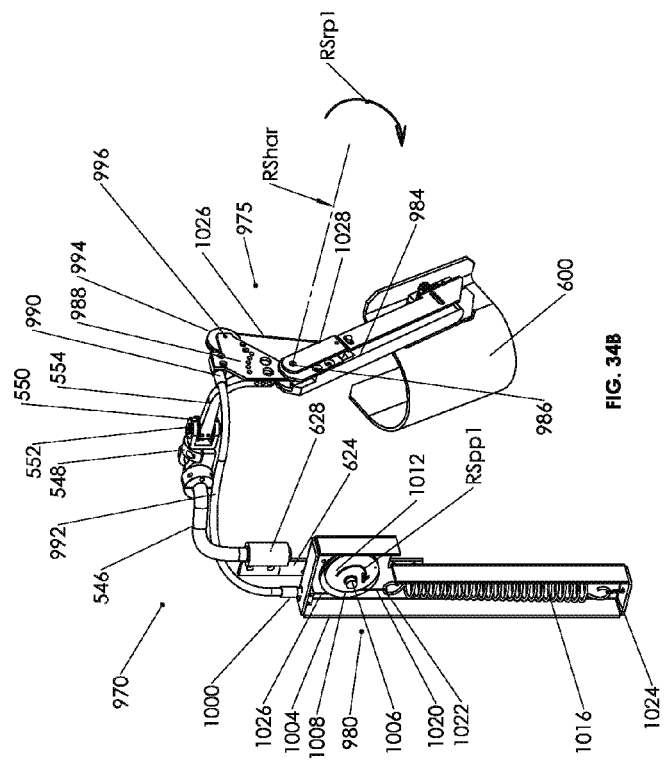
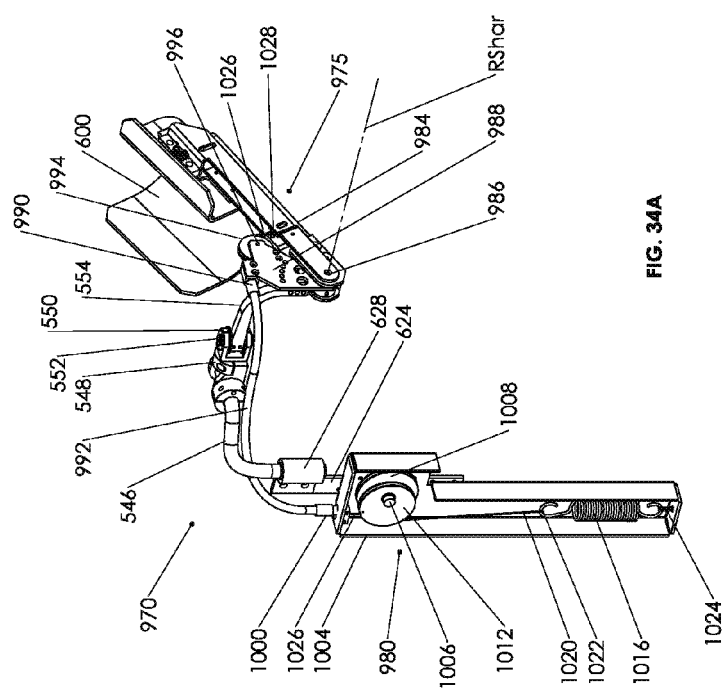
FIG. 34B
FIG. 34A

ADAPTIVE ARM SUPPORT SYSTEMS AND METHODS FOR USE

RELATED APPLICATION DATA

This application claims benefit of provisional application Ser. No. 61/735,894, filed Dec. 11, 2012, and 61/879,088, filed Sep. 17, 2013. The application is also related to Ser. Nos. 13/563,728 and 13/353,268, filed Jan. 18, 2012. The entire disclosures of these applications are expressly incorporated by reference herein.

FIELD OF THE INVENTION

The present invention relates to systems, devices, and methods for supporting a user's arms, for example, to adaptive arm support systems that support one or both of a user's arms, while allowing substantially free motion, e.g., to allow the user to perform one or more tasks for extended periods of time with one or both arms extended.

BACKGROUND

Numerous tasks require people to work with their arms outstretched. Examples include surgery, dentistry, painting, dishwashing, and product assembly. Persons engaged in such activities may experience fatigue from prolonged muscular efforts required to resist the force of gravity on their arms in order to keep them extended. Weak or disabled persons may experience fatigue performing daily tasks. Static arm rests on chairs and work tables are only effective if the task is performed within a relatively restricted area, for example, at a computer keyboard. Tasks that involve a greater range of motion are not aided by static armrests.

Thus, there is a need for an adaptive armrest or arm support system that may relieve fatigue experienced by persons performing tasks involving moderate to large ranges of motion.

SUMMARY

The present invention is directed to systems, devices, and methods for supporting a user's arms, for example, to adaptive arm support systems or devices that support one or both of a user's arms, while allowing substantially free motion, e.g., to allow the user to perform one or more tasks for extended periods of time with one or both arms extended.

In accordance with one embodiment, a system is provided for supporting an arm of a user that includes a harness configured to be worn on a body of a user; an arm support coupled to the harness configured to support an arm of the user, the arm support configured to accommodate movement of the arm while following the movement without substantially interfering with the movement of the user's arm; and one or more compensation elements coupled to the arm support to apply an offset force to at least partially offset a gravitational force acting on the arm as the user moves and the arm support follows the movement of the user's arm, the one or more compensation elements providing a force profile that varies the offset force based on an orientation of the arm support.

In an exemplary embodiment, the arm support may include an arm bracket including an arm rest on a first end thereof, and a second end pivotally coupled to the harness such that the arm bracket is pivotable about multiple axes relative to the harness. The one or more compensation elements may include one or more elements, e.g., a resilient element, mounted on the arm bracket.

In addition or alternatively, the arm support may include a first arm support segment pivotally coupled to the harness about a first vertical axis such that the first arm support segment is rotatable substantially horizontally about the first vertical axis relative to the harness; and a second arm support segment pivotally coupled to the first arm support segment such that the second arm support segment is rotatable about a second axis generally orthogonal to the first vertical axis. Optionally, the second arm support segment may include an arm rest configured to support a portion of an arm of the user and/or a resilient element mounted on the second arm support segment.

In accordance with another embodiment, a system is provided for supporting an arm of a user that includes a harness configured to be worn on a body of a user; an arm support coupled to the harness configured to support an arm of the user, the arm support comprising an arm bracket including an arm rest on a first end thereof, and a second end pivotally coupled to the harness such that the arm bracket is pivotable about multiple axes to accommodate movement of the user's arm while following the movement without substantially interfering with the movement of the user's arm; and one or more compensation elements mounted on the arm bracket to at least partially offset a gravitational force acting on the user's arm as the user moves and the arm bracket follows the movement of the user's arm. Optionally, the arm support may include a hinge bracket pivotally coupled to the harness about a first vertical axis such that the hinge bracket is rotatable substantially horizontally about the first vertical axis relative to the harness, and wherein the second end of the arm bracket is pivotally coupled to the hinge bracket such that the arm bracket is rotatable about a second axis generally orthogonal to the first vertical axis.

In accordance with still another embodiment, a system is provided for supporting an arm of a user that includes a harness configured to be worn on a body of a user, the harness comprising a shoulder harness configured to be worn over or around one or both shoulders of the user, an abdomen belt configured to be worn around the waist or hips of the user, and one or more support members extending between the shoulder harness and the abdomen belt; an arm support coupled to the harness configured to support an arm of the user, the arm support configured to accommodate movement of the arm while following the movement without substantially interfering with the movement of the user's arm; one or more compensation elements mounted on the arm bracket to at least partially offset a gravitational force acting on the user's arm as the user moves and the arm bracket follows the movement of the user's arm; and a load transfer bracket coupled to the abdomen belt for engaging an external structure to transfer forces from the system to the external structure.

In accordance with yet another embodiment, a system is provided for supporting an arm of a user that includes a harness configured to be worn on a body of a user, the harness comprising a shoulder harness configured to be worn over or around one or both shoulders of the user, an abdomen belt configured to be worn around the waist or hips of the user, and one or more support members extending between the shoulder harness and the abdomen belt; and a head rest, e.g., a chin rest and/or a forehead rest on the harness. Optionally, the system may also include an arm support coupled to the harness configured to support an arm of the user, the arm support configured to accommodate movement of the arm while following the movement without substantially interfering with the movement of the user's arm; and one or more compensation elements mounted on the arm bracket to at least partially offset a gravitational force acting on the user's arm as the user moves and the arm bracket follows the movement of the user's arm. The one or more compensation elements may be configured to provide a force profile that varies the offset force based on an orientation of the arm support.

In accordance with another embodiment, a method is provided for supporting an arm of a user during one or more tasks that includes placing a harness on the user, the harness comprising an arm support movable relative to the harness and including an arm rest; supporting a portion of the user's arm using the arm support such that the arm support subsequently follows movement of the user's arm; and performing one or more tasks involving movement of the user's arm, the arm support comprising one or more compensation elements that apply an offset force to at least partially offset a gravitational force acting on the arm as the user moves without substantially interfering in the movement, the one or more compensation elements providing a force profile that varies the offset force based on an orientation of the arm support.

In an exemplary embodiments, the arm support may include a first arm support segment pivotally coupled to the harness, and performing one or more tasks may include rotating the user's arm substantially horizontally, the first arm support segment rotating freely about a first vertical axis relative to the harness to follow movement of the user's arm. The arm support may also include a second arm support segment pivotally coupled to the first arm support segment, and performing one or more tasks may include lifting and lowering the user's arm, the second arm support segment rotating about a second axis generally orthogonal to the first vertical axis to follow movement of the user's arm.

In accordance with still another embodiment, a method is provided for supporting an arm of a user during one or more tasks that includes placing a harness on the user, the harness comprising an arm support movable relative to the harness and including an arm rest; securing an abdomen belt of the harness around the user's waist or hips; engaging a load transfer bracket on the abdomen belt with an external structure; supporting a portion of the user's arm using the arm rest such that the arm support subsequently follows movement of the user's arm; and performing one or more tasks involving movement of the user's arm, the arm support comprising one or more compensation elements that apply an offset force to at least partially offset a gravitational force acting on the arm as the user moves without substantially interfering in the movement, the load transfer bracket transferring forces from the harness to the external structure.

In accordance with yet another embodiment, a system is provided for supporting a head of a user that includes a harness configured to be worn on a body of a user, the harness comprising a shoulder harness configured to be worn over or around one or both shoulders of the user, an abdomen belt configured to be worn around the waist or hips of the user; and a head rest comprising a support bracket comprising a first end mounted to the harness and a second end disposed adjacent a forehead of a user when the harness is worn by the user, and a rest member coupled to the second end of the support bracket such that the rest member extends across a forehead of the user when the harness is worn for supporting the user's forehead. Optionally, the system may also include a chin rest mounted to the harness at a location such that the chin rest extends across a chin of the user when the harness is worn for supporting the user's chin. If desired, the support bracket may be adjustable such that the rest member is movable to a location extending across a chin of the user when the harness is worn for supporting the user's chin and/or may be removable.

In accordance with still another embodiment, a system is provided for supporting an arm of a user that includes a harness configured to be worn on a body of a user, the harness comprising a shoulder harness configured to be worn over or around one or both shoulders and on a back of the user, an abdomen belt configured to be worn around the waist or hips of the user, one or more support members extending between the shoulder harness and the abdomen belt, and a shoulder support member including a first end substantially fixed to the shoulder harness at a location behind the back of the user and a second end substantially fixed above the shoulder of the user; an arm support coupled to the harness configured to support an arm of the user, the arm support configured to accommodate movement of the arm while following the movement without substantially interfering with the movement of the user's arm, the arm support comprising: a first arm support segment pivotally coupled to the second end of the shoulder support member such that the first arm support segment is rotatable substantially horizontally about a first vertical axis relative to the shoulder support member; a second arm support segment pivotally coupled to the first arm support segment such that the second arm support segment is rotatable about a second axis generally orthogonal to the first vertical axis; and one or more compensation elements to at least partially offset a gravitational force acting on the user's arm as the user moves and the arm bracket follows the movement of the user's arm.

In any of the embodiments herein, an arm rest may be provided on the arm rest, e.g., on the second arm support segment, shaped to receive an arm of the user. Optionally, the arm rest may be pivotable relative to the second arm support segment and/or the arm rest may be movable along a longitudinal axis of the second arm support segment to adjust an axial position of the arm rest. Optionally, a forearm support may be provided, e.g., pivotally coupled to the second arm support segment, for supporting a forearm of the user.

In accordance with another embodiment, a system is provided for supporting an arm of a user that includes a harness configured to be worn on a body of a user; an arm support coupled to the harness configured to support an arm of the user, the arm support configured to accommodate movement of the arm while following the movement without substantially interfering with the movement of the user's arm; and one or more compensation elements coupled to the arm support to apply an offset force to at least partially offset a gravitational force acting on the arm as the user moves the arm and the arm support follows the movement of the user's arm, the one or more compensation elements comprising a resilient element mounted on the harness within a resilient element housing at a location adjacent the user's back when the harness is worn by the user and a cable coupled between the resilient element and the arm support.

In accordance with still another embodiment, a method is provided for supporting a user during one or more tasks that includes placing a harness on the user, the harness comprising a head support extending in front of the user's head without substantially obstructing the user's vision; contacting a portion of the user's head, e.g., the user's forehead and/or chin, using a head rest of the head support; and performing one or more tasks, the head rest supporting the user's head during performance of the one or more tasks.

Optionally, the harness may also include an arm support movable relative to the harness and including an arm rest, and the method may further include supporting a portion of the user's arm using the arm support such that the arm support subsequently follows movement of the user's arm; and performing one or more tasks involving movement of the user's arm, the arm support comprising one or more compensation elements that apply an offset force to at least partially offset a gravitational force acting on the arm as the user moves without substantially interfering in the movement, the one or more compensation elements providing a force profile that varies the offset force based on an orientation of the arm support.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIG. 1 is a rear perspective view of the upper body of a user working with an outstretched right arm.

FIG. 2 is a front perspective view of an exemplary embodiment of an adaptive arm support system that may be worn by a user, such as the user of FIG. 1.

FIG. 3A is a rear perspective views of the adaptive arm support system of FIG. 2 worn by a user and supporting the user's extended arm. FIG. A is a detail of the system of FIG. 3A.

FIG. 4A is a side view of the adaptive arm support system of FIG. 2.

FIGS. 4B and 4C are schematics of elements of the adaptive arm support system of FIG. 2, showing load vectors as the system is moved vertically.

FIGS. 5A-5E are rear perspective views of the adaptive arm support system of FIG. 2 worn by a user, showing a sequence of positions of the user's supported arm used to park the system. FIGS. B-D are details of the system shown in FIGS. 5C-5E, respectively.

FIGS. 6A and 6B are rear perspective views of another exemplary embodiment of an adaptive arm support system worn by a user and supporting the user's extended arm as the user moves the supported arm vertically. FIGS. E and F are details of the system of FIGS. 6A and 6B, respectively.

FIGS. 7A and 7B are side views of yet another exemplary embodiment of an adaptive arm support system with an arm rest of the system moving vertically.

FIGS. 8A and 8B are side views of still another exemplary embodiment of an adaptive arm support system with an arm rest of the system moving vertically.

FIGS. 11A and 11B are front perspective views of the adaptive arm support system of FIG. 2 with a support post of the system rotating about a horizontal axis.

FIGS. 12A and 12B are rear perspective views of yet another embodiment of an adaptive arm support system with an arm rest of the system moving vertically. FIGS. G and H are details of the system shown in FIGS. 12A and 12B, respectively.

FIGS. 13A and 13B are front and rear perspective views, respectively, of another embodiment of an adaptive arm support system being worn by a user that supports both of the user's arms.

FIGS. 14A and 14B are front and rear perspective views, respectively, of the adaptive arm support system of FIGS. 13A and 13B.

FIGS. 14C and 14D are side views of the adaptive arm support system of FIGS. 13A and 13B with a cover removed to show internal components of a biasing mechanism for the system.

FIG. 15 is not used.

FIG. 15A includes side and end views of an exemplary embodiment of an asymmetrical secondary pulley for the biasing mechanism shown in FIGS. 14C and 14D.

FIG. 15B is a cross-sectional view of the secondary pulley of FIG. 15A.

FIG. 16 is a graph showing an exemplary moments achieved using the secondary pulley of FIG. 15A in the biasing mechanism of FIGS. 14C and 14D.

FIG. 17A includes side and end views of an alternative exemplary embodiment of an asymmetrical secondary pulley for the biasing mechanism shown in FIGS. 14C and 14D.

FIG. 17B is a cross-sectional view of the secondary pulley of FIG. 17A.

FIG. 17C is a graph showing an exemplary moments achieved using the secondary pulley of FIG. 17A in the biasing mechanism of FIGS. 14C and 14D.

FIG. 18 is a front perspective view of the system of FIGS. 14A and 14B, showing an exemplary arrangement of forces acting on the system during use.

FIGS. 19A and 19B are front perspective views of the system of FIGS. 14A and 14B, showing rotation of an arm support of the system rotated about a vertical axis.

FIGS. 19C and 19D are rear perspective views of the system of FIGS. 14A and 14B with both arm supports removed (one shown separated in FIG. 19C).

FIG. 19E is a top view of the system of FIGS. 14A and 14B showing a shoulder support tube of the system rotated to accommodate rotation of a user's shoulder (not shown).

FIG. 20A is a front perspective view of the system of FIGS. 14A and 14B worn by a user and showing a load transfer bracket of the system in an open position.

FIG. 20B is a detail of the open load transfer bracket of the system shown in FIG. 20A.

FIG. 21C is a detail of the system of FIGS. 21A and 21B showing loads being transferred at least partially to the table from the system via the load transfer bracket.

FIG. 21D is a side view of the system of FIGS. 13A and 13B worn by a user and including an alternative embodiment of a load transfer bracket being at least partially supported by a table.

FIG. 21E is a detail of the system of FIG. 21D showing loads being transferred at least partially to the table from the system via the load transfer bracket.

FIG. 22C is a side view of the system of FIGS. 13A and 13B worn by a user and including yet another alternative embodiment of a load transfer bracket being at least partially supported by a cooperating rail on a table.

FIG. 22D is a detail of the cooperation between the load transfer bracket of the system of FIG. 22C and the rail of the table.

FIG. 23A is a side view of the system of FIGS. 13A and 13B worn by a user and including another alternative embodiment of a load transfer bracket being at least partially supported by a table while the user is seated at the table.

FIG. 23B is a detail of the cooperation between the load transfer bracket of the system of FIG. 23A and the table.

FIGS. 25A and 25B are side views of another embodiment of an arm support assembly that may be included in an adaptive arm support system, which includes a pivoting arm rest.

FIGS. 26A and 26B are side views of yet another embodiment of an arm support assembly that may be included in an adaptive arm support system, which includes an axially translating arm rest.

FIG. 28 is a perspective view of another embodiment of an arm support assembly that may be included in an adaptive arm support system, which includes a sling-style arm rest.

FIG. 29A is a rear perspective view of another exemplary embodiment of an adaptive arm support system including mechanisms for storing arm rests of the system.

FIG. 29B is a detail of components of the storage mechanism of the system of FIG. 29A with the arm rest in an active position.

FIG. 29C is an exploded view of the components of the storage mechanism of FIGS. 29A and 29B.

FIGS. 30A and 30B are rear perspective views of another exemplary embodiment of an adaptive arm support system worn by a user and including an alternative shoulder pivot mechanism.

FIGS. 34A and 34B are perspective views of another exemplary embodiment of an arm support assembly that may included in an adaptive arm support system including a resilient element remote from an arm rest of the system, showing the arm rest raised and lowered.

DESCRIPTION OF THE EXEMPLARY EMBODIMENTS

Figure 3C:
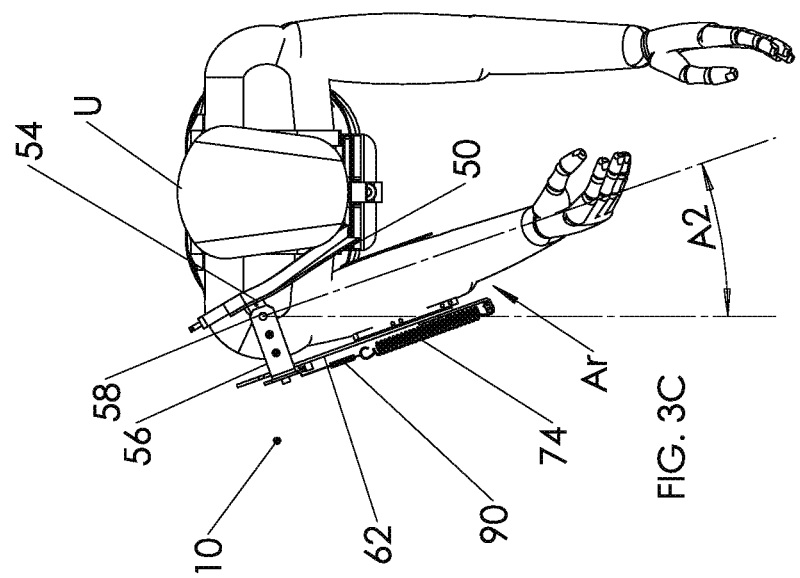
FIGS. 3B and 3C are tops views of the adaptive arm support system of FIG. 2 worn by a user and supporting the user's extended arm as the user moves the supported arm horizontally.

Turning to the drawings, FIG. 1 shows the upper body of a user U working with outstretched right arm Ar, which has a weight Wa. In order to keep the arm Ar raised, the user U must use muscles in the user's back B and shoulder S to counteract arm weight Wa, resulting in fatigue. The user's shoulder S acts as a spherical joint (not shown), permitting motion of the arm Ar in various directions, including rotation about substantially vertical axis Uav and substantially horizontal axis Uah, which intersect approximately at the center of rotation of the shoulder S.

FIG. 2 shows an exemplary embodiment of an adaptive arm support system 10 that may be worn by a user. Generally, the system 10 includes a torso mounted harness, and one or more adaptive arm rests (only one shown) coupled to the harness. The adaptive arm rest is biased with a resilient element to impart a force to the arm of a user, for example, to bear all, or part of, the weight of the arm. The force may vary with arm position or be substantially constant through its range of motion. Pivot axes Day and Dah, about which elements of the adaptive arm rest may pivot, may intersect. When system 10 is worn by user U (e.g., as shown in FIGS. 3A-3E), pivot axes Day and Dah may also be located essentially collinear with the user U's shoulder axes Uav and Uah (shown in FIG. 1), allowing the elements of the mobile arm rest to pivot approximately about the center of the user U's shoulder S. Optionally, the pivot axes Day and Dah may be angled, skewed, or offset, relative to the user U's shoulder axes Uav and Uah.

As shown in FIG. 2, shoulder straps 40 attach to a support plate 38 at optional adjustable buckle 42 (not shown). The shoulder bracket 50 is adjustably joined to the support plate 38, e.g., at point 44. Also joining the support plate 38 is a vertical strut 20, which runs essentially parallel to and generally vertically along the user U's abdomen when worn.

The vertical strut 20 may be rigid or flexible, or a combination of both. Chest strap 46 may join the vertical strut 20 at adjustable buckle 48 (not shown). The vertical strut 20 terminates at optional pivot shaft 22. The pivot shaft 22 may turn within a pivot block 24, enabling rotation about axis Dap. The pivot block 24 is attached to an abdomen plate 26, to which a belt 34 is adjustably attached at optional buckle 36 (not shown). The pivot block 24 may itself rotate about axis Das. A pad 28 may be joined to the abdomen plate 26. An optional hook 30 may also be joined to the abdomen plate 26. The belt 34 may be worn on or above hips H of the user U. The vertical strut 20 is shown in the front of the system 10, but may also be located on the back of the system 10 ("backpack" design).

The shoulder bracket 50 is joined to vertical pivot block 54. The vertical pivot block 54 and hinge bracket 56 cooperate to form vertical pivot 58, which enables rotation of hinge bracket 56 about substantially vertical axis Day, as will be explained further below. Rotation about the vertical pivot 58 may be free (i.e., with minimal or no resistance to movement of the user), limited (e.g., having a predetermined minimal resistance), biased by springs or other energy elements (not shown) to a default position, damped (e.g., to slow sudden movement), and/or restricted by a predetermined friction. The pivot block 54 may itself rotate about other axes (not shown).

The hinge bracket 56 also cooperates with an arm bracket 62 to form pivot 66, enabling vertical rotation of the arm bracket 62 about substantially horizontal axis Dah. Optionally, a damping element (not shown) may be located adjacent the pivot 66, e.g., to limit the rotational speed of the arm bracket 62. Arm rest 94 is attached to the arm bracket 62, and provides a cradle for the upper arm of the user's right arm Ar, while the lower arm remains unsupported. The arm rest 94 may contact the upper arm, elbow, forearm, or any combination thereof of the user U, and generally applies a force to the arm Ar (or contacted portion of the arm Ar). The arm rest 94 may be one or more of substantially rigid, flexible, padded, may include fluid filler, mesh, and/or other suitable construction. An optional strap (not shown) may be provided, e.g., to secure the arm Ar within or to the arm rest 94.

Cable anchor 84 is adjustably joined to the hinge bracket 56, and provides an attachment point 82 for a first end of a cable 70. The cable 70 (and any other cables herein) may include one or more wires, chains, strings, ropes, threads, straps, belts, and/or other filaments formed into an elongate, flexible member and the term "cable" is used herein to include any such variations. The cable 70 wraps partially around a pulley 90 and has a second end joined to one end of a resilient element 74 at connector 78. The other end of the resilient element 74 is attached to the arm bracket 62 at mount 76, which may include one or more features (not shown) for adjusting the location of the attached end of the resilient element 74, e.g., to vary the force the resilient element 74 exerts on the cable 70. The pulley 90 attaches to the arm bracket 62 at pulley pivot point 92, which is offset from the pivot 66 along the length of the arm bracket 62. In exemplary embodiments, the resilient element 74 may be an extension spring, a gas extension spring, an elastic band, linear spring, pressurized cylinder, pneumatic, hydraulic, electric, or other extendable device.

Surfaces are provided to react against the body of the user U. All or a portion of the weight Wa of the user U's right arm Ar is applied to the arm rest 94. The force and moment thus applied to the system 10 is counterbalanced by a combination of one or more of reaction forces Rs (shoulder), Rb (back), Rw (waist), (hips), and Rl (lap). Thus, the weight Wa of the user U's right arm Ar may be transferred to various surfaces of the body of the user U. The user U may adjust the shoulder straps 40, chest strap 46, and/or belt 34 to vary the reaction forces. Other surfaces may also react on the system 10, including the edge of a table or other surface (Rt), as described elsewhere herein. This may serve to reduce the load on the muscles of the back and shoulder normally associated with holding one's arm outstretched.

FIG. 3A shows the system 10 mounted on the upper body of a user U. In this view, the user U is holding right arm Ar outstretched. As shown in detail A, a portion of the right arm Ar, e.g., the upper arm, sits in the arm rest 94, thereby providing support for the right arm Ar. The cable 70, attached to the cable anchor 84 at the attachment point 82 and to the resilient element 74 at the connector 78, acts to apply a force to the arm bracket 62, e.g., to lift the arm bracket 62 upwardly, thereby applying a lifting force to the right arm Ar.

Figure 3B:
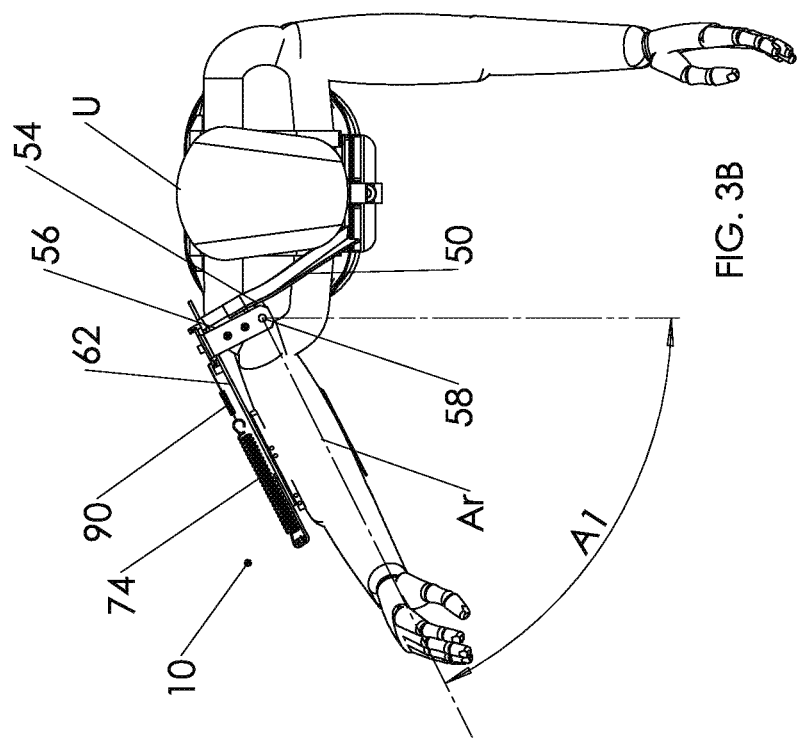

Referring to FIG. 3B (a top view), the user U may move the right arm Ar through a substantially horizontal angle A1, causing the pivot bracket 56 and all attached components to rotate about the vertical pivot 58. FIG. 3C depicts the user U moving the right arm Ar through a different substantially horizontal angle A2, as the pivot bracket 56 and all attached components rotate about the vertical pivot 58.

Figure 3E:
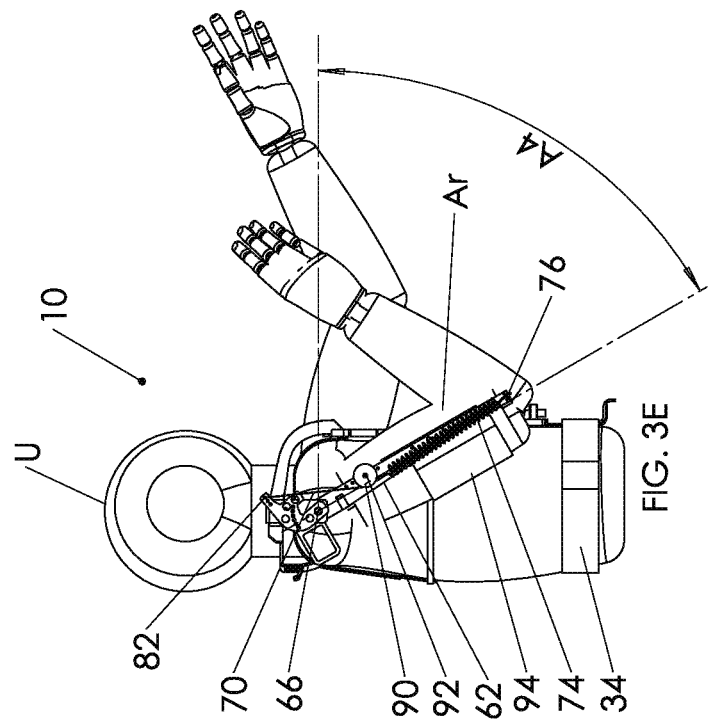
FIGS. 3D and 3E are side views of the adaptive arm support system of FIG. 2 worn by a user and supporting the user's extended arm as the user moves the supported arm vertically.
Figure 3D:
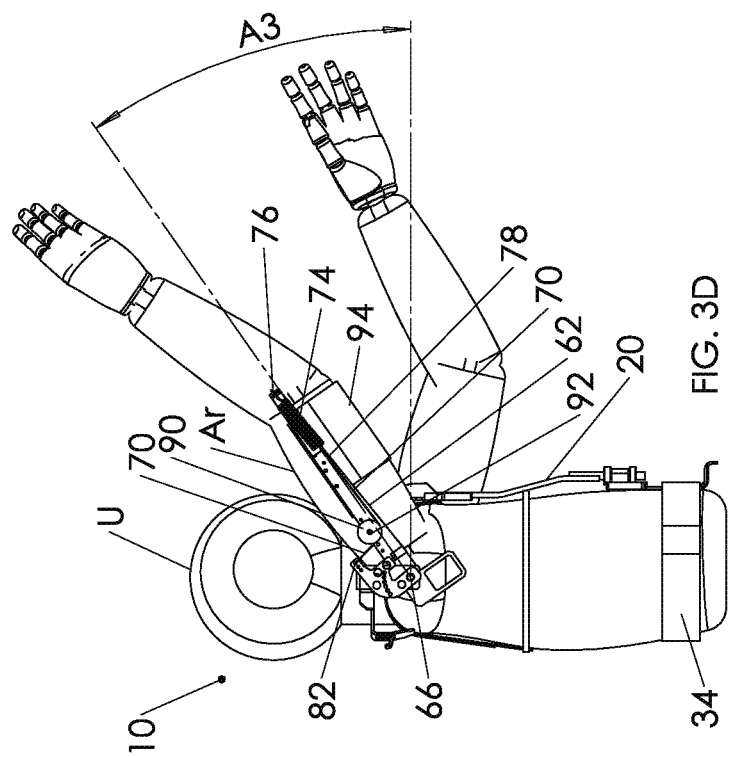

FIG. 3D shows the user U raising the right arm Ar upwardly, through a substantially vertical angle A3. The arm rest 94, pulled upward by the cable 70, transmits a lifting force to the right arm Ar. FIG. 3E depicts the arm Ar moving downward through a different substantially vertical angle A4. The cable 70, attached to the distended resilient element 74, continues to pull the arm rest 94 upwardly to apply an upward force on the right arm Ar.

Thus, as shown in FIGS. 3A-3E, the system 10 permits a full range of motion of the user U's arm Ar, e.g., both vertically and/or horizontally, with the system providing support of the arm Ar without substantially interference or resistance, particularly when the user U moves the arm Ar substantially horizontally.

FIG. 4A shows a side view of the system 10. The weight Wa of the user's arm Ar is applied to the arm rest 94, tending to cause the arm Ar and arm rest 94 to rotate approximately along path Pr1. The Force Fs of the resilient element 74 is transmitted through the cable 70 to the attachment point 82. FIG. 4B, a schematic of a side view of elements of the system 10 (raised above the horizontal by angle A5), shows various relevant forces. Force Fs 1 (the force of the resilient element 74 on the cable 70) acts on the pulley 90, which is pivotably joined to the arm bracket 62. A length L1 of the cable 70 spans the distance between the pulley 90 and the attachment point 82. Force Fs 1 may be broken into perpendicular and parallel components, Fs 1$\|$ and Fs $1^\perp$, respectively. Fs $1^\perp$, acting over center distance x, applies a counterbalancing moment M1 to the arm bracket 62, and consequently the arm rest 94.

FIG. 4C depicts the same elements rotated below horizontal by angle A6. The length of the cable 70 spanning the distance between the pulley 90 and the attachment point 82 has increased to L2, causing resilient element 74 to extend in response. Force Fs 2 (the new force on cable 70 of resilient element 74) may also be broken into components. Fs $2^\perp$, acting over center distance x, applies a counterbalancing moment M2 to the arm bracket 62, and consequently the arm rest 94. Force Fs 2 may be larger than the initial force Fs 1, e.g., due to additional extension of the resilient element 74, but Fs $2^\perp$ is now proportionally smaller than was Fs 1$^{-1}$, thereby reducing the effect of the increased force. This may result in a more uniform force response over the range of motion of the arm bracket 62. Other forms of force management are described elsewhere herein.

FIGS. 5A-5E show a sequence of views of the system 10 and user U, demonstrating a feature of the system 10 allowing the user U to "park" the arm rest 94, for example, store or secure the arm rest 94 behind or otherwise away from the arm Ar, e.g., if arm support is temporarily not required, and allow free movement of the arm Ar. As shown in FIG. 5A, the user U begins to push the arm rest 94 backward, approximately along path Pp1. In FIG. 5B, the arm rest 94 has been pushed further back, along path Pp2, causing rotation about the vertical pivot 58 and the horizontal pivot 66, and bringing loop 86 on the arm bracket 62 closer to a hook 88 mounted on the shoulder bracket 50. Continuing with FIG. 5C, and especially in detail B, the loop 86 is moved over the hook 88. In FIG. 5D, and especially detail C, the user U moves the arm Ar forward along path Pp4, which allows the loop 86 to move approximately along path Pp5, which causes it to interfere with the hook 88 (thereby temporarily attaching it to the shoulder bracket 50). Finally, FIG. 5E (and especially detail D), shows the user U moving the arm Ar approximately along path Pp6, leaving the arm rest 94 "parked," out of the way, on the shoulder bracket 50.

Figure 6A:
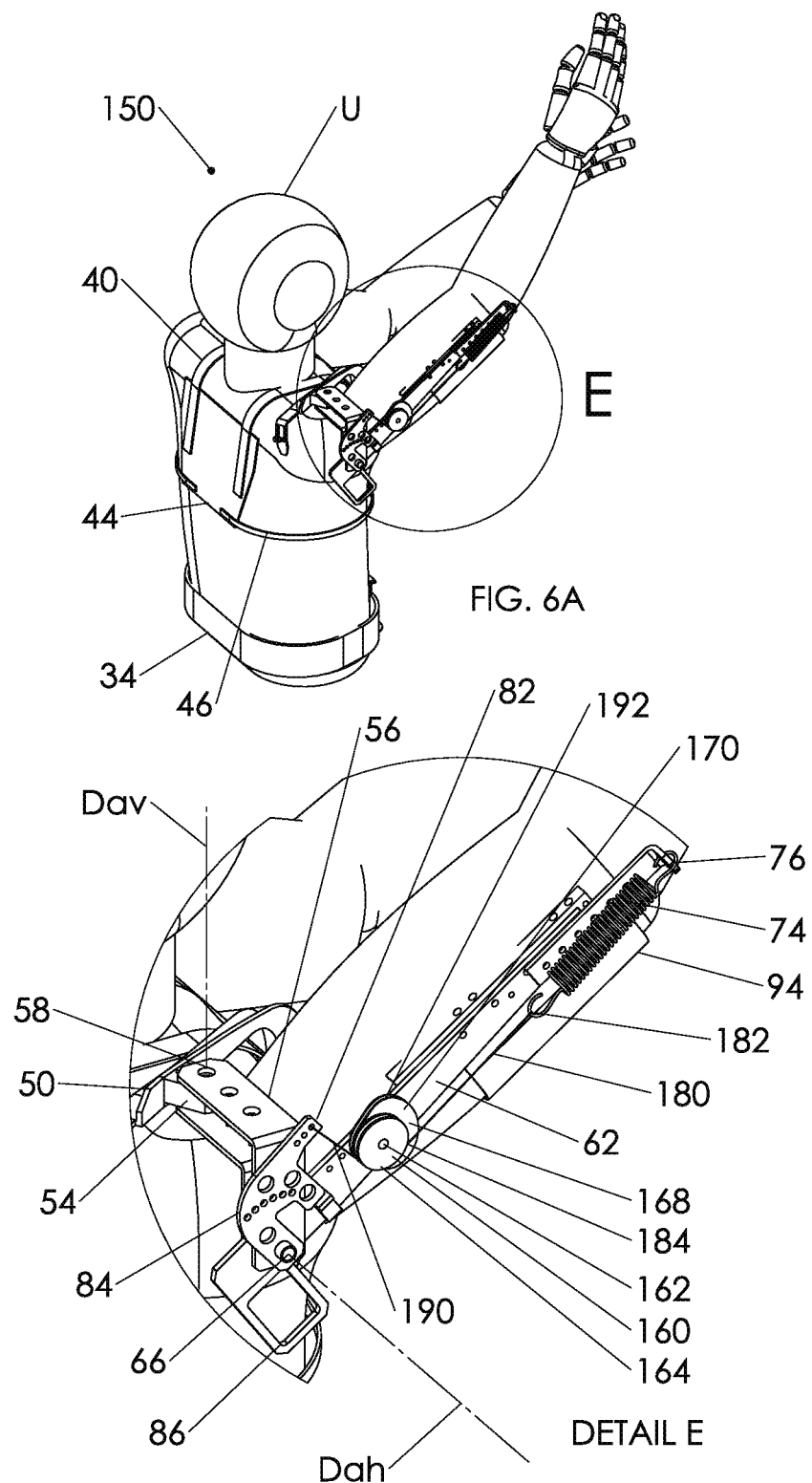

A variant of system 10, employing a different force management apparatus, is shown in FIGS. 6A-6D. Adaptive arm support system 150 generally includes similar components to the system 10 (with similar elements having the same reference number), but employs a dual pulley and cable design to manage forces, e.g., similar to compound bows used in archery. As shown in FIG. 6A, and especially detail E, a dual path pulley 160 is pivotally joined to the arm bracket 62 at pivot 162 (in place of the pulley 90 of FIGS. 2-5) at a location offset from the pivot 66 along the arm bracket 62. The dual path pulley 160 may have an integral spring cable or secondary pulley 164 and integral cam cable or primary pulley 168 fixed relative to one another. The spring cable pulley 164 has a substantially circular shape around pivot 162, while the cam cable pulley 168 has an asymmetrical shape around the pivot 162 including a lobe 170 that is further from the pivot 162 than the perimeter of the spring cable pulley 164.

A spring cable 180 has a first end joined to one end of resilient element 74 at attachment point 182 (with the other end of the resilient element 74 attached to the arm bracket 62, similar to other embodiments herein), and a second end coupled to the spring cable pulley 164 at attachment point 184. A cam cable 190 has a first end joined to the cam cable pulley 168 at attachment point 192, and a second end joined to cable anchor 84 at attachment point 82.

In a raised arm position, depicted in FIG. 6A, in which the resilient element 74 is relatively retracted (i.e., at a lower potential energy state), the effective radius of the spring cable pulley 164 and integral cam cable pulley 168 may be similar, allowing the spring cable 180 (transmitting the force stored in the resilient element 74) to have approximately equal influence on the dual path pulley 160 as on the cam cable 190. The lobe 170 on the cam cable pulley 168 is not positioned to substantially influence the moments about the pivot 162. In FIG. 6B, with the arm Ar in a lowered position (and the resilient element 74 at a higher potential energy state), the dual path pulley 160 has rotated about the pivot 162, approximately along path Pcp1, bringing the lobe 170 on the cam cable pulley 168 into a position that presents a larger effective radius, and therefore a mechanical advantage, for the cam cable 190 to act on. The spring cable pulley 164, having a smaller effective radius, provides substantially no mechanical advantage for the spring cable 180.

Figure 6C:
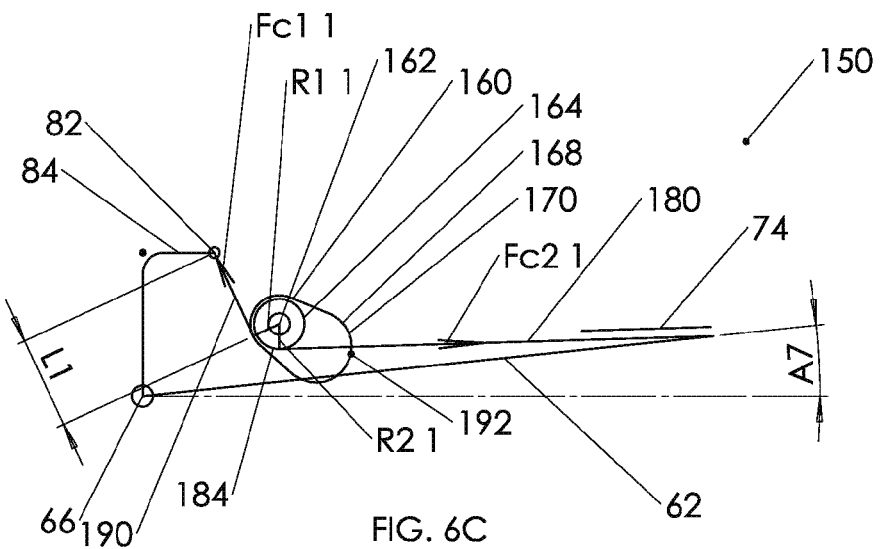
FIGS. 6C and 6D are schematics of elements of the adaptive arm support system of FIGS. 6A and 6B, showing support vectors as the system is moved vertically.
Figure 6D:
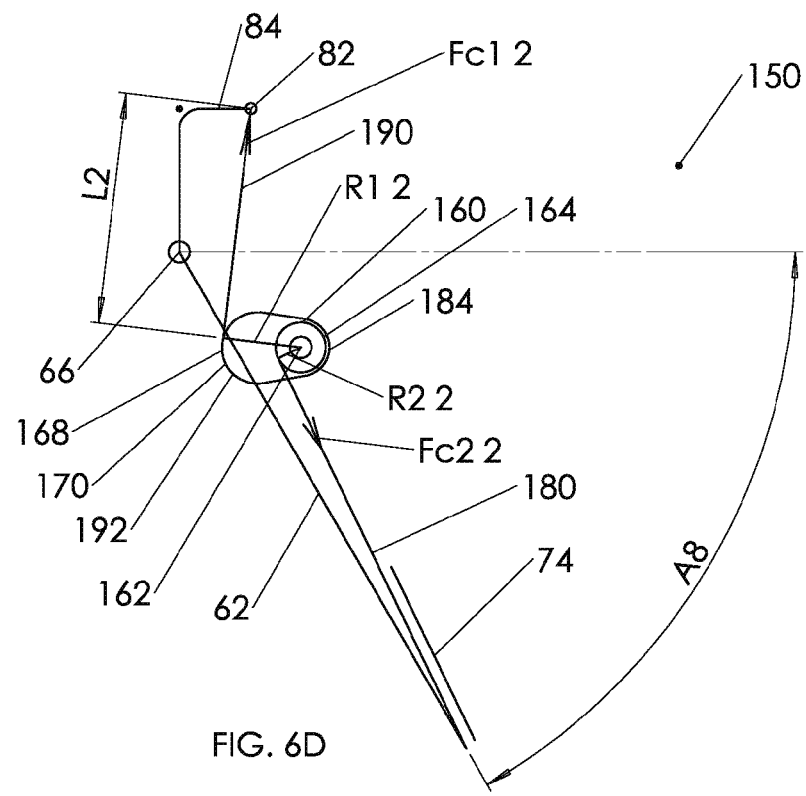

The forces of FIGS. 6A-6B are shown in schematic form in FIGS. 6C-6D. In FIG. 6C, associated with FIG. 6A, the force Fc11 in the cam cable 190 acts on the dual path pulley 160 via the cam cable pulley 168 (with radius R11), while the force Fc21 in the spring cable 180 acts on the dual path pulley 160 via the spring cable pulley 164 (with radius R21). In the position shown, the two radii are approximately equal, providing substantially no mechanical advantage for either force. A length L1 of the cam cable 190 spans the distance between the cam cable pulley 168 and the attachment point 82.

In FIG. 6D, associated with FIG. 6B, the arm bracket 62 is rotated down through angle A8. The length L2 of the cam cable 190 that spans the distance between the cam cable pulley 168 and the attachment point 82 has increased relative to length L1 (FIG. 6C), causing the dual path pulley 160 to rotate about the pivot 162, and bringing the lobe 170 of the cam cable pulley 168 into a position where the effective radius R12 is greater than the effective radius R22 of the spring cable pulley 164. Although the force Fc22 in the spring cable pulley 164 may be greater than force the Fc21 (FIG. 6C) due to deflection (and increased potential energy) of the resilient element 74, the mechanical advantage of the increased effective radius R12 over radius R22 serves to reduce the influence of that greater force, and thus manages the force/moment profile applied to the arm rest 94.

The shapes, locations, centers, attachment points, and sizes of the cam cable pulley 168 and spring cable pulley 164 may be varied to achieve various force profiles and characteristics. For example, a profile may be created that applies a substantially constant force on the arm, regardless of vertical position. Another profile may apply a greater force on the arm when the arm is in a raised position, and less force when the arm is a lowered position. A third profile may have one or more positions in which the force is substantially zero.

Another form of force management is shown in FIGS. 7A-7B, showing another exemplary embodiment of an adaptive arm support system 200. The system 200 generally includes components similar to the system 10 (with similar elements having the same reference number), but employs a shaped attachment element 210 attached to pivot bracket 56, to modify the influence of changes in force of resilient element 74. As shown, the shaped attachment element 210 is substantially fixed relative to the pivot bracket 56 and has an asymmetrical shape extending upwardly therefrom. For example, when raised through a substantially vertical angle A9, cable 216 (joined to the retracted resilient element 74 at connector 218) contacts shaped attachment element 210 where the effective radius Rcm1 is relatively large. When the arm rest 94 is lowered through a substantially vertical angle A10, the cable 216 contacts the shaped attachment element 210 where the effective radius Rcm2 is relatively small, giving the increased force in the cable 216 (due to extension of resilient element 74) less mechanical advantage.

Another form of force management is shown in FIGS. 8A-8B, which shows yet another exemplary embodiment of an adaptive arm support system 250. The system 250 generally includes components similar to the system 10 (with similar elements having the same reference number), but employs a constant-force spring 260 to apply a force to the user's arm (not shown). The constant-force spring 260 is pivotally joined to arm bracket 62 at pivot 266, and to anchor 272 at attachment point 274 via spring tab 262

(spring tab 262 is the end of the coil of the constant-force spring 260). The anchor 272 is adjustably joined to hinge bracket 56. As shown in FIG. 8B, as arm rest 94 is lowered through angle A12, the spring tab 262 lengthens as the constant-force spring 260 uncoils. The force applied by the constant-force spring 260 is substantially consistent, but, due to geometric conditions, the influence of the force on the arm rest 94 varies with the position of the arm rest 94.

Figure 9B:
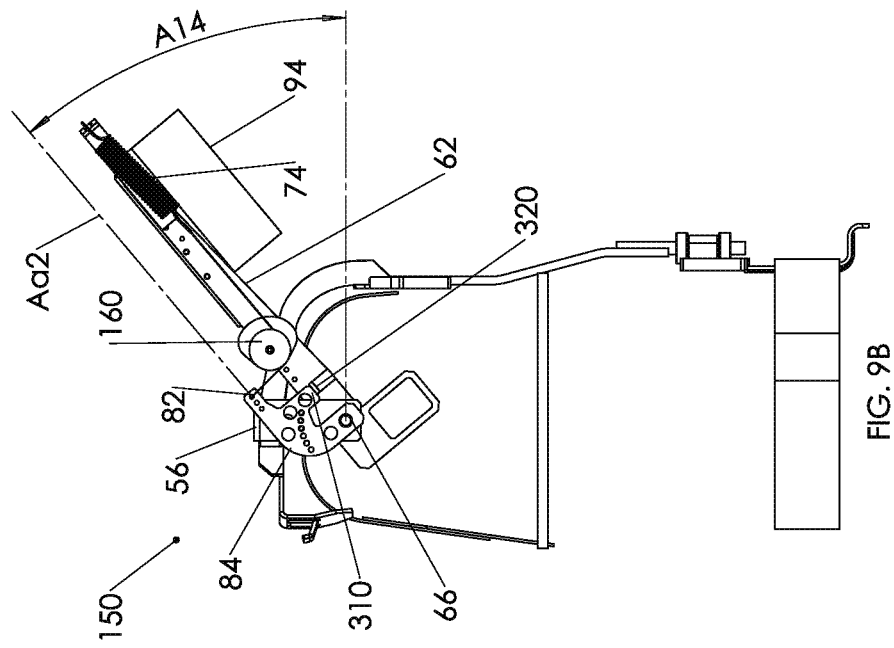
FIGS. 9A and 9B are side views of the adaptive arm support system of FIG. 2 with an arm rest of the system moved vertically upwardly.
Figure 9A:
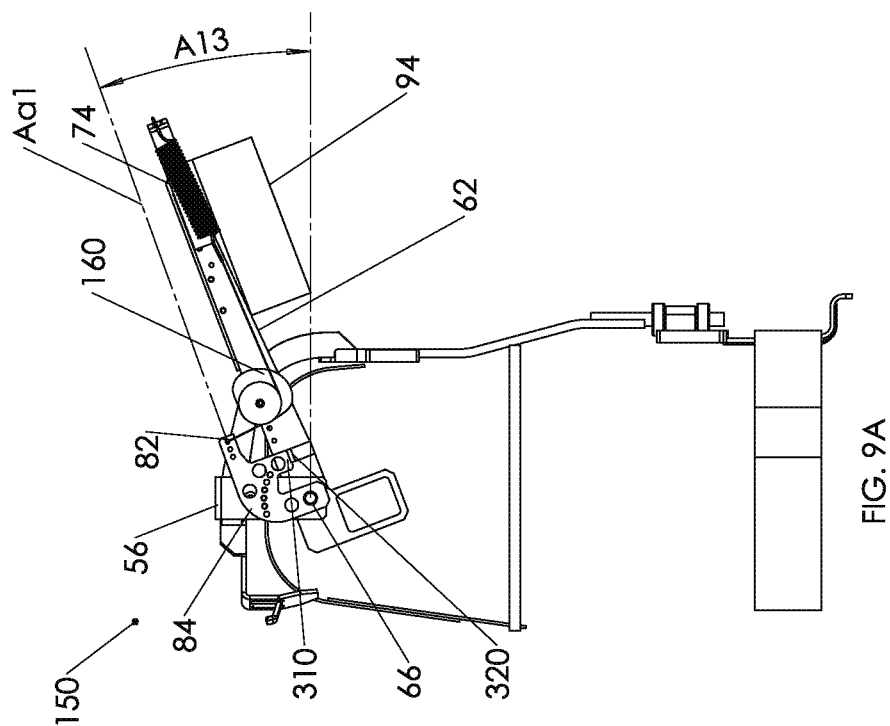

Optionally, in any of the embodiments herein, the maximum elevation of the arm rest 94 may be varied. FIG. 9A shows the system 10 of FIG. 2 with the arm rest 94 fully raised. A hard stop tab 310 is provided on the cable anchor 84 that contacts a corresponding stop tab 320 on the arm bracket 62, preventing further counterclockwise (CCW) rotation (or increased vertical angle of the arm bracket 62) about the pivot 66. Elevation axis Aa1 is separated from the horizontal axis by inclusive angle A13, defining the maximum angle that the arm bracket 62 may be raised before the stop tabs 310, 320 contact one another. In FIG. 9B, the location of stop tab 310 may be changed, and the cable anchor 84 has been rotated CCW further, with elevation axis Aa2 separated from the horizontal axis by inclusive angle A14, providing support for the user's arm Ar at a steeper angle than in FIG. 9A.

Figure 10B:
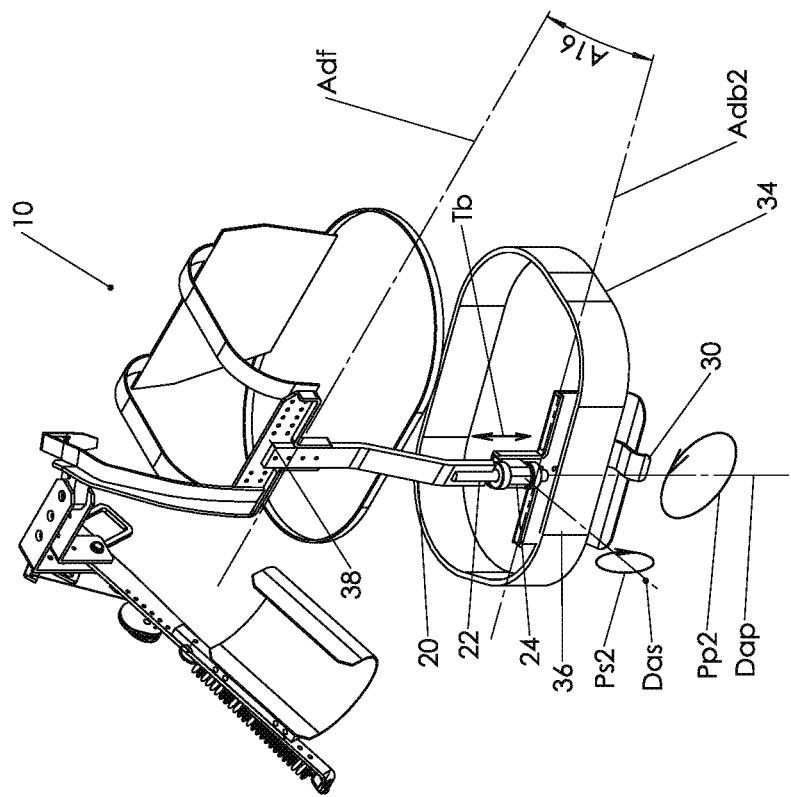
FIGS. 10A and 10B are front perspective views of the adaptive arm support system of FIG. 2 with a pivot shaft of the system rotating about a vertical axis.
Figure 10A:
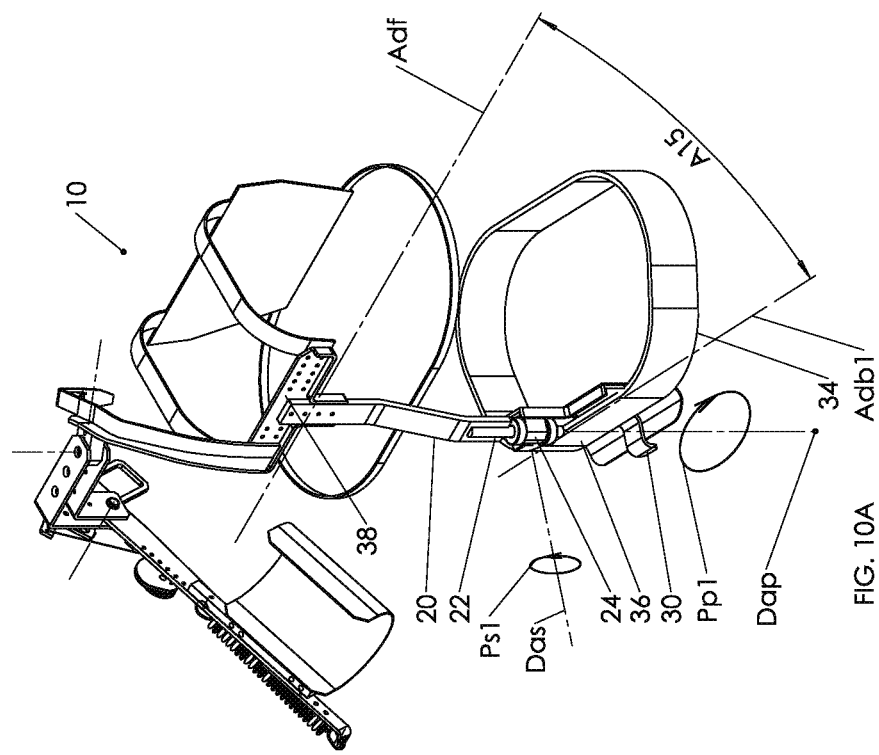

FIGS. 10A-10B shows the system 10 of FIG. 2 with the function of an optional pivot shaft 22 illustrated, e.g., allowing an upper portion of the harness of the system 10 to rotate relative to a lower portion (e.g., secured around or to the user's waist or hips), while transferring vertical forces between the upper and lower portions. The pivot shaft 22 may turn within pivot block 24, enabling rotation about axis Dap, which is consistent with the user rotating his/her upper body at the waist. The pivot block 24 is attached to abdomen plate 26, to which belt 34 is adjustably attached at optional buckle 36 (not shown). Pad 28 may be joined to the abdomen plate 26. Optional hook 30 may also be joined to the abdomen plate 26. As shown in FIG. 10A, the abdomen plate 26 may be rotated about axis Dap through angle A15 relative to a front axis Adf (substantially parallel to support plate 38), approximately along path Pp1. Additionally the pivot block 24 may rotate about axis Das approximately along path Ps1. In FIG. 10B, the abdomen plate 26 is rotated about axis Dap through angle A16 relative to a front axis Adf (substantially parallel to the support plate 38), approximately along path Pp2. Additionally the pivot block 24 may rotate about axis Das approximately along path Ps2. The system 10 may include more than one such pivot arranged in series or in parallel.

FIGS. 11A-11B show another exemplary embodiment of an adaptive arm support system 350 including components similar to the system 10 (with similar elements having the same reference number), but employing a flexible post 360 to join vertical strut 20 to abdomen plate 26. The flexible post 360 may flex in multiple directions, or may be biased to flex only in one direction. As shown in FIG. 11A, axis Dab 1, concentric with top portion 364 of the flexible post 360, is tilted relative to axis Dap by angle A11 (consistent with the user bending at the waist). As shown in FIG. 11B, axis Dab 2, concentric with the top portion 364 of the flexible post 360, is further tilted relative to axis Dap by angle A1 (consistent with the user bending further at the waist). The flexible post 360 may also rotate within pivot block 24, about axis Dap, while transferring forces between upper and lower portions of the harness.

A variant of system 10, employing a different force management apparatus, is shown in FIGS. 12A-12B. Adaptive arm support system 400 generally includes similar components to the system 10 (with similar elements having the same reference numbers), but employs a gas extension spring 415 in place of resilient element 74. The gas extension spring 415, which includes body 420 and shaft 425, may be coupled to arm bracket 62 at mount 76, and to cable 180 at attachment point 182. As shown in FIG. 12B, the gas extension spring 415 extends as the arm rest 94 is lowered, with the shaft 425 extending relative to the body 420 in response. The gas extension spring 415 may provide desirable damping forces to limit the rotational speed of the arm bracket 62.

Turning to FIGS. 13A and 13B, another exemplary embodiment of an adaptive arm support system 500 is shown that is worn by a user U. Generally, the support 500 includes one or two arm support assemblies 505 (two shown) and a harness assembly 510, which together serve to adaptively support the user's arm(s), similar to other embodiments herein.

The harness assembly 510 includes features that create one or more substantially vertical shoulder pivots 552, approximately concentric with the user U's shoulder S, similar to those described elsewhere herein and in the applications incorporated by reference herein. The shoulder vertical pivots 552 are further defined by axes Davl and Davr, about which they rotate. Arm support assembly 505, which pivots at shoulder horizontal pivot 584 about axis Dahl (Dahl also being approximately concentric with shoulder S, and may or may not be perpendicular to axis Davl), is biased to provide a lifting force on left arm A1, thereby counterbalancing all, or a portion of, the weight of the arm. The arm assembly 505 is joined to the harness assembly 510, and thus transmits the load of arm A1 to other reaction points on the body of the user U, for example, the shoulder S, waist W, hips H, and back B (e.g., as represented by the forces shown in FIG. 18).

The pivots 552 and 584 provide a way to transmit loads and/or moments from each arm assembly 505 to the harness assembly 510 through movable (adaptive) joints, which allow the arm assembly 505 to follow the motion of the user U's arm (e.g., with minimal resistance to such motion), while supporting all, or a portion of, the weight of the arm. The pivots 552 and 584 are located approximately above and beside the user's shoulder, keeping clear the space normally associated with working with the arms out, raised, outstretched, and/or forward (i.e., the area of the chest, waist, lap, inside and underneath the arms).

Optional covers (not shown) may protect the adaptive arm support system 500 and/or the user U. For example, covers may protect components of the adaptive arm support system 500 and/or the user U from weather, contamination, electricity, heat, pinch points, and the like.

Turning to FIGS. 14A and 14B, the adaptive arm support system 500 is shown without the user U to facilitate identification of components of the system 500. For example, shoulder pad 520, which may be placed over the shoulders of the user (not shown) attaches to back pad 524 and vertical straps 528 may join the shoulder pad 520 at chest buckle 530 and to hip or waist belt 538 at optionally adjustable buckle 534, e.g., by one or more of stitching, bonding with adhesive, and the like. The shoulder pad 520 and back pad 524 may be substantially rigid or flexible, as desired, may be padded to increase comfort, may include mesh or other material, e.g., to allow the pads to breathe and/or reduce overheating, and the like.

The chest strap 526 joins the shoulder pad 520 and includes a chest strap closure 532 that releasably secures ends of the chest strap 526, while belt closure 540 releasably secures ends of the belt 538. The closures 532, 540 may include any closure mechanisms that allow the strap 526 and belt 538 to be opened, e.g., to allow the system 500 to be worn or removed by the user, and closed to substantially secure the system 500 on the user, such as buckles, hook and eye fasteners, latches, burdock fasteners, claps, and the like.

The belt 538 may be flexible, stiff, stiff in one axis only, stiff in more than one axis, stiff in torsion, hinged, jointed, adjustable, spring loaded, padded, and/or ventilated. The belt 538 may also be formed from a variety of materials, such as metal, polymer, elastomer, webbing, sewn fabric, foam, mesh, or combination thereof.

Optionally, other configurations for the harness assembly 510 may be provided for contacting the user wearing the system 510, which may include one or more of a lap pad, lap plate, thigh straps, lower back support belt, underarm slings, headrest, chin rest, forehead rest, and the like (not shown), e.g., as described elsewhere herein.

Tools or other accessories (not shown) may be attached to points on the adaptive arm support system 500, as desired for a particular application. For example, hand tools, supplies, tool holders, pouches, hooks, lamps, hydration devices, communication devices, clamps, a fold-out support, a fold-out table, and/or other devices (not shown) might be attached to desired locations of the adaptive arm support system 500, such as on the belt 538, on the shoulder, chest, or vertical straps 520, 526, 528, and/or elsewhere on the harness assembly 510.

As best seen in FIG. 14A, a pair of abdomen tubes 542 attach to the belt 538 at belt-tube clamp 544, e.g., at the front of the belt 538 and extend around to the back of the harness assembly 510. At the back of the harness assembly 510, each abdomen tube 542 may attach to a lower tube socket 626, which may act as a vertical axis pivot, as best seen in FIG. 14B. The lower tube socket 626, in turn, may be attached to a cross brace 620 extending between the opposite lower tube sockets 626. A pair of frame straps 624 are attached at their lower ends to the cross brace 620, and at their upper ends to shoulder support tubes 546, which are, in turn, attached to upper tube sockets 628, each of which may also act as a vertical axis pivot.

Each of the abdomen tubes 542, shoulder support tubes 546, and/or frame straps 624 may be substantially rigid, semi-rigid, flexible, or selectively rigid, as desired, and may be formed from hollow tubing or solid rod material, e.g., having a substantially uniform or variable outer shape, such as a round, square, U-shaped, I-shaped, T-shaped, or other non-circular cross-section. The abdomen tubes 542, shoulder support tubes 546, and/or frame straps 624 may be formed from a variety of materials, such as metal, polymer, elastomer, or combination thereof, e.g., such that the components together have sufficient rigidity to provide support, and/or force translation and/or moment transmission through the harness assembly 510 during use of the system 500, as described elsewhere herein.

With continued reference to FIG. 14B, back ends of the shoulder pads 520 attach to the back pad 524, and back ends of the chest straps 526 attach to the back pad 524 near the cross brace 620. Each shoulder support tube 546 is coupled to and supports a shoulder pivot mount 548, which, in turn, is coupled to and supports a shoulder pivot clevis 550. Each shoulder pivot clevis 550 cooperates with a support bar 554 to form a shoulder vertical pivot 552, which rotates about, and is further defined by, axis Davr (for the right arm support assembly 505) and Davl (for the left arm support assembly 505).

Each set of shoulder support tube 546, upper tube socket 628, frame strap 624, cross brace 620, lower tube socket 626, and abdomen tube 542 together provide a selectively rigid frame. For example, the resulting harness 510 may be substantially rigid in a vertical direction, e.g., to transmit forces, while providing flexibility in other directions, e.g., to allow rotation horizontally if the user U turns at the waist, to allow the user U to bend forward at the waist, and/or accommodate other movement of the user U with minimal resistance. Optional vertical pivots (at upper tube socket 628 and lower tube socket 626) may serve to transmit loads (forces and moments) from the respective arm support assembly 505, through the harness assembly 510, to various reaction points on the body of the user (e.g., as further described with reference to FIG. 18), or on other structures (e.g., as further described with reference to FIGS. 20-24).

With reference to the right arm support assembly 505 (with recognition that the left arm support assembly 505 operates similarly, if provided), the support bar 554 is free to rotate about axis Davr (due to the shoulder vertical pivot 552) and is fixedly mounted to the right arm support assembly 505. Thus, the support bar 554 allows the arm support assembly 505 to pivot freely about axis Davr in response to side-to-side motion of the user's arm. Optionally, the arm support assembly 505 may be removable from the support bar 554, rather than permanently attached to the support bar 554. For example, the support bar 554 and/or arm support assembly 505 may include one or more connectors (not shown) to securely and releasably attach the arm support assembly 505 to the support bar 554.

Turning to FIGS. 14C and 14D, details of an exemplary embodiment of an arm support assembly 505 for the adaptive arm support system 500 of FIGS. 14A and 14B can be seen with the cover 576 shown in FIGS. 14A and 14B removed, with the arm support assembly 505 substantially raised (consistent with user's arm raised). As shown, a chassis 580 of the arm support assembly 505 may pivot about shoulder horizontal pivot 584 (defined by axis Dahr, not shown, see FIG. 14B) in response to raising and lowering motions of the user's arm. Cable anchor 558 is substantially fixed relative to the support bar 554 and provides a cable anchor point 562, at which anchor cable 560 is attached. The cable anchor 558 may be rotationally adjustable relative to support bar 554 to permit the user to change the range of use of the arm support assembly 505. The cable anchor 558 may also be releasable from the support bar 554, e.g., to permit the arm support assembly 505 to rotate freely about the shoulder horizontal pivot 584, for example, to take the arm support assembly out of service. The anchor cable 560 wraps around a primary pulley 564 in a cable groove (not shown) and is attached to the primary pulley 564 at attachment point 561. The primary pulley 564 rotates about pulley pivot 572 on the chassis 580. A secondary pulley 570 is rigidly joined to the primary pulley 564 such that the secondary pulley 570 rotates in conjunction with the primary pulley 564 about the pulley pivot 572.

A resilient element cable 634 attaches to the secondary pulley 570 at attachment point 573, lies within a portion of cable groove 652 (not shown, see, e.g., FIG. 15A), wraps around an optional reversing pulley 630, and attaches to a first end of a resilient element 636 via cable attachment 640. The reversing pulley 630 rotates about reversing pulley pivot 632 on the chassis 580. Resilient element hook 638 on the chassis 580 is coupled to a second end of the resilient element 636, thereby substantially securing the second end relative to the chassis 580. The chassis 580 provides a stable mounting platform for the pulleys and resilient element, as well as arm rest 600. The arm rest 600 provides a cradle for the user's arm. In exemplary embodiments, the resilient element 636 may be a spring, e.g., an extension spring, band, strap, gas spring, and the like, and may be formed from a variety of materials, such as metal, elastomer, and the like.

As shown in FIG. 14C, with the arm support assembly 505 in a raised position (above horizontal), the anchor cable 560 extends around a substantial portion of the cable groove of the primary pulley 564 (e.g., greater than half the circumference of the primary pulley 564) and the resilient element cable 634 extends around a relatively small portion of the cable groove 652 of the secondary pulley 570 (e.g., less than half the circumference of the secondary pulley 570). In this position, the resilient element 636 may be in a substantially retracted position, e.g., a lower potential energy state, at which it will exert low-to-moderate force on the resilient element cable 634, and thus on the secondary pulley 570.

The secondary pulley 570 may have multiple radii about its circumference, thereby defining a non-circular cable groove 652 (as best seen in FIG. 15B) in order to provide selective mechanical advantage/disadvantage to the resilient element 636 during use, as desired for lift-force management and described elsewhere herein. In exemplary embodiments, instead of the shape shown in FIG. 15B, the secondary pulley 570 may be substantially circular with an eccentric hole (see, e.g., FIGS. 17A-17B), may be elliptical, may have curved sections, may have straight sections, may have concave sections, may be symmetrical, may be asymmetrical, and the like (not shown), e.g., customized for a user's needs based on the expected range of motion and/or activities of the user, as described elsewhere herein.

Turning to FIG. 14D, the system 500 of FIG. 14C is shown with the arm support assembly 505 substantially lowered (consistent with user's arm lowered). As shown, the arm support assembly 505 has been rotated about the shoulder horizontal pivot 584, approximately along Path Pr10 in response to the motion of the user's arm. During this motion, the secondary pulley 570 and primary pulley 564 have rotated together about the pulley pivot 572, approximately along path Pr11. Consequently, the anchor cable 560 is largely unwrapped from the primary pulley 564 (such that the anchor cable 560 extends around less of the cable groove of the primary pulley 564, e.g., less than half the circumference of the primary pulley 564), and the resilient element cable 634 is now largely wrapped around the secondary pulley 570 (such that the resilient element cable 6344 extends around more of the cable groove 652 of the secondary pulley 570, e.g., greater than half the circumference of the secondary pulley 570). In response, the resilient element 636 is shown in a substantially extended or stressed position (e.g., a higher potential energy state).

Although the resilient element 636 is extended, and is therefore exerting more force on the resilient element cable 634, its influence (its ability to apply an increasing lifting force to the user's arm) is moderated by the shape of the secondary pulley 570, which has different radii on which the resilient element cable 634 may apply moments (as discussed further below).

For example, as shown in FIGS. 15A and 15B, the secondary pulley 570 may have a cable groove 652 in which the resilient element cable 634 (not shown) is constrained. The resilient element cable 634 may attach to the secondary pulley 570 at the cable attachment point 573. Pulley rotation bore 654 provides a pivot for the secondary pulley 570, i.e., that is rotationally coupled to the pulley pivot 572 with the primary pulley 564.

As best seen in the cross-section of FIG. 15B, the distance from the pulley rotation bore 654 to the cable groove 652 varies as required to manage lift forces on the user's arm as the spring force applied by the resilient element 636 increases (or decreases) through displacement. For example, radius R25 differs from radius R20. A tangential force (provided, for example, by a resilient element cable, not shown), acting at any given radius, will have more (or less) influence based on the length of the radius. Zones of influence may be created to achieve a desired result.

For example, in the exemplary embodiment shown, influence zone Z10 may include one radius (e.g., R21 at one end of the zone equal to R20 at the other end of the zone), while influence zone Z11 may include constantly varying radii (e.g., with R23 at one end of the zone less than R22 at the other end of the zone). In influence zone Z12, the radii are varied to create an essentially straight section of Cable groove 652. Other relationships are contemplated, which may be customized to provide desired moments and/or resulting support forces.

The length and angular relationship of the radii may be varied to produce a desired lifting force on the user's arm. For example, the secondary pulley 570 may be configured to provide a short zone Z11, and a longer zone Z12, consistent with tasks requiring maximum lift at a specific elevation of the user's arm, but little lift at other elevations (e.g., pointing a camera). For tasks requiring a longer area of maximum lift (e.g., product assembly), Z11 may be larger.

Turning to FIG. 16, an exemplary plot of arm weight moment, lifting moment, and resultant moment for secondary pulley 570 is shown. The moments may act about shoulder horizontal pivot 584 (e.g., defined further by axis Dahl or Dahr) of the arm support assembly 505 including the secondary pulley 570. Arm weight Wa of the user's arm provides a negative moment AWM about Pivot 584, acting to rotate Arm support assembly 505 downward. Negative moment AWM depends on input angle Theta, the relative angle of the major axis of the arm support assembly 505 relative to a horizontal axis. The arm support assembly 505, acting through the system of springs, cables, and pulleys described above, provides a positive (lifting) moment AASM about the shoulder horizontal pivot 584, acting to rotate the arm support assembly 505 upward. Positive moment AASM depends on input angle Theta, the relative angle of the major axis of the arm support assembly 505 to the horizontal. The resultant moment RM is the sum of AWM and AASM.

As discussed with reference to FIG. 15B, zones of varying or consistent influence may be created by varying the length and angular relationship of the radii of the secondary pulley 570. As shown, influence zone Z11 may provide a relatively consistent lift force (as shown by the relatively straight portion of RM labeled "Z11" in FIG. 16. Influence zone Z12 may be associated with varying lift force, as shown by the relatively curved shape of RM labeled "Z12" in FIG. 16. Thus, the lift-force on the user's arm may be shaped as required or desired.

Turning to FIGS. 17A and 17B, an alternative embodiment of a secondary pulley 660 is shown that includes a substantially symmetric (e.g., circular) shape including a cable groove 662 in which a resilient element cable 634 (not shown, see, e.g., FIGS. 14C-14D) may be received. The resilient element cable 634 may attach to the secondary pulley 660 at cable attachment point 666, similar to the previous embodiment. Pulley rotation bore 664 provides a pivot for the secondary pulley 660, i.e., that may be coupled to the pulley pivot 572 with the primary pulley 564 of FIGS. 14c-14D (such that the circular pulleys are radially offset from one another).

As can be seen in FIG. 17B, the distance from the pulley rotation bore 664 to the cable groove 662 may vary as desired to manage lift force on an arm (supported by an arm support assembly including the secondary pulley 660), even when the spring force from a resilient element of the arm support assembly increases through displacement. For example, radius R28 differs from radius R29. A tangential force (provided, for example, by a resilient element cable, not shown), acting at any given radius, will have more (or less) influence based on the length of the radius. The length and angular relationship of the radii may be varied to produce a desired lift-force on the user's arm.

Turning to FIG. 17C, an exemplary plot of arm weight moment, lifting moment, and resultant moment for secondary pulley 660 is shown. The moments may act about the shoulder horizontal pivot 584 (defined further by axis Dahl or Dahr, as shown in FIGS. 14A and 14B) of the arm support assembly 505 including the secondary pulley 660. Arm weight Wa provides a negative moment AWM about the shoulder horizontal pivot 584, acting to rotate Arm support assembly 505 downward. Negative moment AWM depends on input angle Theta, the relative angle of the major axis of the arm support assembly 505 to the horizontal. The arm support assembly 505, acting through the system of springs, cables, and pulleys described above, provides a positive (lifting) moment AASM about the shoulder horizontal pivot 584, acting to rotate the arm support assembly 505 upward. Positive moment AASM depends on input angle Theta, the relative angle of the major axis of the arm support assembly 505 to the horizontal. The resultant moment RM is the sum of AWM and AASM. As discussed in reference to FIG. 17B, different radii (e.g., R28 and R29) in the secondary pulley 660 may provide different amounts of lift force at different input angles, creating a lift-force profile that differs from that of the secondary pulley 570 (discussed with reference to FIGS. 17A-C). Thus, the lift-force on the user's arm may be shaped as desired. It will be appreciated that numerous other pulley shapes and/or sizes are contemplated. Optionally, any primary pulley and/or secondary pulley may be rotationally adjustable relative to each other, as desired by the user, for example, to change the characteristics of the lift-force profile provided by the arm support assembly 505.

Turning to FIG. 18, an exemplary arrangement of forces acting on the adaptive arm support system 500 of FIGS. 14A and 14B are shown. Arm weight Wa acts on the arm rest 600, imparting forces and moments to the adaptive arm support system 500 that must be resisted by portions of user U's body to maintain static balance. For example, the user's hip H may provide a hip reaction force Rh, acting to resist the weight Wa. Similarly, other portions of the body may provide such reaction forces, such as the shoulder reaction force Rs, back reaction force Rb, waist reaction force Rw, and/or lap reaction force Rl. Thus, the arm weight Wa may be distributed by the adaptive arm support system 500 onto other portions of the body, relieving the muscles of the user's back and shoulder, which are normally employed to keep the arms outstretched or raised. Additionally, the arm weight Wa may be transmitted through the adaptive arm support system 500 to an external structure, such as a table or rail (not shown), which may provide one or more Table reaction forces Rt, as described elsewhere herein.

Turning to FIGS. 19A and 19B, exemplary views of the adaptive arm support system 500 of FIGS. 14A and 14B are shown. As shown, one of the arm support assemblies 505 (for the left arm of a user, not shown) may be rotated about axis Davl, as shown by arc Pr12, and approximately along rotation path Pr13. Given the support of the arm support assembly 505 and the minimal resistance to rotation provided by the shoulder support clevis 550, such rotation may be accommodated without requiring additional energy from the user.

Turning to FIGS. 19C-19E, additional views of the adaptive arm support system 500 of FIGS. 14A and 14B is shown in which both arm support assemblies 505 have been separated from the harness assembly 510 (with only one arm support assembly 505 still shown in FIG. 19C to facilitate observation of other components of the system 500). The harness assembly 510 may include one or more substantially vertical pivots in addition to shoulder vertical pivot(s) 552. These additional vertical pivots serve to increase the comfort and flexibility, as well as the range of the harness assembly 510. For example, the shoulder support tube(s) 546 may rotate about the shoulder tube pivot(s) 629 in the upper tube socket(s) 628 around shoulder tube axis FPasl and shoulder tube axis FPasr. Similarly, abdomen tube(s) 542 may rotate about abdomen tube pivot 627 in lower tube socket(s) 626 around abdomen tube axis FPaal and abdomen tube axis FPaar. These additional pivots may serve to increase the flexibility of the harness assembly 510 while still translating desired forces, as described further below.

For example, the abdomen tube pivot 627 may ease the donning and/or removing the adaptive arm support system 500. As shown in FIG. 19D, the belt 538 may be opened at the belt closure 540, approximately along Belt opening path Pbo1. To allow the belt 538 to open fully, the abdomen tube(s) 542, which may be substantially rigid, and/or attached to the belt 538 by the belt-tube clamp(s) 544, may pivot about the abdomen tube axis FPaal and abdomen tube axis FPaar, approximately along abdomen tube pivot path Pp11 and abdomen tube pivot path Pp12, respectively. This action may allow the belt 538 to open sufficiently for the user to put on the adaptive arm support system 500, e.g., by opening the system 500 similar to a jacket, sliding their arms through the spaces below the shoulder pads 520 and then over the user's head and shoulders (not shown).

In addition, as shown in FIG. 19E, a shoulder support tube 546 (in this case the right shoulder support tube 546) may be pivoted backward about the shoulder tube axis FPasr (not shown, see, e.g., FIG. 19D)), at the shoulder tube pivot 629 in upper tube socket 628, approximately along shoulder tube pivot path Pp14, thus providing the harness assembly 510 with greater flexibility at the shoulder, which may enhance user mobility and comfort.

Turning to FIGS. 20A-20D, it may be advantageous to use the adaptive arm support system 500 to transfer all or a portion of the weight of the user's arms and/or upper body to another structure (e.g., to a table, not shown), to reduce the reaction loads on the user's body (e.g., as discussed with reference to FIG. 18). For example, the system 500 may include a load transfer bracket 702, e.g., attached to various points on the harness assembly 510, which may be adapted to mount various load transfer accessories to the system 500, as described further below.

Figure 20D:
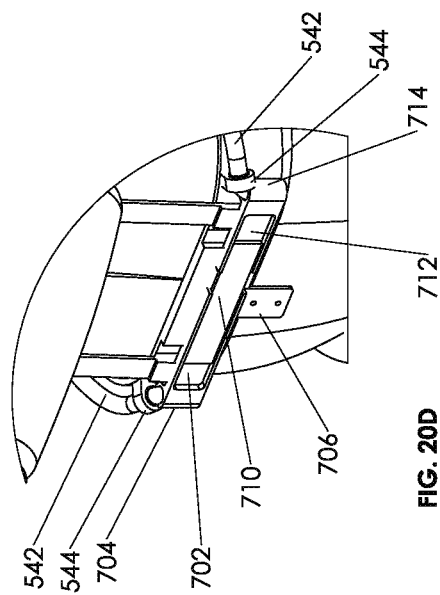
FIG. 20D is a detail of the closed load transfer bracket of the system shown in FIG. 20C.
Figure 20C:
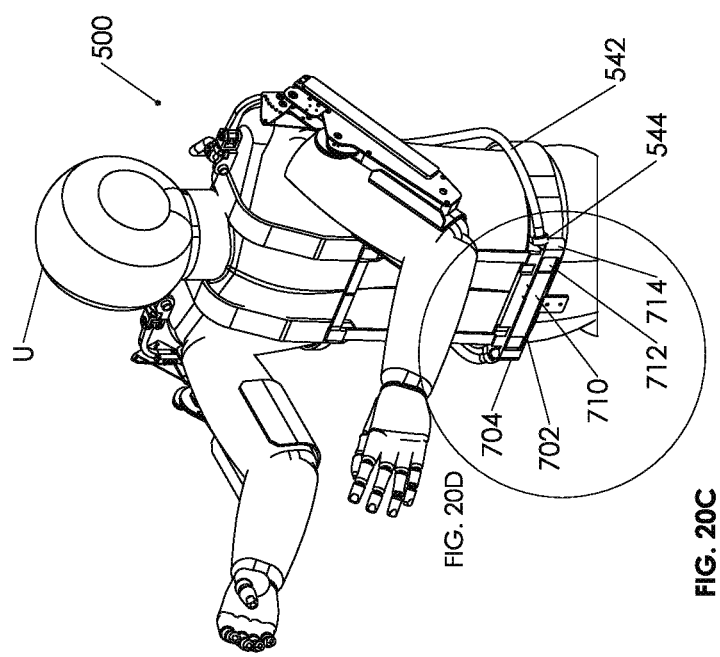
FIG. 20C is a front perspective view of the system shown in FIG. 20A showing the load transfer bracket of the system in a closed position.

As shown in FIGS. 20A and 20C, the load transfer bracket 702 may be coupled to one or more of the belt 538, abdomen tube 542, belt-tube clamp 544, and/or other portion of the harness assembly 510 suitable for transmitting load. The load transfer bracket 702 may include a load transfer bracket pivot 704, about which the load transfer bracket 702 may rotate, e.g., between an open position (shown in FIGS. 20A and 20B) and a closed position (shown in FIGS. 20C and 20D). The load transfer bracket 702 may include a load transfer tab 706 to permit attachment of various load transfer accessories, such as those described further below. Load transfer strap 712, which includes Load transfer strap pivot 714 (about which it may rotate), may be attached to another portion of the harness assembly 510, e.g., generally opposite the load transfer bracket 702.

As best seen in FIG. 20B, the load transfer bracket 702 and load transfer strap 712 are separated, i.e., in the open position, to allow the adaptive arm support system 500 to be donned or removed, as described elsewhere herein. A Load transfer bracket closure 710 allows the load transfer bracket 702 and load transfer strap 712 to be substantially rigidly joined together, e.g., as best seen in FIG. 20D. For example, after donning the system 500, the load transfer bracket 702 may be rotated about the load transfer bracket pivot 704, and then the load transfer strap 712 may be rotated about the load transfer strap pivot 714. The load transfer bracket closure 710 may then be engaged to join the load transfer bracket 702 and load transfer strap 712 together.

Once joined together, the load transfer bracket 702 and load transfer strap 712 may provide a substantially rigid structure coupled to the harness assembly 510, to which various load transfer accessories may be attached. In exemplary embodiments, the load transfer bracket closure 710 may be a buckle, latch, burdock fastener, clasp, rigid, flexible, padded, and the like (not shown). The load transfer bracket closure 710 may be may be flexible, stiff, stiff in one axis only, stiff in more than one axis, stiff in torsion, hinged, jointed, adjustable, spring loaded, padded, ventilated, and the like. The load transfer bracket closure 710 may be formed from a variety of materials, such as metal, polymer, elastomer, other materials, or combination thereof.

Figure 21B:
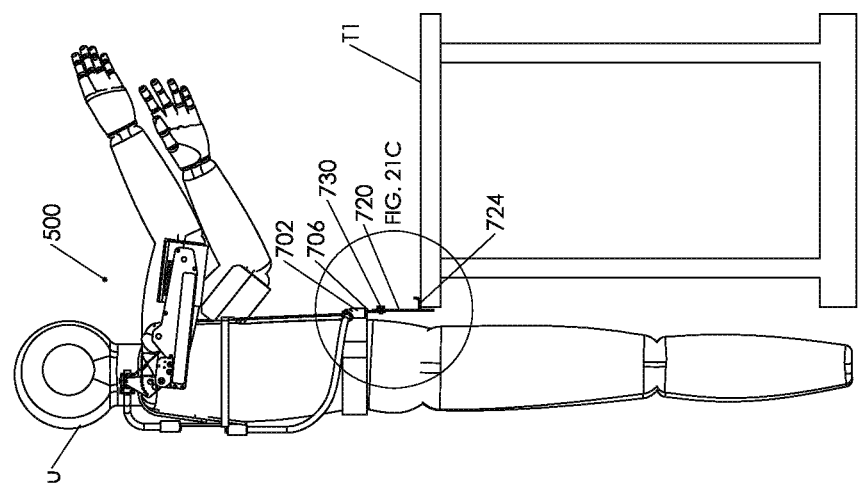
FIGS. 21A and 21B are perspective and side views, respectively of the system of FIGS. 13A and 13B worn by a user and including a load transfer bracket being at least partially supported by a table.
Figure 21A:
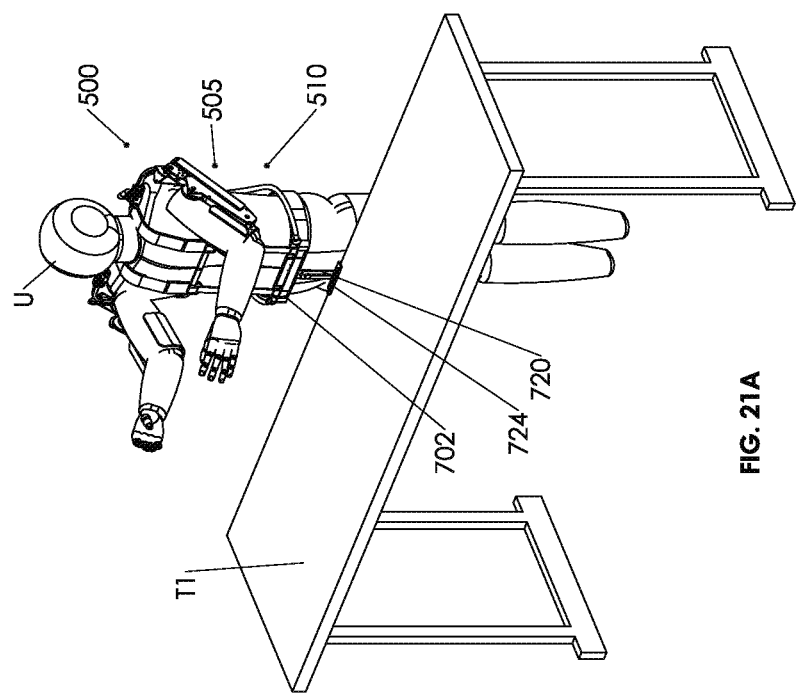

Turning to FIGS. 21A-21C, the adaptive arm support system 500 is shown with loads being transferred from the system 500 to a Table T1 through an attachment, namely a table hook 720 attached to the load transfer bracket 702, e.g., in order to reduce (or eliminate) reaction loads on the user's body (e.g., the reaction loads described elsewhere herein with reference to FIG. 18).

As shown, the user U may transfer some or all of the weight of the adaptive arm support system 500, the arms of user U, and/or any tools or other objects held by user U to an appropriate external structure, such as the table T1. The user may approach and lean against the table T1 to transfer loads from the weight(s). The table hook 720, attached to the harness assembly 510 via the load transfer bracket 702, may be directed by user U to engage an appropriate edge of the table T1, e.g., to permit transfer of forces from the adaptive arm support system 500 to the table T1.

As best seen in FIGS. 21B and 21C, the table hook 720, secured to the load transfer tab 706 of the load transfer bracket 702, engages the edge of the table T1, allowing user U to rest the adaptive arm support system 500 on the edge of the table T1, thereby relieving the reaction loads on the user's body (again described elsewhere herein with reference to FIG. 18). In the embodiment best seen in FIG. 21C, the table hook includes a table hook tab 724, an optional table hook lead-in 726, and a table hook tail 728. The table hook tab 724 may provide structure that may impart a vertical (downward) force (the weight of the adaptive arm support system 500, the arms of the user U, and/or any tools or other objects held by user U) transferred from the harness assembly 510 to the table T1, which is balanced by (for example) a vertical table reaction force Rtv1, as shown in FIG. 21C.

The optional table hook lead-in 726 may be tapered or otherwise shaped to ease engagement with the table T1, e.g., to slide along the edge of the table T1 until the table hook tab 724 abuts the table T1. The table hook tail 728 may provide structure that may impart a horizontal (sideways) force transferred from the harness assembly 510 to the table T1, which may be balanced by a similar horizontal table reaction force Rth, also shown in FIG. 21C. Optionally, the table hook 720 may be adjustable relative to the load transfer tab 706 of the load transfer bracket 702, e.g., using an adjustment knob 730 to adjust a length of the table hook 720 (i.e., adjust the distance from the load transfer tab 706 to the table hook tab 724), to optimize the engagement of the table hook 720 with the table T1 for a given user U. In addition or alternatively, other adjustment mechanisms may be provided, such as clips, ratchets, burdock fasteners, screws, and the like (not shown).

The table hook 720 may be substantially rigid to transfer all forces from the harness assembly 510 to the table T1, may be semi-rigid, flexible, and/or may be articulating, spring-loaded, damped, compressible, bendable, flexible in only one axis, or flexible in two or more axes, and the like. The table hook 720 may be formed from a variety of materials, such as metal, polymer, elastomer, or combination thereof. Optionally, the table hook 720 may include additional features to contact the table T1 in addition to or instead of the table hook tab 724, such as one or more pads, skids, rollers, wheels, balls, pins, cleats, burdock fasteners, magnets, vacuum elements, and the like. (not shown).

Turning to FIGS. 21D and 21E, another example of an attachment accessory, namely table clamp 734, is shown that may be coupled to the adaptive arm support system 500 (or any other embodiment herein) to transfer loads to a table T1 or other structure. As shown, the table clamp 734 is secured to the load transfer tab 706 of the load transfer bracket 702, e.g., with Adjustment knob 730. The table clamp 734 may engage the edge of the table T1, allowing the user U to rest the adaptive arm support system 500 on the edge of the table T1. The table clamp 734 may also allow the user U to lean forward (not shown), applying a moment to the table T1 until a reaction moment on the table clamp 734, imparted by the table T1, resists the motion. Thus, the weight of the user's upper body may be supported in static balance as the user U leans over the table T1.

Turning to FIG. 21E, exemplary forces are shown that may be transferred between the adaptive arm support system 500 and the table T1 by the table clamp 734. As shown, the table clamp 734 includes a table clamp upper tab 736 that engages the top of the table T1. The table clamp upper tab 736 provides structure that imparts a vertical (downward) force transferred from the harness assembly 510 to the table T1, which is balanced by (for example) a vertical table reaction force Rtv1. The table clamp 734 also includes a table clamp lower tab 742 that engages the bottom of the table T1, and provides structure which may impart a vertical (upward) force transferred from the harness assembly 510 to the table T1, which may be balanced by a vertical table reaction force Rtv2. The table clamp 734 also includes a table clamp back 740 that provides structure, which may impart a horizontal (sideways) force transferred from the harness assembly 510 to the table T1, and which may be balanced by a similar horizontal table reaction force Rth.

Optionally, the table clamp 736 may include a table clamp upper lead-in 738 and/or a table clamp lower lead-in 744, which may ease engagement of the table clamp 734 to the table T1. Together, the vertical table reaction force Rtv1 and vertical table reaction force Rtv2 may provide a reactive moment on the harness assembly 510, resisting the moment imparted to the table T1, e.g., caused by the user U leaning forward.

The table clamp 734 may be adjustable relative to the load transfer tab 706 of the load transfer bracket 702, e.g., using an adjustment knob 730, to optimize the engagement of the table clamp 734 with the table T1 for a given user U, similar to other embodiments herein. In addition or alternatively, other adjustment mechanisms may be provided, for example clips, ratchets, burdock fasteners, screws, and the like (not shown).

The table clamp 734 may be substantially rigid, flexible, articulating, spring-loaded, damped, compressible, bendable, flexible in only one axis, and/or flexible in two or more axes, similar to other embodiments herein. The table clamp 734 may be formed from a variety of materials, such as metal, polymer, elastomer, or combination thereof, and/or may include additional features to contact the table T1, such as one or more pads, skids, rollers, wheels, balls, pins, cleats, burdock fasteners, magnets, vacuum, etc. (not shown), also similar to other embodiments herein.

Figure 22B:
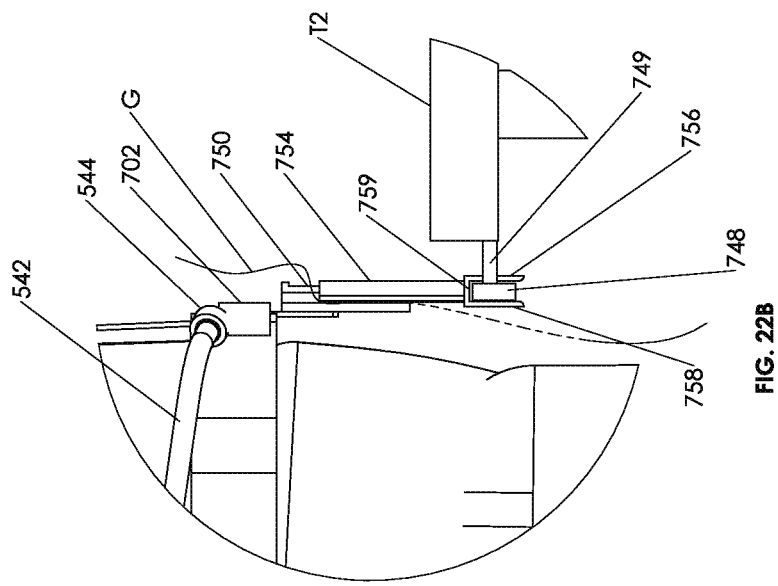
FIG. 22B is a detail of the cooperation between the load transfer bracket of the system of FIG. 22A and the rail of the table.
Figure 22A:
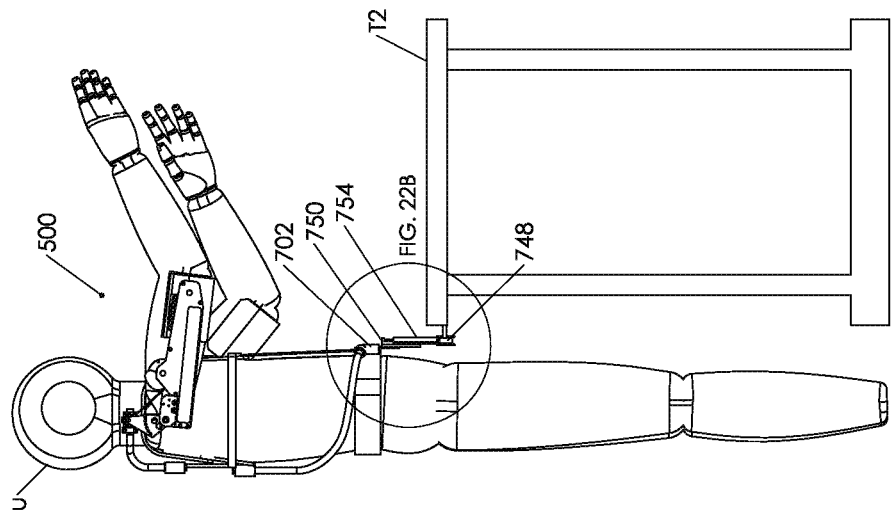
FIG. 22A is a side view of the system of FIGS. 13A and 13B worn by a user and including another alternative embodiment of a load transfer bracket being at least partially supported by a cooperating rail on a table.

Turning to FIGS. 22A and 22B, another exemplary embodiment of an attachment accessory, namely a load clamp 754, is shown that may be coupled to the adaptive arm support system 500 (or any other embodiment herein) to transfer loads to a specialized table T2. As shown, the specialized table T2 may have a rail 748, e.g., extending along an edge of the table T2 for a predetermined distance, e.g., along the entire edge or along a length corresponding to a work station (not shown). The rail 748 may be mounted to the table T2 by one or more rail mount(s) 749 (shown in FIG. 22B). In addition or alternatively, the rail 748 may be attached to the table T2 directly, or through a drape or cover (not shown).

To accommodate attachment of the load clamp 754, a load cleat 750 is attached to the load transfer tab 706 of the load transfer bracket 702. The load clamp 754 may be adjustably attached to the load cleat 750 using one or more conventional connectors, such as a slide, a dovetail, and the like. The load clamp 754 may be adjusted up or down relative to the load cleat 750 to optimize the engagement of the load clamp 754 with the table T2 for a given user U. As best seen in FIG. 22, the load clamp 754 includes a load clamp front tab 756, load clamp back tab 758, and load clamp top plate 749, which are configured to at least partially envelope or otherwise engage the rail 748 to provide structure to resist vertical forces, horizontal forces, and/or moments (similar to the attachment mechanisms described elsewhere herein, e.g., with reference to FIGS. 21D-E).

In certain applications, the user U and/or the adaptive arm support 500 may be contained within protective clothing, such as a sterile surgical gown or other garment G, as shown partially in FIGS. 22B and 22D. In one embodiment, a portion of the attachment accessory (e.g., the load clamp 754 shown in FIG. 22) may be outside of the protective clothing, e.g., within the sterile or other protected field, and another portion (e.g., the load cleat 750 to which the load clamp 754 attaches, as shown in FIG. 22) may be underneath the protective clothing, and the attachment accessory may connect to it through the protective clothing. In another embodiment, the attachment accessory may be underneath the protective clothing, e.g., outside the sterile or other protected field (e.g., the rail hook 746 shown in FIG. 22D and described further below).

The protective clothing may include special features, for example, to protect the clothing from abrasion from the rail 748 (e.g., a protective patch, not shown), and/or to ease connection of the load clamp 754 to the load cleat 750 through the protective clothing (e.g., a molded clip, also not shown).

As shown in FIG. 22B, the garment G may be clamped between the load cleat 750 and the load clamp 754. In this manner, forces may be transmitted from the harness assembly 510 through the garment G to the rail 748. One advantage of the load clamp 754 being outside of the garment G is that the load clamp 754 may include features to interface with the rail 748 that are incompatible with being covered by a garment (such as rollers, clips, latches, skids, and the like (not shown).

Optionally, the garment G may have a molded, extruded, or otherwise formed interface feature (not shown), which may ease and/or optimize attachment of the load clamp 754. In an alternative embodiment, the load clamp 754 may be pre-attached to or otherwise incorporated into the garment G.

Turning to FIGS. 22C and 22D, yet another exemplary embodiment of an attachment accessory, namely a rail hook 746, is shown that may be coupled to the adaptive arm support system 500 (or any other embodiment herein) to transfer loads to a specialized table T2. Similar to the table hook 720 shown in FIG. 21C, the rail hook 746 provides structure that may impart a vertical (downward) force (the weight of the adaptive arm support system 500, the arms of user U, and/or any tools or other objects held by the user U) transferred from the harness assembly 510 through a rail hook tab 766 to the table T2, and/or impart a horizontal (sideways) force transferred from the harness assembly 510 through a rail hook tail 769 to the table T2. Optionally, as best seen in FIG. 22D, the rail hook 746 may include a rail tab lead 747 on the rail hook tab 766, which may ease engagement of the rail hook 746 to the rail 748. In addition or alternatively, the rail hook 746 may be adjustable relative to the load transfer tab 706 of the load transfer bracket 702, e.g., using an adjustment knob 730 or other mechanism (not shown), to optimize the engagement of the rail hook 746 with the table T2 for a given user U, similar to other embodiments herein. Alternatively, other adjustment mechanisms may be provided, for example, clips, ratchets, burdock fasteners, screws, and the like (not shown).

The rail hook 746 may be substantially rigid, flexible, articulating, spring-loaded, damped, compressible, bendable, flexible in only one axis, or flexible in two or more axes, and/or may be formed from a variety of materials, such as metal, polymer, elastomer, or combination thereof. In addition or alternatively, the rail hook 746 may have additional features to contact the rail 748, such as pads, skids, rollers, wheels, balls, pins, cleats, burdock fasteners, magnets, vacuum, and the like (not shown), all similar to other embodiments herein.

With particular reference to FIG. 22D, the user U and/or the adaptive arm support system 500 may be contained within protective clothing, such as garment G (partially shown in FIG. 22D), such as a sterile surgical gown, a jumpsuit, a shirt, an apron, a sheet, or a patch attached to an existing garment. The garment G may be formed from a variety of materials, such as fabric, polymer film, a membrane, and/or may be substantially liquid proof, airtight, abrasion resistant, heat resistant, chemical resistant, radiation resistant, and the like.

In one embodiment, the rail hook 746 may be underneath the garment G, as shown in FIG. 22D, such that the material of the garment directly contacts the rail 748 and the rail hook 746 only indirectly engages the rail 748 through the garment G. Optionally, the garment G may include special features, for example, an abrasion-resistant patch (not shown), to protect the garment G from abrasion due to contact with the rail 748 and/or other structures. Other special features may include molded, extruded, or otherwise formed components (not shown) joined to the garment G, e.g., to facilitate engagement of the rail hook 746 to the rail 748 through the garment G. For example, a molded shield or clip (not shown), attached to the garment G (and possibly interfacing with the rail hook 746) may provide features that aid in attachment, retention, friction management, adjustment, padding, damping, resilience, and the like.

Turning to FIGS. 23A and 23B, another exemplary embodiment of an attachment accessory, namely a table hook 760, is shown that may be coupled to the adaptive arm support system 500 (or any other embodiment herein) to transfer loads to a table T3 before which a user is seated.

Similar to the table hook 720 shown in FIGS. 21A-C, the table hook 760 may be adapted for a seated position wherein the user U is seated in a chair C1 at the table T3, i.e., to transfer loads from the adaptive arm support system 500 to the table T3. Load may also be borne by the user U's lap, e.g., as defined by lap reaction force R1 (shown in FIG. 18). Optionally, as with other embodiments herein, transfer of loads from the adaptive arm support system 500 to the table T3 may be achieved through a protective gown, drape, cover, or other protective barrier (not shown). As best seen in FIG. 23B, the table hook 760 includes a table hook tab 762, which performs a similar function as the table hook tab 724 of the table hook 720 of FIGS. 21A-C.

Figure 23D:
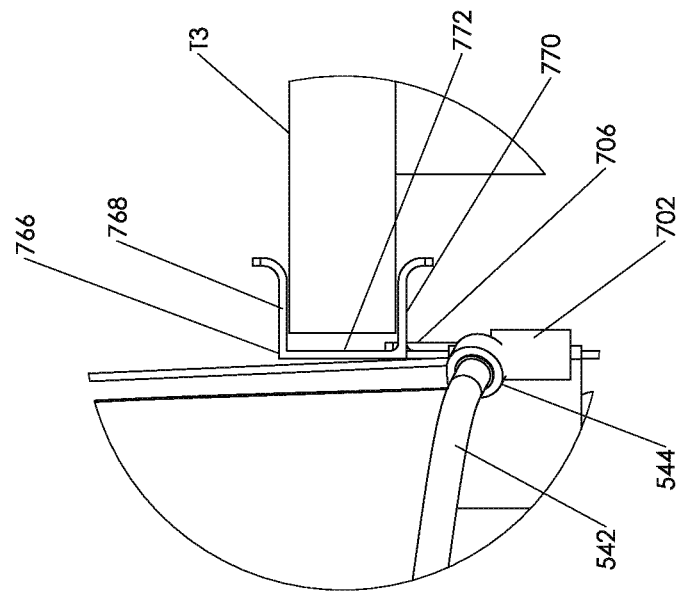
FIG. 23D is a detail of the cooperation between the load transfer bracket of the system of FIG. 23C and the table.
Figure 23C:
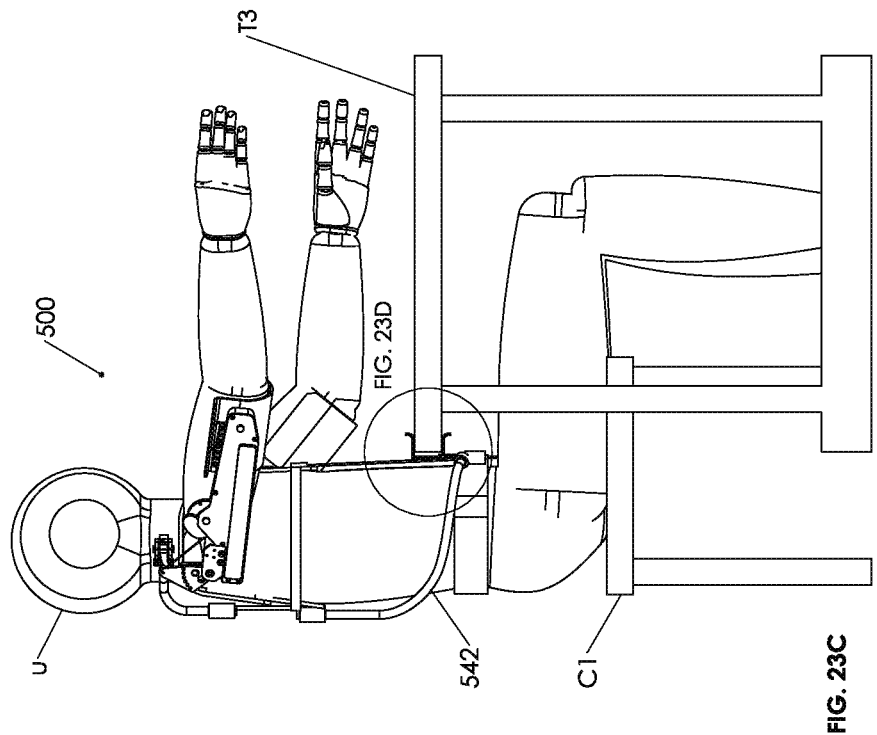
FIG. 23C is a side view of the system of FIGS. 13A and 13B worn by a user and including still another alternative embodiment of a load transfer bracket being at least partially supported by a table while the user is seated at the table.

Turning to FIGS. 23C and 23D, another embodiment of an attachment accessory, namely a table clamp 766, is shown that may be coupled to the adaptive arm support system 500 (or any other embodiment herein) to transfer loads to a table T3 before which a user is seated. Similar to table clamp 734 shown in FIGS. 21D-E, the table clamp 766 includes a clamp II top tab 768, clamp II bottom tab 770, and clamp II back 772, which perform similar functions as the table clamp upper tab 736, table clamp lower tab 742, and table clamp back 740, respectively, of the table clamp 734, but adapted for a user U seated in chair C1 at table T3, to transfer loads from the adaptive arm support system 500 to the table T3.

Figure 24B:
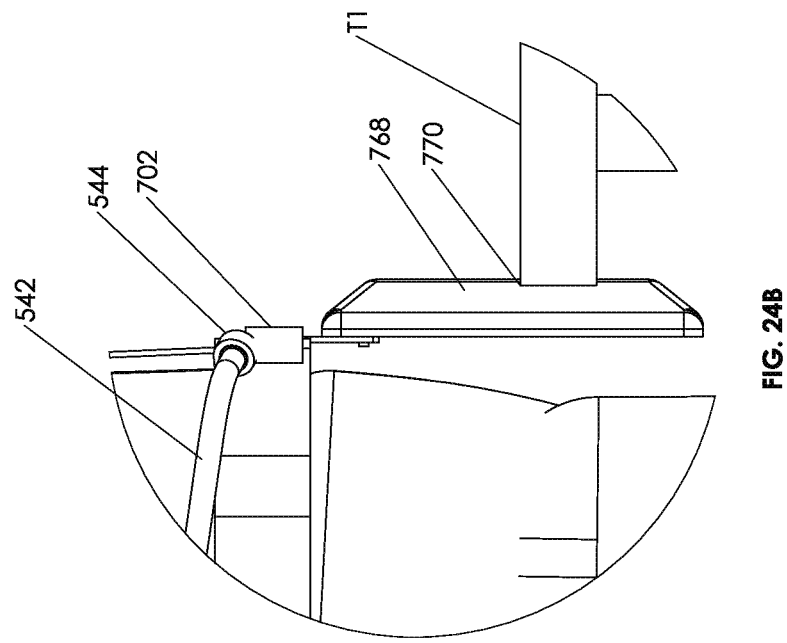
FIG. 24B is a detail of the cooperation between the load transfer bracket of the system of FIG. 24A and the table.
Figure 24A:
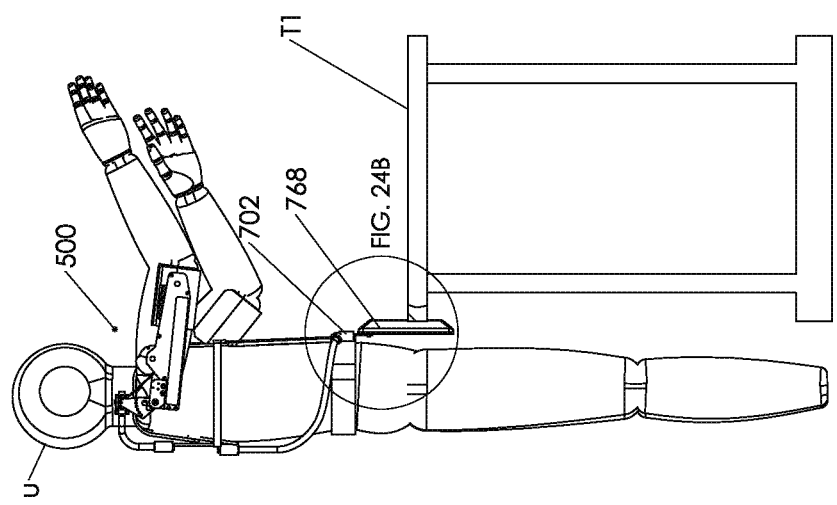
FIG. 24A is a side view of the system of FIGS. 13A and 13B worn by a user and including yet another alternative embodiment of a load transfer bracket being at least partially supported by a table.

Turning to FIGS. 24A and 24B, still another embodiment of an attachment accessory, namely a load transfer pad 768, is shown that may be coupled to the adaptive arm support system 500 (or any other embodiment herein) to transfer loads to a table T1 or other structure (e.g., a car frame or other structure) before which a user is standing. Similar to other attachment accessories herein, the load transfer pad 768 is attached to the load transfer bracket 702 of the system 500, and engages the edge of the table T1 at transfer contact point 770. The load transfer pad may be resilient and/or may deflect at the transfer contact point 770, e.g., allowing the edge of the table T1 to embed partially into the face of the load transfer pad 768. The load transfer pad 768 may have a substantially flat, domed, concave, convex, curved, or other shaped contact surface, and/or may be formed from relatively soft, stiff, and/or sticky materials, e.g., formed from metal, polymer, elastomer, or combination thereof.

Turning to FIGS. 25A and 25B, an alternative embodiment of an arm support assembly 505 is shown that includes a pivoting arm rest 600. The arm rest 600 may be configured to pivot about arm rest Pivot 780 located in arm rest pivot tab 782 of the chassis 580, e.g., in order to accommodate the angle of the user's arm (not shown). As shown in FIG. 25A, the arm rest upper surface 784 is tilted upward at Angle A20, while in FIG. 25B, the arm rest upper surface 784 tilted downward at Angle A21.

In addition or alternatively, an arm support assembly 505 may be provided that includes a translating arm rest 600. The arm rest 600 may include an arm rest slide base 796 fixedly attached to the chassis 580. An arm rest slide 798 is slidably joined to the arm rest slide base 796, and fixed to the arm rest 600, in order to accommodate the position of the user's arm. As shown in FIG. 26A, the arm rest slide 798 is displaced away from the arm rest slide base 796 by distance X5, while in FIG. 26B, the arm rest slide 798 is displaced away from the arm rest slide base 796 by distance X6 (greater than distance X5), indicating translation of the arm rest 600 along the longitudinal axis of the chassis 580. It will be appreciated that the arm rest slide 798 may be fixed at a plurality of locations along the arm rest slide base 796, e.g., depending on the number of positions available, and/or may be able to translate freely. Optionally, the arm rest 600 may both pivotable and translatable.

Figure 27B:
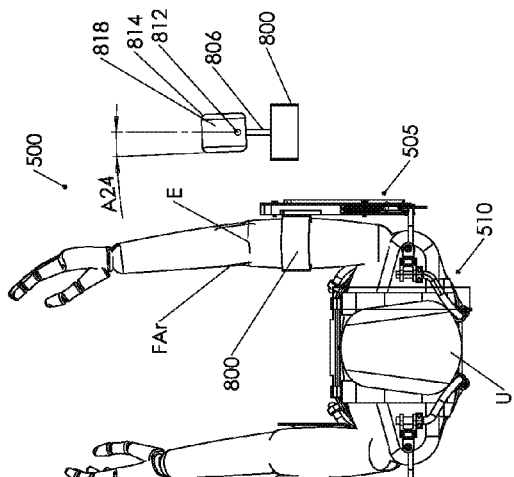
FIGS. 27B and 27C are top views of the system of FIG. 27A, showing one of the forearm supports pivoting to accommodate movement of the user's forearm.
Figure 27C:
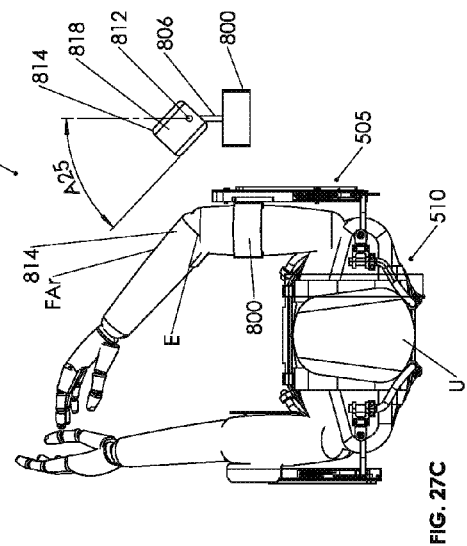
Figure 27A:
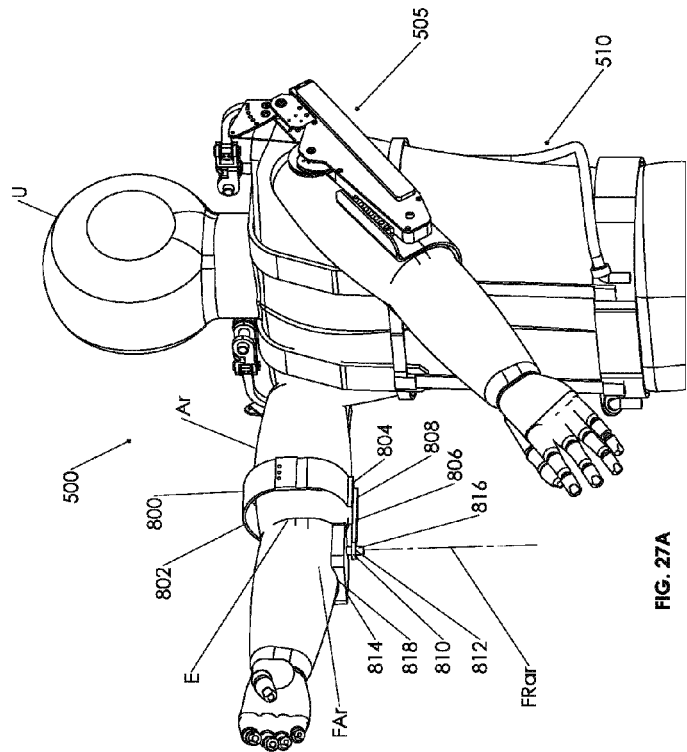
FIG. 27A is a front perspective view of another exemplary embodiment of an adaptive arm support system including forearm supports worn by a user.

Turning to FIGS. 27A-27B, another embodiment of an adaptive arm support 500 is shown that includes an arm rest 800 including a forearm rest 814, which may be desired by users who prefer to have some support of their forearm FAr, as well as the upper arm. As best seen in FIG. 27A, the arm rest 800 includes an arm rest top strap 802 and a pivot bracket pad 804. The arm rest top strap 802 may serve to ensure that the user U's arm Ar remains engaged with the arm rest 800, e.g., even if the user U lifts the arm Ar relative to the arm support assembly 505.

As best seen in FIG. 27A, the pivot bracket pad 804 provides a mounting location for a pivot bracket 806, which is substantially fixed or otherwise joined to the pivot bracket pad 804, e.g., at pivot bracket attachment point 808. The pivot bracket 806 includes a pivot bracket socket 810, and the forearm rest 814 includes a forearm rest pivot shaft 816 and forearm rest contact surface 818. The forearm rest pivot shaft 816 and pivot bracket socket 810 cooperate to form pivot 812 about which the forearm rest 814 may rotate, e.g., as defined by forearm rotate axis FRar, which may coincide with the elbow E of the user U. The forearm FAr generally may contact the forearm rest 814 at forearm rest contact surface 818.

In FIGS. 27B and 27C, the forearm rest 814 is shown adjacent the user U's arm to facilitate identification of the forearm rest 814. As shown in FIG. 27B, the forearm rest 814 is shown with the forearm FAr substantially straight, e.g., defining angle A24 with respect to the midline of the arm rest 800. In FIG. 27C, the forearm rest 824 is shown with the forearm FAr bent inward, e.g., such that the forearm rest 814 describes angle A25 with respect to the midline of the arm rest 800.

Turning to FIG. 28, still another embodiment of an arm support assembly 505 is shown that includes a sling-style arm rest, e.g., for users who desire a "sling" or "hammock" style arm rest. The arm support assembly 505 includes a sling armrest bracket 824, e.g., attached to the chassis 580 at arm rest pivot tab 782, and a sling armrest shell 826 joined to the sling armrest bracket 824 at sling armrest attachment 828. The sling armrest attachment 828 may be substantially rigid, flexible, or pivotable. A sling 830 is attached to the sling armrest shell 826 at both ends, creating sling saddle 832. The sling 830 may be flexible, semi-flexible, and/or may be padded, formed from mesh, elastic, and/or other material, as desired. In addition or alternatively, the arm rest 800 (or any of the other arm rests disclosed herein) may include one or more straps or other securing members (not shown), which may be wrapped or otherwise engaged around a user's arm to secure the user's arm in the arm rest.

Turning to FIGS. 29A-29E another embodiment of an adaptive arm support system 500 is shown that includes arm support assemblies 505 capable of flip-back storage. For example, in some applications, an additional pivot axis may be provided on the harness assembly 510, e.g., to permit the arm support assembly 505 to be lifted up as desired during use, and/or to be flipped back over the user U's shoulder and secured in place when not in use.

In the embodiment shown, a flip-back axis FBal (left) and flip-back axis FBar (right) are provided to permit each arm support assembly 505 to be selectively pivoted backward over the user U's shoulder for storage. For example, as best seen in FIGS. 29B and 29C, flip-back clamp I 854 and flip-back clamp II 856 may together create flip-back pivot 858, which is further defined by flip-back axis FBar (right), about which the flip-back clamp II 856 and arm support assembly 505 may rotate. A resilient element, such as a torsion spring (not shown), may bias the flip-back clamp II 856 and arm support assembly 505 to rotate in a preferential direction, for example upward (e.g., to aid in overhead tasks by increasing the range of the arm support assembly 505, at least lifting the weight of the arm support assembly 505 itself). The flip-back clamp I 854 may be fixedly mounted to flip-back mount tube 850 (and thereby to the harness assembly 510).

Shoulder pivot mount 548 is attached to the flip-back clamp II 856. When the flip-back clamp II 856 rotates relative to flip-back clamp I 854 about pivot 858, the arm support assembly 505 (not shown, see, e.g., FIGS. 29B-29E)), which is attached to the flip-back clamp II 856 via the shoulder pivot mount 548, shoulder pivot clevis 550, and support bar 554, rotates as well.

As best seen in FIG. 29C, the flip-back clamp I 854 is fixedly mounted to the flip-back mount tube 850. The flip-back clamp II 856, which rotates relative to flip-back clamp I 854 about pivot 858 and flip-back axis (right) FBar, must be limited in its rotation in order to support the weight of the user's arm (not shown). Flip back stop pin 864 is pressed into or stop pin bore 868 or otherwise attached to the flip-back clamp II 856. Stop pin free end 866, of the flip back stop pin 864, is aligned with clamp I slot 860, and does not interfere with this slot until it makes contact with clamp I slot end 862, thereby limiting the rotation of the flip-back clamp II 856, and maintaining it in the "use" position shown in FIGS. 29A-C.

Figure 29E:
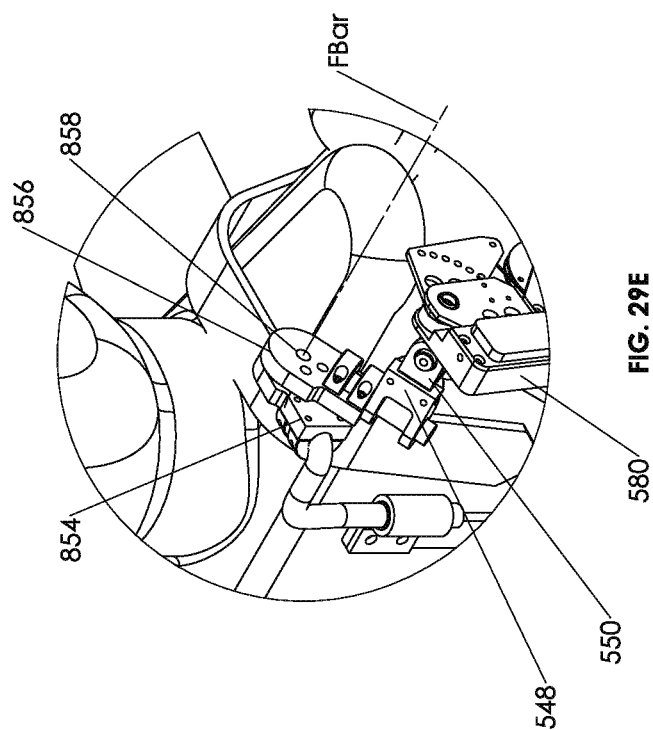
FIG. 29E is a detail of the components of the storage mechanism of the system of FIGS. 29A and 29D with the arm rest in the inactive position.
Figure 29D:
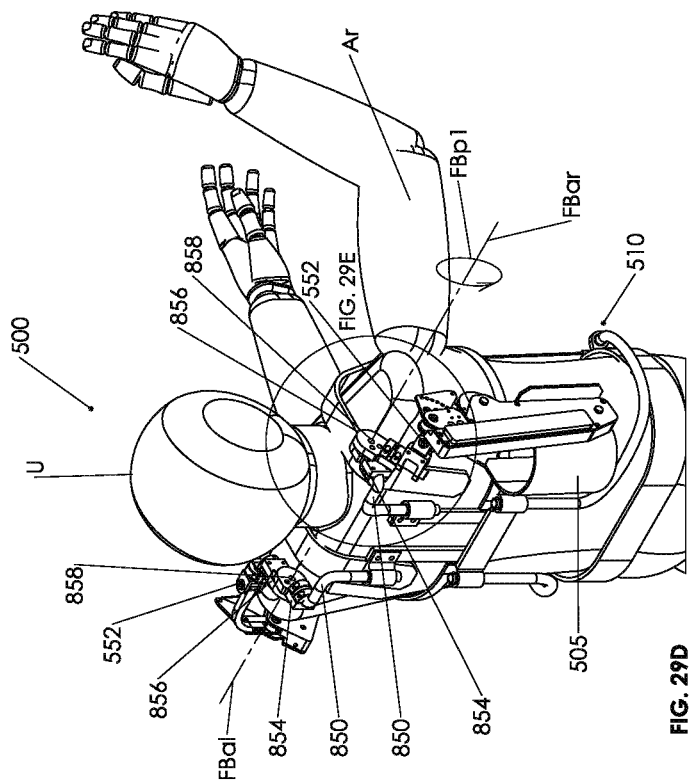
FIG. 29D is a rear perspective view of the system of FIG. 29A with one of the arm rests stored in an inactive position.

In FIG. 29D, the right side arm support assembly 505 is shown being rotated into the storage position about axis FBar, approximately along flip-back path FBpl, leaving the user U's arm Ar free of the arm support assembly 505. In FIG. 29E, the flip-back clamp II 856 is shown being rotated relative to the flip-back clamp I 854 about pivot 858 into the storage position. In the storage position, the weight of the arm support assembly 505 may be sufficient to hold the arm support assembly 505 in the storage position, e.g., until the user U reactivates the arm support assembly 505. Alternatively, one or more releasable locking mechanisms (not shown) may be provided that may be selectively engaged and/or disengaged to secure the arm support assembly 505 in the storage position when not in use.

Turning to FIGS. 30A and 30B, another exemplary embodiment of an adaptive arm support system 870 is shown that includes many components similar to other embodiments herein, but includes an alternative shoulder pivot design. In this embodiment, the vertical pivot 552 shown in FIGS. 14A and 14B (which permits rotation about substantially vertical axis Uav associated with user U's shoulder) has been replaced by a series of linkages 880, located behind the user U's back, which pivot about substantially vertical axes. As shown in FIG. 30B, as the user U moves their arm Ar horizontally outward, the linkages 880 fold outward away from the user U's back, thereby leaving the area about the shoulder S of user U free from mechanical elements.

In this embodiment, link shoulder harness 875 includes two or more link elements 880 (two shown), which may pivot about one or more link pivots 890. The link elements 880 and link pivots 890 may transmit loads and/or moments from the arm support assembly 505 into the link shoulder harness 875. A link end element 894 joins the series of link elements 880 to an arm support assembly 505 to which the link end element 894 is fixedly mounted. As shown in FIG. 30A, the link pivots 890 connect the link elements 880 together to define dual link axis I DLa1, dual link axis II DLa2, and dual link axis III DLa3, all of which may be substantially parallel.

As shown in FIG. 30B, the adaptive arm support system 870 is shown with the arm support assembly 505 (and Arm Ar) rotated about substantially vertical axis Uav (associated with user U's shoulder, as previously described), approximately along dual link path DLpl. During this action, the link elements 880 have pivoted in response about dual link axis I DLa1, dual link axis II DLa2, and dual link axis III DLa3. When the arm Ar and arm support assembly 505 are moved back in the opposite direction, the link elements 880 may return to the configuration shown in FIG. 30A to accommodate the motion, all the while transmitting loads and/or moments from the arm support assembly 505 into the link shoulder harness 875.

Figure 31B:
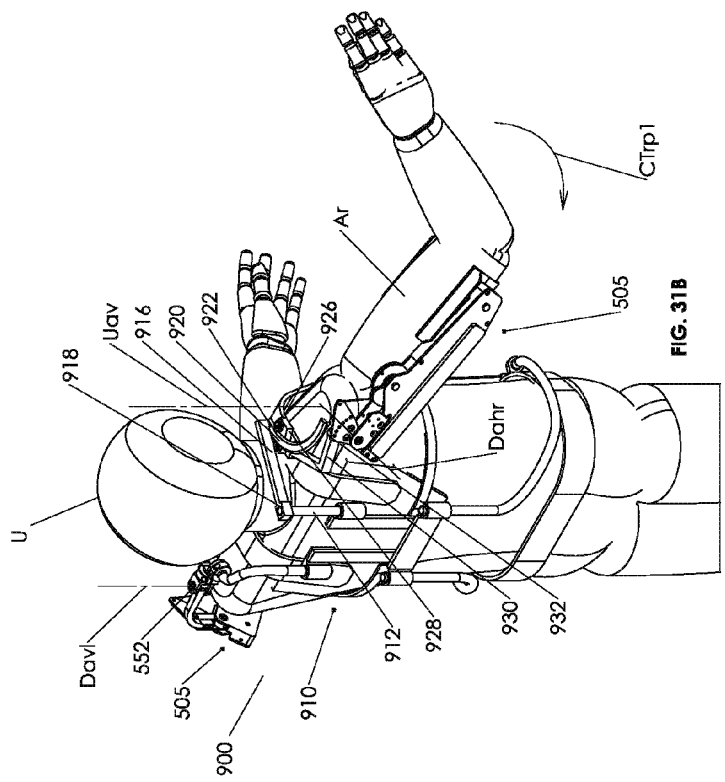
FIGS. 31A and 31B are rear perspective views of another exemplary embodiment of an adaptive arm support system worn by a user and including another alternative shoulder pivot mechanism.
Figure 31A:
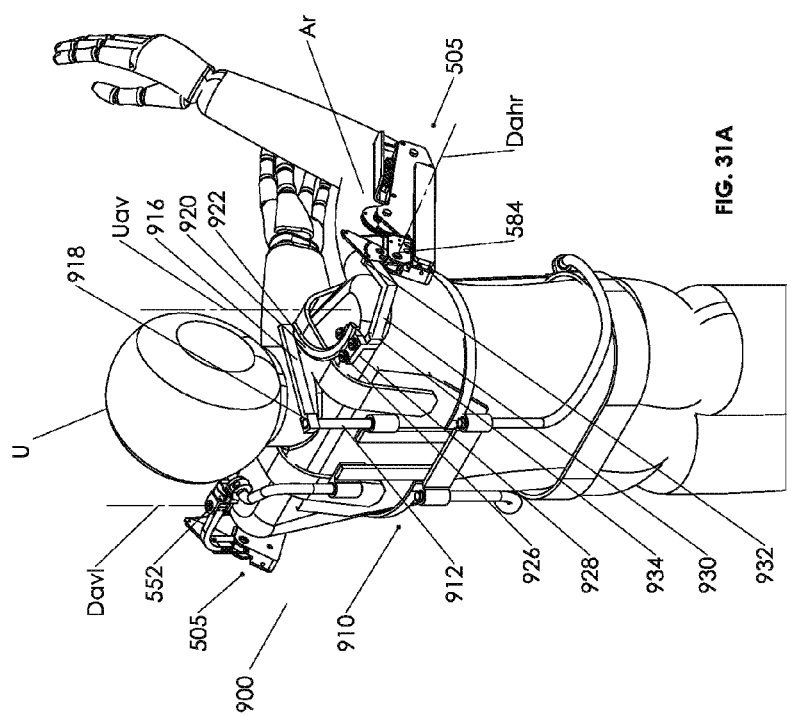

Turning to FIGS. 31A and 31B, yet another embodiment of an adaptive arm support system 900 is shown that includes several components similar to other embodiments herein, but includes an alternative shoulder pivot design. Unlike other embodiments, the system 900 includes a curved track harness 910, which features a curved track system, e.g., in place of the vertical pivot 552 of the system of FIGS. 14A and 14B, that allows rotation about substantially vertical axis Uav (associated with user U's shoulder, as previously described).

Curved track support bar 916 is mounted to curved track support tube 912 at support tube junction 918. Curved track 920 is attached to the curved track support bar 916 at curved track junction 922. Curved track rollers 926 are mounted on track carriage 928, and may freely travel along the curved track 920, e.g., in response to movement of the user's arm Ar, about vertical axis Uay. The curved track rollers 926 may transmit loads and/or moments from the arm support assembly 505 into the curved track harness 910. Curved track bracket 930 is mounted on the track carriage 928 at track bracket junction II 934, and in turn provides mounting for an arm support assembly 505, which joins the curved track bracket 930 at track bracket junction I 932.

Turning to FIG. 31B, the adaptive arm support system 900 is shown with arm support assembly 505 (and arm Ar) rotated about substantially vertical axis Uav (associated with user U's shoulder, as previously described), approximately along curved track rotation path CTrp1. During this action, the curved track rollers 926 have traveled along the curved track 920 in response to movement of the user's arm Ar about vertical axis Uay. Thus, the cooperation of the curved track rollers 926 and the curved track 920 accommodate horizontal movement of the arm Ar and arm support assembly 505, all the while transmitting loads and/or moments from the arm support assembly 505 into the curved track harness 910.

Figure 32:
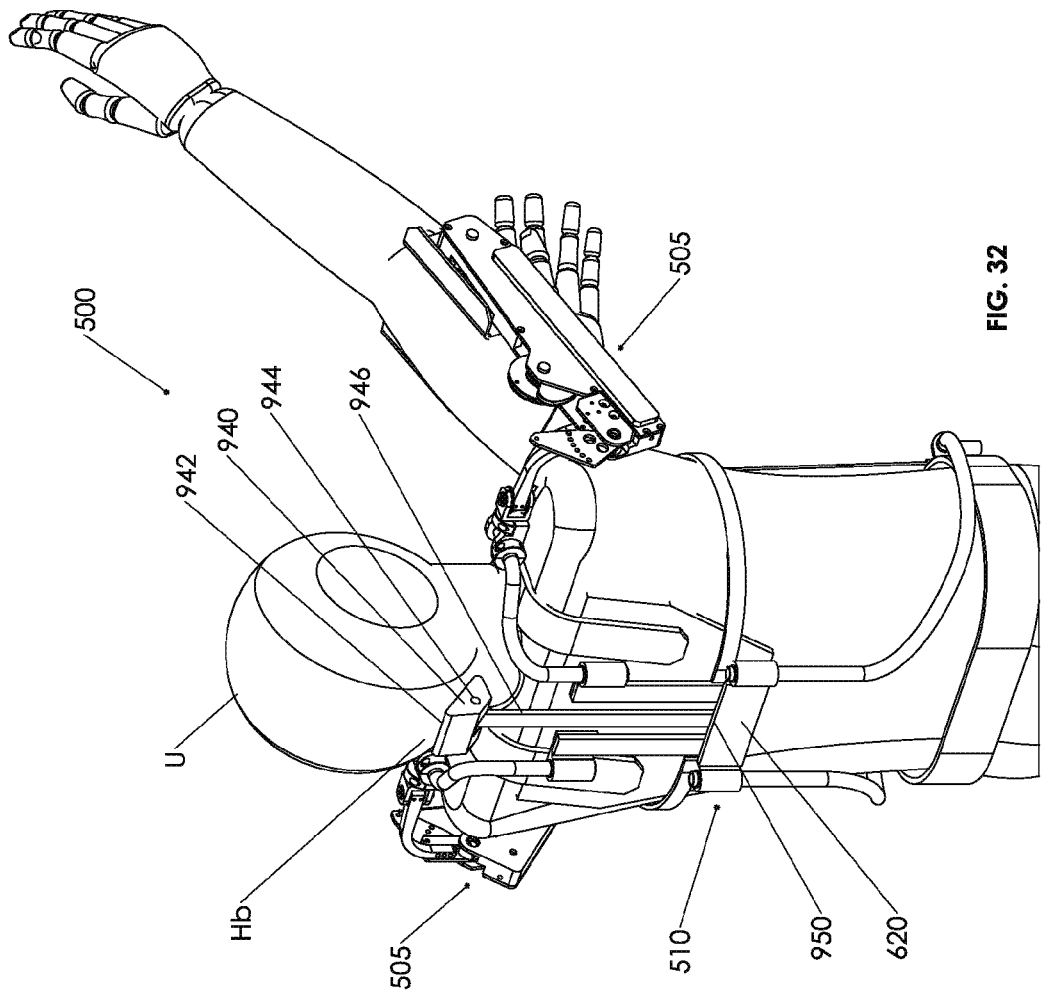
FIG. 32 is a rear perspective view of another exemplary embodiment of an adaptive arm support system including a head rest.

Turning to FIG. 32, another exemplary embodiment of an adaptive arm support system 500 is shown that is generally similar to the system 500 shown in FIGS. 14A and 14B, except that the system 500 includes a head rest 940. When working with arms outstretched overhead, a user U may have to work with his or her head tilted up, which can be tiring. An optional head rest 940, attached to the harness assembly 510, may be used to relieve this fatigue. The back of the head Hb of the user U is shown supported by head rest contact surface 942 of the head rest 940. The head rest 940 may be connected to head rest bracket 946, e.g., fixedly, or optionally at head rest pivot 944, which may allow the head rest 940 to pivot in response to the requirements of the user U. The head rest bracket 946 may be attached to the cross brace 620 at bracket junction 950 or elsewhere on the harness assembly 510, thereby permitting all, or a portion of, the weight of the user's head to be borne by the harness assembly 510.

Figure 33B:
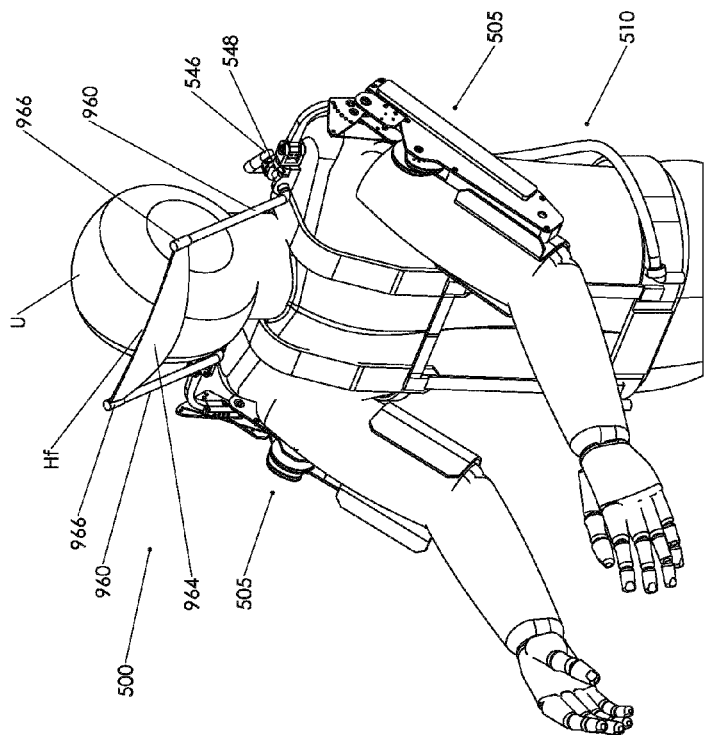
FIG. 33B is a front perspective view of still another exemplary embodiment of an adaptive arm support system including a forehead rest.
Figure 33A:
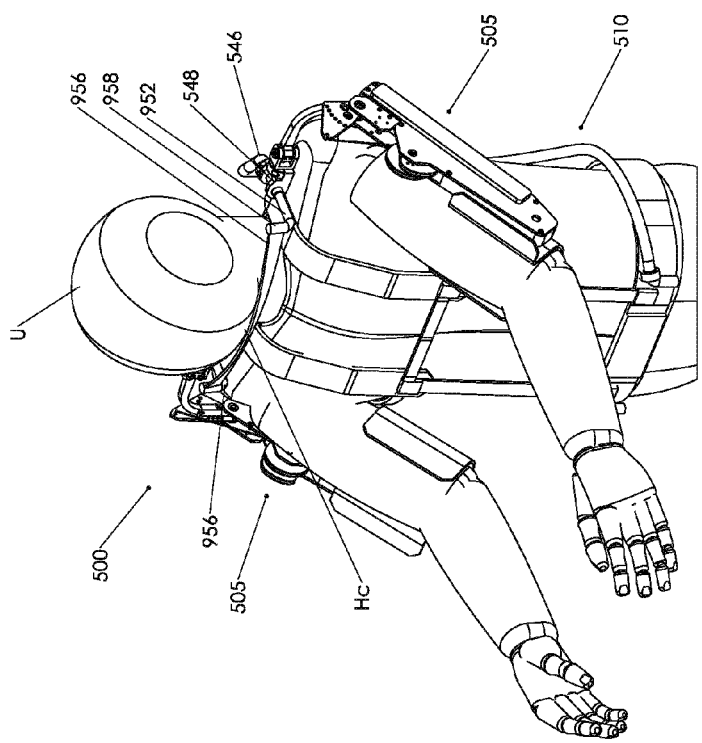
FIG. 33A is a front perspective view of yet another exemplary embodiment of an adaptive arm support system including a chin rest.

Turning to FIG. 33A, still another exemplary embodiment of an adaptive arm support system 500 is shown that is generally similar to the system 500 shown in FIGS. 14A and 14B, except that the system 500 includes a chin rest 956. When working with arms outstretched downward, a user U may have to work with his or her head tilted down, which can be tiring. An optional chin rest 956, attached to the harness assembly 510, may be used to relieve this fatigue. The user U's chin Hc is shown supported by the chin rest 956. The chin rest 956 may be attached to one or more chin rest brackets 952 at one or more chin rest junctions 958. The chin rest bracket(s) 952 may be attached to the harness assembly 510, for example, at shoulder pivot mount(s) 548 on either side of the user U's head.

Turning to FIG. 33B, yet another exemplary embodiment of an adaptive arm support system 500 is shown that is generally similar to the system 500 shown in FIGS. 14A and 14B, except that the system 500 includes a forehead rest 964. The user U's forehead Hf is shown supported by the forehead rest 964. The forehead support 964 is attached or otherwise coupled to one or more forehead brackets 960 at one or more support junctions 966. The forehead bracket(s) 960 may be removably or substantially permanently attached to the harness assembly 510, for example, at shoulder pivot mount(s) 548 on either side of the user U's head. Optionally, the bracket(s) 960 may be adjustable, e.g., to allow the forehead rest 964 to be adjusted, e.g., moved between a forehead support position and chin support position (not shown).

In an alternative embodiment, a chin rest 956 (such as that shown in FIG. 33A) and a forehead rest 964 (such as that shown in FIG. 33B) may be included together on any of the harnesses and/or apparatus described herein or in the applications incorporated by reference herein, e.g., to support a user's chin and forehead simultaneously. Used together, the chin rest 956 and forehead rest 964 may be adjustable relative to each other as desired by the user, for example, to accommodate the desired angle or position of the user's head. In addition or alternatively, the chin rest 956 and forehead rest 964 may be mounted together on a frame or structure (not shown) which may be mounted on, and/or may be moveable, rotatable, and/or adjustable relative to, the bracket(s) 960, e.g., on a faceplate, mask, or other features (not shown) mounted between the brackets 960. For example, the brackets 960 may be substantially rigid and/or stationary relative to the harness 510, while the features carrying the forehead rest 964 and chin rest 956 therebetween may be movable, e.g., within an orbital path to support the user's head while provided multiple degrees of freedom of movement.

Alternatively, the chin rest 956 and forehead rest 964 may simply be slings, pads, or other features mounted between the brackets 960 with the forehead rest 964 located on upper ends of the brackets above the chin rest 956. Optionally, the chin rest 956 and forehead rest 964 may be mounted together on a frame or structure (not shown) instead of the brackets 960, which may movable, e.g., may pivot, swivel, and/or otherwise adjust relative to the harness 510 and/or between the brackets 960, or which may move along an orbital path, or any combination thereof. The chin rest 956 and forehead rest 964 may be formed together from one piece, or from several pieces attached together. In yet another alternative, a harness assembly (such as assembly 510) may be provided that includes a chin rest 956 and/or a forehead rest 964 without an arm support assembly, e.g., to provide head support for a user while performing tasks that require the user to lean or bend forward, and the like.

The chin rest 956 and/or forehead rest 964 may be substantially rigid or flexible, elastic or inelastic, or any combination thereof. Optionally, the rests 956, 964 may be padded, segmented, and/or articulating. In addition or alternatively, one or both rests 956, 964 may be detachable from the harness, e.g., using one or more connectors (not shown), to allow the user to select which rest to use for a particular application or to remove one or both from service. Thus, all, or a portion of, the weight of the user's head may be borne by the harness assembly 510.

Turning to FIGS. 34A and 34B, an alternative embodiment of an arm support assembly 970 is shown that may be included in an adaptive arm support system (not shown), similar to other embodiments herein, e.g., instead of the arm support assembly 505 shown in FIGS. 14A and 14B. Unlike other arm support assemblies herein, the arm support assembly 970 includes a spring pack 980 remote from the arm rest assembly 975 itself. For example, the arm rest assembly 975 may include an arm rest 600 attached to the arm bracket 984, which, optionally, may pivot and/or translate, similar to other embodiments herein.

The spring pack 980 includes resilient element components for providing support forces moved from the chassis of the arm rest assembly 975 to the harness assembly 510 (not shown), such as to the shoulder support tube 546, shoulder pivot mount 548, shoulder pivot clevis 550, and/or support bar 554. In an exemplary embodiment, the spring pack 980 may be located some distance from the arm rest assembly 975, for example, on the frame strap 624 of the harness assembly 510 (not shown). Anchor plate 988, attached to the support bar 554, provides mounting points for cable housing terminal I 990 and pulley 994, which rotates about pulley pivot 996. Cable housing terminal II 1000 is attached to spring pack housing 1004. The anchor plate 988 may be rotatable relative to the support bar 554, e.g., to permit the user to change the range of use of the arm rest assembly 975. In addition or alternatively, the anchor plate 988 may also be releasable from the support bar 554, e.g., to permit the arm rest assembly 975 to rotate freely about the shoulder horizontal pivot 986, for example, to take the arm support assembly out of service.

Cable housing 992 terminates at the cable housing terminal I 990 and the cable housing terminal II 1000, and provides a conduit for primary cable 1026, which transmits force from the spring pack 980 to the arm rest assembly 975. The primary cable 1026 is attached to the arm bracket 984 at primary cable junction 1028, and is wrapped around the pulley 994 before entering the cable housing 992. The primary cable 1026 exits the cable housing 992 in the spring pack housing 1004, and wraps around primary pulley 1008. The primary cable 1026 is attached to the primary pulley 1008 at an attachment point (not shown), in a similar configuration as described elsewhere herein, e.g., with reference to FIGS. 14A and 14B.

The primary pulley 1008 is rigidly attached to secondary pulley 1012, and both rotate together about pulley pivot 1006, similar to other embodiments herein. Secondary cable 1020 is wrapped around the secondary pulley 1012 and is attached to the secondary pulley 1012 at attachment point (not shown), e.g., in a similar manner as the embodiment shown in FIGS. 14A and 14B. The secondary cable 1020 joins a first end of resilient element 1016 at secondary cable junction 1022. A second end of the resilient element 1016 is joined to the spring pack housing 1004, e.g. by resilient element anchor 1024.

The primary pulley 1008 and secondary pulley 1012 perform similar functions as the primary pulley 564 and secondary pulley 570 shown in FIGS. 14A and 14B and described elsewhere herein, e.g., to provide selective mechanical advantage/disadvantage to the resilient element 1016 during use, as desired for lift-force management.

Turning to FIG. 34B, the arm support assembly 970 is shown with the arm rest 600 lowered. The end of the primary cable 1026, which is attached to the arm rest assembly 975, is shown extended out of the cable housing 992 in response to rotation of the arm rest assembly 975 about pivot 986, approximately along remote spring rotation path RSrpl. During this motion, the primary cable 1026 has partially unwrapped from the primary pulley 1008, which has rotated in response about pulley pivot 1006, approximately along pulley path RSpp1. As the primary pulley 1008 has rotated about the pulley pivot 1006, the secondary pulley 1012 rotates simultaneously, causing the secondary cable 1020 to wrap around the secondary pulley 1012. The secondary cable 1020, in turn, extends the resilient element 1016.

It will be appreciated that the systems described above may be used in a variety of fields and applications. For example, the systems may be worn by physicians, e.g., surgeons, dentists, and the like, to facilitate extension of the physician's arm(s) during an extended surgical, medical, or dental procedure. The systems may be worn by construction workers, e.g., painters, carpenters, and the like, manufacturing workers, e.g., involved in product assembly, and the like, disabled individuals, and/or other users who perform tasks for an extended period of time in which one or both arms may be extended outwardly from the user's body.

Generally, the devices and systems herein may be worn or otherwise placed on the user's body, e.g., by securing a harness onto the user's abdomen, e.g., their waist, hips, shoulders, back, chest, and the like. An arm support of the devices or systems, e.g., coupled to or otherwise carried by the harness, may be used to support the user's arm such that the arm support subsequently follows movement of the user's arm. The user may then perform one or more tasks involving movement of the user's arm, the arm support at least partially offsetting a gravitational force acting on the user's arm and/or at least partially transferring the gravitational force to the user's abdomen (or other structures) during the movement without substantially interfering in the movement. Thus, the devices and systems herein may facilitate the user performing the task(s) for greater lengths of time and/or with reduced fatigue and/or injury. In addition or alternatively, other benefits may be realized, including reduced strain on the back and spine and/or improved hand stability by the user. In addition, any of the harness assemblies disclosed herein may provide a structure that may be used to support the back and spine, e.g., without an arm support assembly, if desired.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A system for supporting an arm of a user, comprising:
A harness configured to be worn on a body of a user;
An arm support coupled to the harness configured to support an arm of a user, the arm support configured to accommodate movement of the arm while following the movement without substantially interfering with the movement of the user's arm, the arm support comprising:
A first arm support segment pivotally coupled to the harness about a first vertical axis such that the first arm support segment is rotatable substantially horizontally about the first vertical axis relative to the harness;
A second unitary arm support segment comprising a first end pivotally coupled to the first arm support segment such that the second arm support segment is rotatable about a second axis orthogonal to the first vertical axis, a second free end; and
An arm rest carried on the second arm support segment for supporting an upper arm of the user's arm; and
One or more compensation elements coupled to the arm support to apply an offset force to at least partially offset a gravitational force acting on the arm as the user moves and the arm support follows the movement of the user's arm, the one or more compensation elements varying the offset force applied to the second arm support segment as the second arm support segment rotates about the second axis when the user raises or lowers the arm.

2. The system of claim 1, wherein the one or more compensation elements comprise a spring comprising a first end attached to the second arm support segment, a first pulley assembly including primary and secondary pulleys coupled together on a common axis and mounted on the second arm support segment, a first cable coupled between a second end of the spring and the secondary pulley, and a second cable coupled between the primary pulley and the first arm support segment such that at least a portion of a force from the spring is applied to the second arm support segment to generate the offset force.

3. The system of claim 2, wherein at least one of the primary and secondary pulleys has an asymmetric noncircular shape to modify the portion of the force of the spring applied to the second arm support segment based on a location of the second arm support segment about the second axis.

4. The system of claim 1, wherein the one or more compensation elements comprise a spring carried on the second arm support segment such that the offset force applied by the spring is reduced as the second arm support segment is lowered in order to reduce a compensating force applied to the arm.

5. The system of claim 1, wherein the one or more compensation elements comprise:
   a first pulley assembly mounted on the second arm support segment;
   a spring comprising a first end attached to the second arm support segment; and
   a first cable comprising a first end coupled to a second end of the spring and extending at least partially around the first pulley assembly to apply the offset force.

6. The system of claim 5, wherein the first pulley assembly comprises a reversing pulley mounted at the second end of the second arm support segment.

7. The system of claim 6, wherein the first cable extends around the reversing pulley such that a second end of the first cable is mounted to the second arm support segment between the first and second ends.

8. The system of claim 7, wherein the one or more compensation elements further comprise a second pulley assembly mounted on the second arm support segment and wherein the second end of the first cable is coupled to the second pulley assembly.

9. The system of claim 8, further comprising a second cable comprising a first end coupled to the second pulley assembly and a second end coupled to the first arm support segment.

10. The system of claim 9, wherein the second pulley assembly includes a primary pulley and a secondary pulley mounted on a common axis, the second end of the first cable is coupled to the secondary pulley and the first end of the second cable is coupled to the primary pulley.

11. The system of claim 1, wherein the first arm support segment comprises a hinge bracket coupled between a support fixed to the harness and the second arm support segment.

\* \* \* \* \*